(12) United States Patent
De Brouwer et al.

(10) Patent No.: US 11,276,483 B2
(45) Date of Patent: Mar. 15, 2022

(54) SYSTEMS, METHODS, AND APPARATUS FOR PERSONAL MEDICAL RECORD KEEPING

(71) Applicant: HEALTHY.IO LTD., Tel Aviv-Jaffa (IL)

(72) Inventors: Walter De Brouwer, Los Altos, CA (US); Alexander Cristoff, Palo Alto, CA (US); Scott Thomas, Oakland, CA (US)

(73) Assignee: HEALTHY.IO LTD., Tel Aviv (IL)

( * ) Notice: Subject to any disclaimer, the term of this patent is extended or adjusted under 35 U.S.C. 154(b) by 476 days.

(21) Appl. No.: 16/071,431

(22) PCT Filed: Jan. 22, 2017

(86) PCT No.: PCT/US2017/014482
§ 371 (c)(1),
(2) Date: Jul. 19, 2018

(87) PCT Pub. No.: WO2017/127778
PCT Pub. Date: Jul. 27, 2017

(65) Prior Publication Data
US 2020/0286600 A1 Sep. 10, 2020

Related U.S. Application Data

(60) Provisional application No. 62/286,310, filed on Jan. 22, 2016.

(51) Int. Cl.
*G16H 10/60* (2018.01)
*G16H 15/00* (2018.01)
(Continued)

(52) U.S. Cl.
CPC ............... *G16H 10/60* (2018.01); *A61B 5/20* (2013.01); *G16H 15/00* (2018.01); *G16H 40/67* (2018.01);
(Continued)

(58) Field of Classification Search
CPC ............................. G16H 10/40; G16H 10/60
See application file for complete search history.

(56) References Cited

U.S. PATENT DOCUMENTS 9,808,206 B1 * 11/2017 Zhao .................... A61B 5/0295
10,354,753 B2 * 7/2019 Lynn ..................... G16H 50/80
(Continued)

*Primary Examiner* — Michael Tomaszewski
*Assistant Examiner* — Jay M. Patel
(74) *Attorney, Agent, or Firm* — Finnegan, Henderson, Farabow, Garrett & Dunner, LLP

(57) ABSTRACT

Systems, methods, and apparatus are disclosed aggregating at least two of vital signs data, diagnostic test results, medical data, and user parameters into a single medical record. In one example, a method may include periodically receiving vital signs data and/or diagnostic test results performed on a user; periodically receiving medical data in response to a medical examination of the user performed by a health care practitioner; receiving user parameters about the user; aggregating the vital signs data and/or diagnostic test results, the medical data, and the user parameters into a single medical record; associating the single personal medial record with the user; and storing the single personal medial record into a database of personal medical records. Life expectancy can be calculated. Data aggregation can be performed over time for comparison in real time to medical standard values allowing the user to set personal goals towards greater life expectancy.

18 Claims, 63 Drawing Sheets

(51) Int. Cl.
  *G16H 40/67*  (2018.01)
  *G16H 50/30*  (2018.01)
  *G16H 50/70*  (2018.01)
  *G16H 50/20*  (2018.01)
  *A61B 5/20*   (2006.01)
  *G06Q 30/02*  (2012.01)

(52) U.S. Cl.
  CPC ............ *G16H 50/20* (2018.01); *G16H 50/30* (2018.01); *G16H 50/70* (2018.01); *G06Q 30/0277* (2013.01)

(56) References Cited

U.S. PATENT DOCUMENTS

| | | | | |
|---|---|---|---|---|
| 2004/0138716 A1* | 7/2004 | Kon | ............... | A61N 1/36557 607/17 |
| 2007/0219059 A1* | 9/2007 | Schwartz | ............... | A61B 7/003 482/8 |
| 2013/0116520 A1* | 5/2013 | Roham | ............... | A61B 5/6833 600/324 |
| 2013/0291060 A1* | 10/2013 | Moore | ............... | G16H 40/63 726/1 |
| 2013/0296714 A1* | 11/2013 | Kassim | ............... | G01N 21/3151 600/479 |
| 2014/0249858 A1* | 9/2014 | Moore | ............... | G16H 10/60 705/3 |
| 2014/0278487 A1* | 9/2014 | Moore | ............... | G06Q 10/06 705/2 |
| 2015/0044098 A1* | 2/2015 | Smart | ............... | G01J 3/2823 422/82.05 |
| 2015/0096942 A1* | 4/2015 | Wang | ............... | G01K 1/026 210/742 |
| 2015/0313484 A1* | 11/2015 | Burg | ............... | A61B 5/021 600/301 |
| 2016/0074861 A1* | 3/2016 | Phillips | ............... | G01N 33/558 506/39 |

* cited by examiner

FIG. 22B

HOME DETAIL

QUESTION ATTRIBUTES
- CATEGORIES
- PARENT QUESTION
- ANSWERS
- SIBLING QUESTIONS

2641

2642

MOMENTS

Supporting photos and photos or PDF of documents are attached.

| LIFE EXPECTANCY | QUARTILE | CREDIT | TRANCHE | INSURANCE | HEALTHCARE |
|---|---|---|---|---|---|
| 73-3 | LOWER | AA- | JUNIOR | STANDARD | REACTIVE |
| 80-92 | MEDIAN | AA | SENIOR SUPER | SELECT | ACTIVE |
| 93-97 | UPPER | AA+ | SENIOR LSS | PREFERRED | PROACTIVE LIFE |
| 95-100 | LEVERAGED | AAA | | PREFERRED PLUS | EXTENSION |

FIG. 29

Lack of industry guidelines leave a lot of the discretion of doctors & their patients

| CONDITION | "X" OUT OF 5 BIOMARKERS ARE: | BLOOD TEST INDUSTRY SCREENING GUIDELINES | BLOOD TEST PACKAGES |
|---|---|---|---|
| High Cholesterol | ●●●●● | Once every 5 years, or at the physician's discretion depending on risk factors | Screen: Cardio<br>In-Depth: Core Health Health |
| High Blood Pressure | ●●●●● | No pre blood test, however, related to heart health. See above. | Screen: Cardio<br>In-Depth: Core Health Health |
| Arthritis | ●●●●● | No guidelines | Screen: Inflammation<br>In-Depth: Arthritis |
| Diabetes | ●●●●● | Once every 3 years, or at the physician's discretion depending on risk factors | Screen: Glucose & Metabolism<br>In-Depth: Diabetes |
| Thyroid Disease | ●●●●● | No guidelines | Screen: Glucose & Metabolism<br>In-Depth: Thyroid |
| Vitamins & Minerals | ●●●●● | No guidelines | Screen: Vitamins & Minerals<br>In-Depth: N/A |
| Primary Immune Deficiency/Anemia | ●●●●● | No guidelines | Screen: Blood Health<br>In-Depth: N/A |
| Kidney Disease | ●●●●● | No guidelines | Screen: Kidney & Liver<br>In-Depth: N/A |

FIG. 39

SYSTEMS, METHODS, AND APPARATUS FOR PERSONAL MEDICAL RECORD KEEPING

CROSS-REFERENCE TO RELATED APPLICATIONS

This United States (U.S.) non-provisional patent application claims the benefit of International Patent App. No. PCT/US2017/014,482; titled SYSTEMS, METHODS, AND APPARATUS FOR PERSONAL MEDICAL RECORD KEEPING; filed on Jan. 22, 2017 by Walter De Brouwer et al. International Patent App. No. PCT/US2017/014,482 claims the benefit of U.S. provisional patent application No. 62/286,310; filed on Jan. 22, 2016 by Walter De Brouwer et al, incorporated herein by reference for all intents and purposes.

FIELD OF THE INVENTION

This invention generally relates to medical records and data bases that store medical record information.

BACKGROUND OF THE INVENTION

Healthcare is a key element of any modern society. Over the years, it has brought people the benefit of the latest technological breakthroughs that are safeguarded by well-established regulatory process. The practice of medical practitioners has also evolved into highly specialized fields and subfields. Medical practitioners previously kept medical records and medical charts of their patients. Patients often do not understand their own medical records or medical charts. This may be partly due to the complex terminology used in the medical profession. This may also be due in part due to the fact the patient did not keep and maintain his or her own medical record.

Patients over the years often change the medical practitioners that they see. Often the medical records and medical charts kept by medical practitioners are not transferred from one doctor to the next as the patient ages and/or sees and consults with other doctors. Patients may not fully recall all of their prior medical procedures to explain to their next doctor the prior procedures they may have undergone. Accordingly, the next doctor a patient consults often does not know the prior procedures that a prior doctor performed on a patient.

Prior medical history may be important to diagnose a future ailment of a patient and make better decisions on health care. Prior medical history of related family members may be helpful to diagnose a future ailment of a patient. When parents and grandparents pass away, their medical history is often lost and unavailable to living relatives. Memory of ailments that a parent or grandparent may have had often fades over time.

It is desirable to improve upon medical record keeping of patients and to help them to better understand and improve their health.

SUMMARY OF THE INVENTION

The embodiments of the invention are best summarized by the claims below. Insofar as a summary is required, one embodiment of the invention can be described as methods, systems, and apparatus including a medical record data base for personal medical record keeping.

This summary is provided to efficiently present the general concept of the invention and should not be interpreted as limiting the scope of the claims.

BRIEF DESCRIPTION OF THE DRAWINGS

These and other features, aspects, and advantages of the present disclosure will now be described with reference to the drawings of embodiments, which embodiments are intended to illustrate and not to limit the disclosure, as are described in varying degrees of detail below.

FIG. 22B illustrates details of a single personal medical record.

FIG. 29 is a chart illustrating life expectancy quartiles and life expectancy and various health care plans for a user.

FIG. 39 illustrates the various blood test screening to be performed using the blood test kit and/or the blood test lab as the user ages to form the medical history for the user in the personal medical records database.

DETAILED DESCRIPTION

Figure 1A:
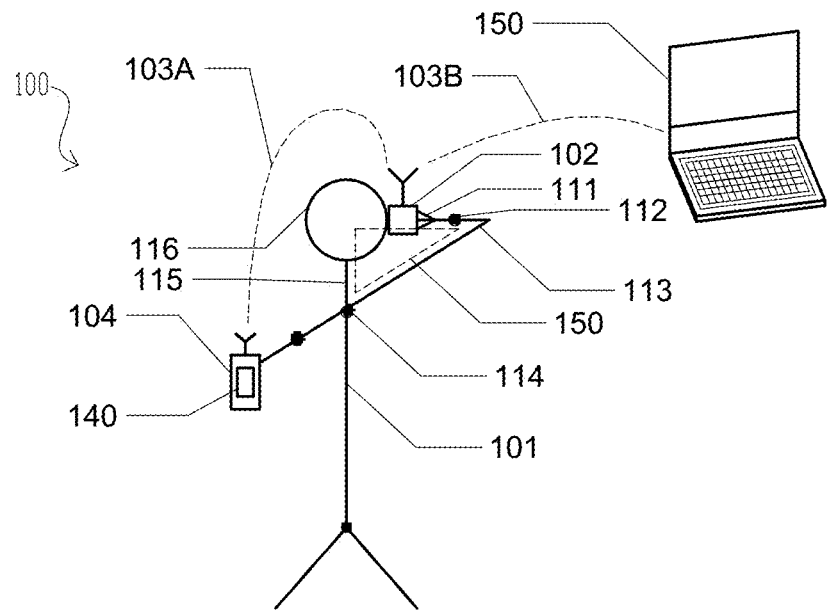
FIG. 1A is a diagram illustrating an exemplary vital signs scanning system with the scanner held at the forehead.

Many alternative embodiments of the present aspects may be appropriate and are contemplated, including as described in these detailed embodiments, though also including alternatives that may not be expressly shown or described herein but as obvious variants or obviously contemplated according to one of ordinary skill based on reviewing the totality of this disclosure in combination with other available information. For example, it is contemplated that features shown and described with respect to one or more particular embodiments may also be included in combination with another embodiment even though not expressly shown and described in that specific combination.

For purpose of efficiency, reference numbers may be repeated between the figures where they are intended to represent similar features between otherwise varied embodiments, though those features may also incorporate certain differences between embodiments if and to the extent specified as such or otherwise apparent to one of ordinary skill (such as differences clearly shown between them in the respective figures).

It is desirable for consumers to take greater control of their own basic health and work with their primary care providers (PCPs) to provide personalized healthcare. A vital signs scanner can be used to effortlessly scan a person's vital signs almost anytime and anywhere. A vital signs scanner can transfer the vital signs results to a portable wireless multifunction device, such as a smartphone, for storage and display to a user over time to illustrate health trends. The vital signs scanner allows consumers to take greater control of their own basic health and work with PCPs to provide personalized healthcare.

The vital signs scanner allows users to efficiently measure multiple vital signs simultaneously. Vital signs scanning with the vital signs scanner is quick and easy and very convenient in that it can simultaneously capture a plurality of vita signs data with one scanning session (one or two vital signs scans) at a given time and date. The vital signs data is transferred to a users own portable multifunction touch screen device, e.g. a smart phone. The portable multifunction device, with the assistance of vita signs scanning software, displays the scanning results in an intuitive user interface that is simple to understand.

The vital signs scanning device provides a method of vital signs scanning to help solve the missing information link so a user can take control of managing his/her own health. In addition to providing vital signs scanning, the vital signs scanner and system also stores the users vital signs measurements and trends over time of a day and date. The vital signs scanner and system provides easy access (almost anywhere at anytime) to important vital signs measurements such as blood oxygenation, blood pressure, heart rate, etc. The vital signs scanner and system can help share up-to-date vital signs data with a user's PCP for better diagnosis of medical conditions. Perhaps even more importantly, sharing of history and trends of vital signs data before and after an ailment with the user's PCP can provide clues to its cause and not just indicate the symptoms.

The personal wireless vital signs scanner combines aesthetic design with functionality. The personal wireless vital signs scanner is lightweight and easily fits into one hand. The personal wireless vital signs scanner can be held and operated with just two fingers of one hand. The user's other hand is free to hold a smartphone with a vital signs scanning application running to control the vital signs scanning process and view the scanning results. Vital signs data of a users body can change at different times of each day. The personal wireless vital signs scanner is so small, light, and esthetically pleasing that a user may desire to take it with them to perform a plurality of vital signs scans at different times throughout his/her day over a plurality of days.

A portable vital signs scanner and system may prove to be useful for healthcare professionals as well. For example, patients could scan for their own vital signs themselves in a busy hospital, clinic or doctors office, rather than wait in long lines just to get a simple checkup before seeing the doctor. The patients' scans are then uploaded to a server at the hospital, clinic, or office. With these self-obtained vital signs scans of patients being uploaded to a server, medical assistants and nurses, ordinarily checking for vital signs, can better spend their time curing the ailments of the patients.

The self-obtained vital signs scans of patients may also serve to triage the patients that are waiting for medical care. For example, a self-obtained vital signs scan of a patient indicating an elevated or irregular heart rate may signal hospital staff to attend to this patient immediately or at least a higher priority in a queue of patients. In this manner, the self-obtained vital signs scans of patients provide a clinic staff with a sense of the severity of the condition of patients waiting and can make appropriate schedule priority adjustments, if needed.

Measurements of vital signs from a vital signs scanner can be included as part of a user's personal medical record that the user maintains over his or her life. Further information about a vital signs scanner and vital signs scanning system is now provided.

Referring now to FIG. 1A, a diagram illustrating a vital signs scanning system 100 is shown. The scanning system 100 includes a portable wireless vital signs scanner 102 and a portable wireless multifunction device 104 in wireless communication with each other over a wireless communication channel 103A. The vital signs scanner 102 includes a plurality of sensors designed to read vital signs from a user's body 101. An instance or snap shot of vital signs, such as temperature, heart rate, blood oxygenation or SpO2, ECG (electrocardiogram), and possibly stress levels, all synchronously measured, can be reported to the device 104 by the scanner 102 in less than a minute. Exemplary methods and algorithms for determining one or more of these vital signs from the sensor data are described in International Application No. PCT/US2013/061046, filed by Scanadu Corporation on 19 Oct. 2012, having international publication no. WO 2013/066642, entitled AUTOMATED PERSONAL MEDICAL DIAGNOSTIC SYSTEM, METHOD, AND ARRANGEMENT, claiming priority to U.S. Paten No. 61/549,134 filed on 19 Oct. 2011, and is hereby incorporated by reference.

The algorithms and processes disclosed in International Application No. PCT/US2013/061046 are based upon one or more of the following references (all of which are incorporated herein in their entirety): Pulse transit time: an appraisal of potential clinical applications, Thorax 1999; 54:452-457 [doi:10.1136/thx.54.5.452] [http://thorax.bmj, com/content154/5/452.full]; U.S. Pat. Nos. 6,723,054; 6,527,728; U.S. Publication No. 2007/0276632; and U.S. Publication No. 2003/0199771; Severinghaus, John W., Honda Yoshiyuki (April 1987), "History of Blood Gas Analysis. VII. Pulse Oximetry", Journal of Clinical Monitoring # (2): 135-138; Millikan G. A. (1942). "The oximeter: an instrument for measuring continuously oxygen-saturation of arterial blood in man", Rev. Sci. Instrum 13 (10): 434-44 [doi:10.1063/1.1769941]; U.S. Pat. Nos. 6,385,471; 5,934,277; 5,503,148; 5,351,685; 5,259,381; 4,883,353; 4,824,242; 4,807,631; 4,796,636; 4,714,080; 4,623,248; and 4,266,554.

Integration of multiple sensors and scan quality algorithms make it possible to monitor the quality of the scanning process and then provide intuitive user feedback to control the interactive scanning process, to make a great user experience in the vital signs scanning process.

The wireless vital signs scanner 102 may perform vital signs scans and display the results in under a minute. Generally scans may be completed in approximately ten seconds. The length of a scanning session may depend on the users ability to correctly utilize the scanner 102. For example, if the user moves too much during the scanning session, the session will last longer as the device 104 prompts the user to remain still.

Different types of scans may also take different lengths of time. For example, in a standard ten-second scan where the scanner is held against a users forehead, temperature, 402, ECG, heart rate, blood pressure may be measured. For a 30 second extended head scan, vital signs such as blood pressure and heart rate variability (related to emotional stress) may be captured. For a thirty second scan from a users chest, respiration rate and body sounds may be measured or collected. In any case, the scanning sessions are still short and convenient.

Short scanning sessions have several advantages. A short scanning session allows a user to take a quick break from their daily activities to perform a scan anywhere and at any time. The ease and rapidness of performing a vital signs scan will encourage users to perform the scan multiple times a day, providing more complete and accurate trending data. The invention provides a consumer-oriented scanner that a user can use anytime anywhere to obtain multiple vital sign measurements in seconds.

Short scanning sessions also conserve power. With ten second scans, the scanner is designed to last for one week of normal usage with one full battery charge. If the power is on for a total of about 30 seconds for each scan, then total power-on time for each day is less than one hour with 100 scans per day. The scanner 102 may operate for a week at a time between battery recharging sessions.

Scanner 102 is an elegant consumer device that is portable. Unlike other vital sign monitors, scanner 102 does not need to be worn. Scanner 102 is perhaps the smallest consumer device that can measure multiple vital signs simultaneously. Measuring approximately 60 mm in diameter and 18 mm high, the scanner 102 can be easily places in a pocket or purse for use at any time convenient to the user. At any time the user has a moment to spare, the scanner 102 may be used to obtain multiple vital sign measurements by simply finger-holding it against the user's forehead.

Using a multifunction device 104 to display the vital signs scanning results allows the scanner 102 to maintain a compact size and minimalist form. Multifunction device 104 may be any portable wireless multifunction device such as a smartphone, tablet PC, or the so-called smart watches. Generally these devices are pre-owned and already available to the average consumer, so utilizing the display capabilities of multifunction device 104 does not detract from the portability of the invention. The ubiquity of smartphones also means that the average consumer does not need to pay more for a dedicated display device. Combining the vital signs scanner 102 with, a smartphone that a user already has, allows one to take control and greater responsibility for his/her health without sacrificing valuable time and money.

To display the vital signs scanning results, the portable wireless digital device 104 executes a vital signs scanning software application 140. The instructions of the vital signs scanning software application 140 are executable with the operating system, (e.g., Android and iOS), of the multifunction device 104. Once the software application is active, the user may power up the vital signs scanner 102. Upon power up, the vital signs scanner 102 is paired with the portable wireless digital device 104 to form the communication channel 103A between them. Accordingly, each of the scanner 102 and multifunction device 104 has a compatible wireless radio to form a compatible wireless communication channel. In one embodiment, the communication channel 103A is a Bluetooth version 4, a smart low energy (LE) supported channel that each wireless radio supports. The vital signs scanner 102 sends the vital sign information wirelessly to the portable wireless multifunction scanner 102 over the wireless communication channel 103A for storage and further analysis.

With the communication channel 103A available, the vital signs scanner 102 is pressed against a user's forehead. The forehead is identified as the single place with enough blood vessels and thin skin so that temperature, pulse oximetry and ECG can be obtained in sync and time-stamped. A scanning button is pressed on the user interface of the application 140 of the portable wireless multifunction device 104 to start the scanner 102 scanning for vital signs information of the user. After scanning for approximately 10 seconds or less, the vital signs scanner 102 sends the vital sign information wirelessly to the portable wireless multifunction device 102. The multifunction device 104 may display the results of the scan on a touchscreen display.

The vital signs scanner 102 is used periodically to scan for vital signs each day. Statistical information regarding a plurality of scans each day over a plurality of days can be generated and displayed on the touchscreen display device of the device 140. The vital signs scanning software application 140 informs a user of how those vital sign measurements may change during times of a day and over a plurality of days.

An important aspect of the invention is the quality of the scanning results. To optimize the scanning session results, the scanner 102 is designed to be easy to use to minimize user error. Similarly, the scanning software application is intuitive and easy to use. With minimal instruction, an average user can generate medical grade vital signs scans within minutes of using the invention for the first time.

To further optimize scanning results, scan quality algorithm monitor the vita signs scanning process and provides feedback (visual and/or audible) to the user through the multifunction device 104, and/or alternatively an optional sound generator (see audible sound generator 847 in FIGS. 8A-8B) in the scanner 102. The user feedback may help the user to perform a better vital signs scan with the wireless vital signs scanner and acquire good quality vital signs measurements.

Integration of multiple sensors allows for synergistic accuracy of vital signs scans. For example, integration of an accelerometer enables motion detection that is often associated with poor signals of pulse oximetry and ECG. In another example, abnormal signals of both pulse oximetry and ECG suggest the device is not held against the body properly. This can be further confirmed by comparing the surface temperature and ambient temperature of the sensor when not in touch with the user. Quality checking of individual vital sign measurements is based on fusion of multiple sensors, including a motion sensor, such as an accelerometer. Signal quality is checked based on dynamic range detection and thresh-holding. To make the process more robust, known signal processing techniques, such as envelope detection, can be applied to the raw signals from the sensors as a preprocessing step. Quality checking of raw sensor signals from the sensors makes sensor data fusion more robust by rejecting bad signals. Thus, fusing results of multiple sensors can provide better individual measurements of each vital sign.

The intuitive scanning user interface (UI) is designed, in combination with scan quality algorithms and the device's self-diagnostic capability, to help users to finish a vital signs scan successfully. There is the quality indicator from the quality algorithm, the progress bar, and texts that provides feedback to the user to ensure a successful scanning session. For example, suggestions to "hold still" or "hold device to your forehead" may prompt the user to correct his/her poor scanning behavior.

The scanning system 100 is user friendly so that it can be used multiple times during the day to obtain data about a users body 101. One person or one family can exclusively use the scanning system 100 and scanner 102 at home as a personal vital signs scanner. In this manner, a measure of one's personal health and medical data can be obtained right at home with the scanning system 100 without seeing a doctor or being admitted to a hospital. Each scan only lasts approximately ten to thirty seconds and obtains multiple vital sings measurements so users can take the scan repeatedly throughout the day without being inconvenienced.

The scanning system 100 can be used to personally analyze and track one's own vital signs to see various trends over time. Accordingly, the vital signs data can be accumulated over a plurality of days and a plurality of scans at various times each day, then stored in non-volatile manner with the device 104 so the data does not get lost. The vital signs data can also be backed up to a computer, a storage device, or storage server so it is not lost if the device 104 is lost or stolen. The storage server having greater storage may also be used to accumulate ones user data over a plurality of years when the device 104 is limited by its built-in storage capacity.

In operation, the vital signs scanning system 100 forms an electrical circuit 150 with the user's body 101. The circuit 150 is formed between first and second electrodes of the portable wireless vital signs scanner 102. From a first electrode of the scanner 102, the circuit 150 is made with the fingers 111, the hand 112, the arm 113, the chest 114, the neck 115, and the head 116 of the user's body 101 to a front electrode. Preferably, the portable wireless vital signs scanner 102 forms an electrical connection to the forehead portion of the head 116 of a users body 101. Fingers 111 not only serve to hold the scanner 102, but also as one contact point for one-lead ECG (the other one-lead ECG contact point is forehead). Preferably the thumb finger 111 in one embodiment and the index finger in another embodiment forms an electrical connection with the portable wireless vital signs scanner 102.

The vital signs scanning system 100 may optionally include a personal computer 150 in wireless communication with the portable wireless vital signs scanner 102 over an alternate or additional wireless communication channel 103B.

Figure 1B:
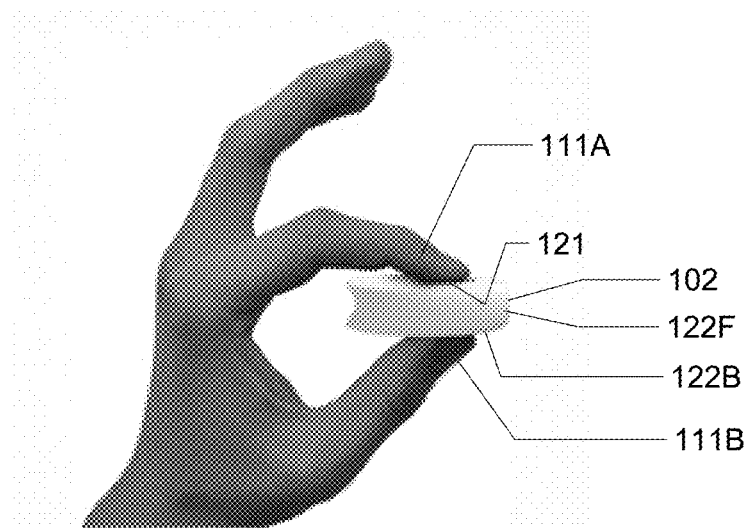
FIG. 1B is a perspective view of a user squeezing the exemplary vital signs scanner.

Referring now to FIG. 1B, a perspective view of a user's fingers 111A-111B squeezing the vital signs scanner 102 is shown. The vital signs scanner 102 is squeezed between the user's fingers to form at least one electrical connection. The front side sensors and a front electrode in the vital signs scanner 102 are then pressed against the user's forehead to form an addition electrical connection. The small size 60 mm×60 mm×18 mm allows the scanner 102 to be held by just two fingers of one hand. At a weight of approximately 60 g, the scanner 102 may be used by just about any person, from a child to the very elderly. Finger-held form-factor, ten to thirty seconds per scan, scan quality algorithm with feedback and an intuitive scanning user interface on a personal portable multifunction device, all help make vital signs scanning fast and easy while producing quality results.

Preferably, the scanner 102 is held between the thumb 111B and forefinger 111A of the user's left hand. The forefinger 111A may also rest over a sensor 121 and forms an electrical connection to an electrode around the sensor in one embodiment. In another embodiment, the thumb finger 111B makes contact with a bottom electrode 122B. The thumb of the left hand couples to the bottom electrical contact (electrode) on the bottom-housing portion of the scanner.

The forefinger makes contact with a rectangular glass plate over an oximeter sensor 121 in one embodiment. In another embodiment, the oximeter sensor 121 is moved to the front side of the vital signs scanner 102 so that extraneous light is less likely to interfere with the its readings.

A front side electrode 122F makes contact with the user's forehead or temple, when it is pressed up against his/her head. An infrared (IR) thermometer sensor is combined with the front side electrode 122F. The IR thermometer sensor makes temperature readings at the user's forehead. An oximeter sensor may also be located near the front side electrode 122F.

With the thumb finger 111B in contact with the bottom electrode 122B, a circuit may be formed through the finger and the hand of the user and a portion of his body back to the front side electrode 122F in the vital signs scanner 102. Once proper placement of scanner 102 is made, a scan button is selected in the software application 140 of the device 104 to command the scanner to scan the vital signs from the user's body and forward them to multifunction device 104.

Figure 1C:
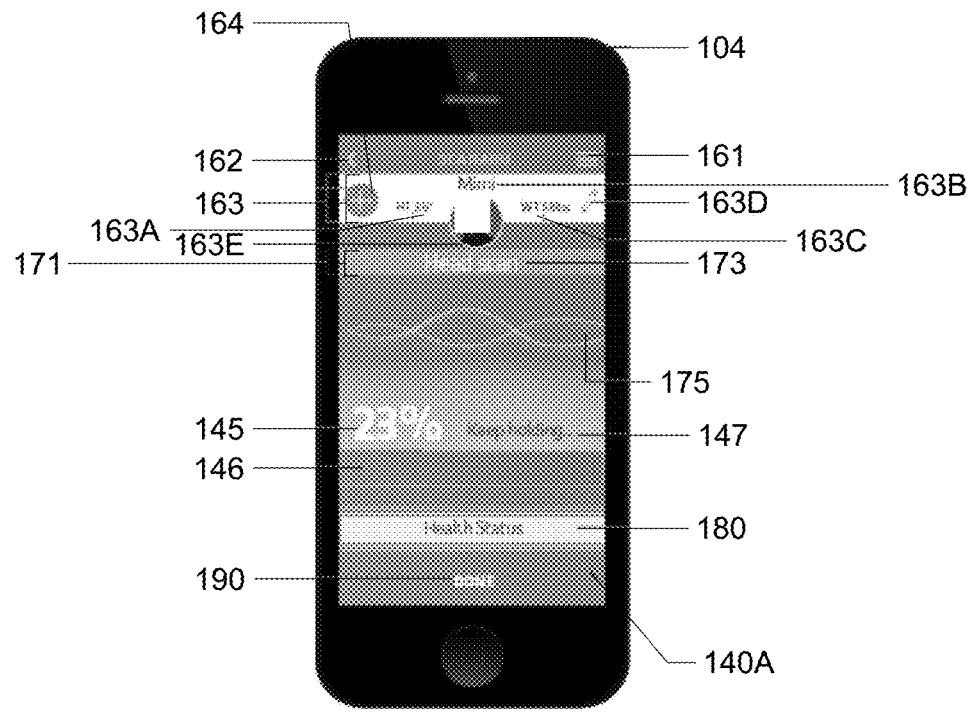
FIG. 1C is a diagram illustrating a portable wireless multifunctional device with a scan screen of vital signs scanning user interface.

Referring now to FIG. 1C, an exemplary initial scan screen window 140A of the vital signs scanning application 140 is illustrated. The initial window 140A includes an instruction scan messaging 147 with instruction scan message text and optionally an instruction figure to show the user how the vital signs scanner 102 is utilized. As indicated by the instruction scan message, the user is to keep holding the scanner to the user's left temple for the best scan.

The initial window 140A further includes a menu button 161, a back button 162, an edit button 163D, a tag information button 164, a health status button 180, and a done button 190. The tag information button 164 is used to add user information as well as tag scans with the circumstances under which a scan was undertaken, such as after eating or after exercise. The initial window 140A includes a user information bar 163 including information regarding a user's height, user's name 163B, users weight 163C, and a user's profile picture 163E. In this manner, the user is clear as to whom is logged into the vital signs scanner user interface and for who's body is to be scanned. The initial window 140A further includes a scan type indicator 173, indicating a head scan type 173A or a chest scan type 173B. The initial window 140A further includes a scan quality indicator 175, a scan progress bar 146, and a scan progress percentage indicator 146. The scan quality indicator is one form of quality feedback that may be employed by the scanning system to inform and train the user to acquire better scan data. The initial window 140A further includes a scant type slider 171 to select the type of scan that is to be performed. The menu button 161 can take the user to the next screen or a different screen within the vital signs scanning user interface. The edit button 163D can edit information and select options that are available in the vital signs scanning application 140.

The vital signs scanning application 140 may include an option to enter the users symptoms by selecting the health status button 180. A photo may also be taken of the medical condition of a user by use of a camera in the device 104 and a photo button. Additionally, a user may add a note to his health status using the device 104 and an add note button.

The status of the scanner 102, such as powered on/off, blue tooth connection, battery charge status, and/or ready to scan, may also be displayed in one or more of the user interface windows.

The scanner 102 can collect a diverse set of physiological information (e.g., vital signs) during one or two acquisition periods totaling approximately sixty seconds (head scan, extended head scan, and/or chest scan).

Figure 1D:
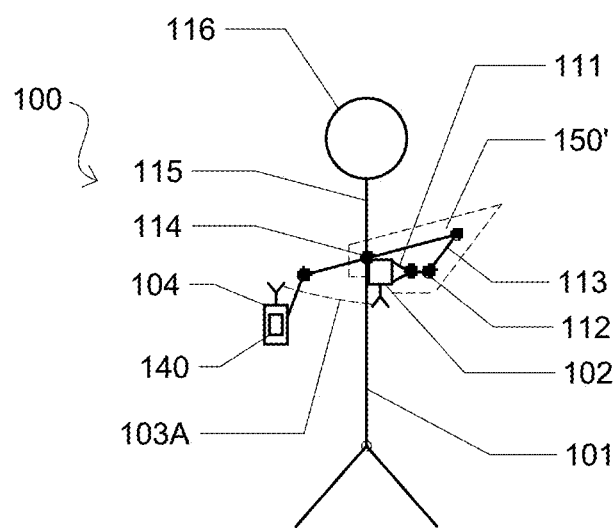
FIG. 1D is another diagram illustrating an exemplary vital signs scanning system with the scanner held at a chest position.

Referring now to FIG. 1D, a diagram of an exemplary vital signs scanning system with the scanner held at the chest position is illustrated. In this embodiment, vital signs are first acquired from a first 10-second scan at the forehead as shown in FIG. 1A. Vital signs may the further be acquired by secondary scans such as a longer or extended scan at the forehead as shown in FIG. 1A, and then a subsequent scan conducted near the chest of the user as shown in FIG. 1D.

A secondary extended scan at the forehead may be over a range of time from about thirty seconds up to a minute so that measures of heart rate variability and respiration rate may be obtained. The secondary extend scan at the forehead can also provide for a more robust and accurate measurement of blood pressure. In terms of using the scanner, the primary and secondary scans at the forehead may occur in one single scan (e.g., 10-second or 30-second) or two separate scans (e.g., a first at 10 seconds and then a second at 30 seconds).

The secondary extended scan near the chest, a chest scan, is mainly to capture vital signs of respiration rate and additional physiological information from the captured body sounds. The vital signs scanned at the chest area may also include heart rate variability. The secondary extended scan near the chest may last for a period from thirty seconds to a minute. The vital signs scanning application executed on the multifunction device 104 may prompt the user for one or both scan locations.

The secondary chest scan can be selected by the scan type slider 171 shown in FIG. 1O. A second or third scan may be selected with a finger swipe to perform the second scan or the third scan at the chest of the user. If only the first head scan was desired, a done button 190 may be selected to avoid the secondary scans. This may be because its inconvenient due to timing or to perform against ones chest with the vital signs scanner, such as when it is inconvenient to do so in public.

Figure 1E:
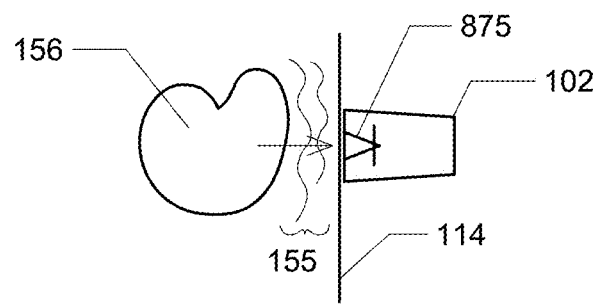
FIGS. 1E-1F are diagrams illustrating how microphones of the exemplary vital signs scanner can capture body sounds, such as from a users heart or lung.
Figure 1F:
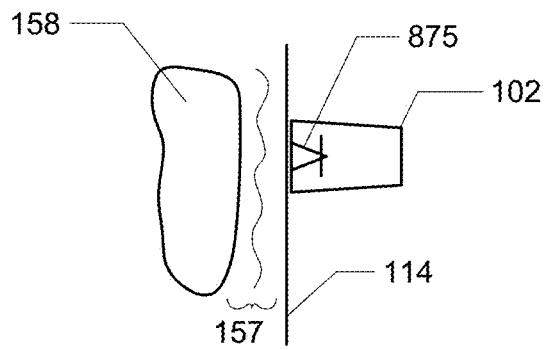

As mentioned herein, a chest scan may be performed with the scanner 102 as shown by FIGS. 1D, 1E, and 1F, for example. In FIG. 1D, a second circuit 150' may be formed with the users body 101 between the electrodes of the scanner 102. The second circuit 150' in this case includes the chest 114, the arm 113, the hand 112, and the finger 111 of the user.

Figure 1G:
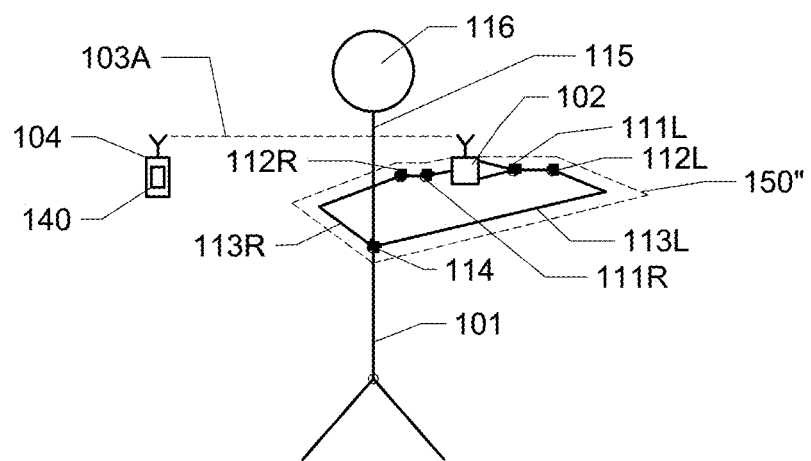
FIG. 1G is another diagram illustrating an exemplary vital signs scanning system with the scanner held in fingers of each hand.

In an alternate embodiment, another circuit 150" may be formed with the users body between the electrodes of the scanner 102 while the device 104 is nearby. This alternate circuit 150" is formed by fingers on different hands coupling to the electrodes of the scanner 102. A left finger 111L may couple to a bottom or top electrode in the scanner 102. A right finger 111R may be coupled to the front electrode of the scanner 102. From a left finger 111L in a left hand 112L of the user, the circuit in the body includes, the left finger 111L, the left hand 112L, the left arm 113L, the chest 114, the right arm 113R, the right hand 112R, and a right finger 111R, such as shown in FIG. 1G, to complete a circuit with the scanner 102.

In either case, the ECG circuitry in the scanner 102 may then obtain further data regarding heart activity of the user that can be combined/fused with the heart activity data of a first scan, to improve the measure of vital signs of heart activity. The vital sign measures of heart activity may then be sent to the device 104 for display to the user on its built-in touchscreen display.

Temperature of the body adjacent the user's chest 114, if reliable, may also be used by the scanner to improve scanning results of temperature. Temperature at the users finger 111R, if reliable, may also be used by the scanner to improve scanning results of temperature.

With the scanner against the users chest, an accelerometer (see accelerometer 885 in FIGS. 8A-8B) in the scanner 102 may be used to capture movement of the chest as a measure of respiration rate. The vital signs data from these measures are computed by the processor 840 and then sent to the device 140.

FIGS. 1E and 1F illustrate the use of the microphones in the scanner 102 to capture body sounds around the chest, such as heart sounds and lung or breathing sounds. These body sounds may be recorded to capture another symptom of a user's medical condition. Body sounds that are captured may also be used to judge the quality of the vital signs scanning process. The recorded body sounds may be stored locally in the memory of the scanner and/or sent to the device 140 for storage with the vital signs data of the same time and date.

Figure 2A:
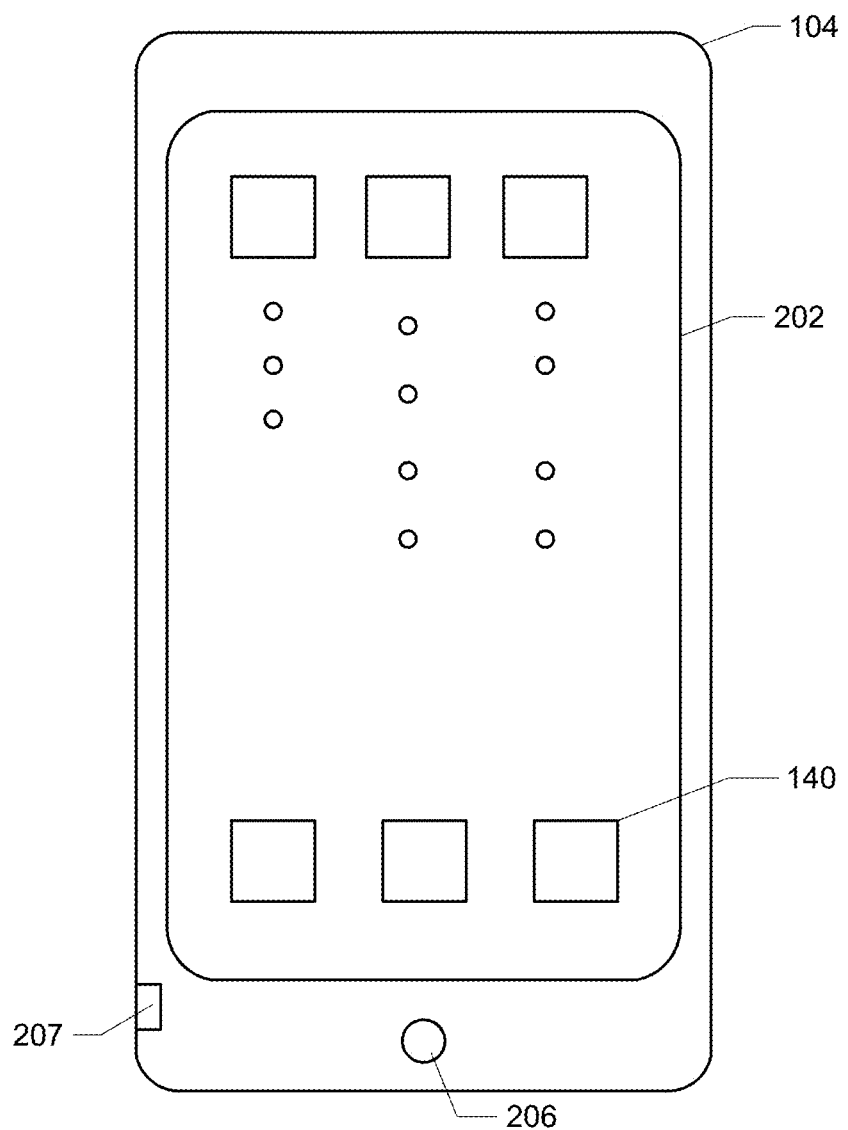
FIG. 2A illustrates an exemplary portable wireless multifunction device to execute the vital signs scanning application.

Referring now to FIG. 2A, a portable wireless multifunction device 104 is illustrated that can execute the vital signs scanning application 140. The portable wireless multifunction device 104 includes a text screen 202, at least one function button 206, and a power button or switch 207. The multifunction device 104 may display a plurality of application icons on the touch screen 202. One of these icons may be the vital signs scanning application software icon 140.

Figure 2B:
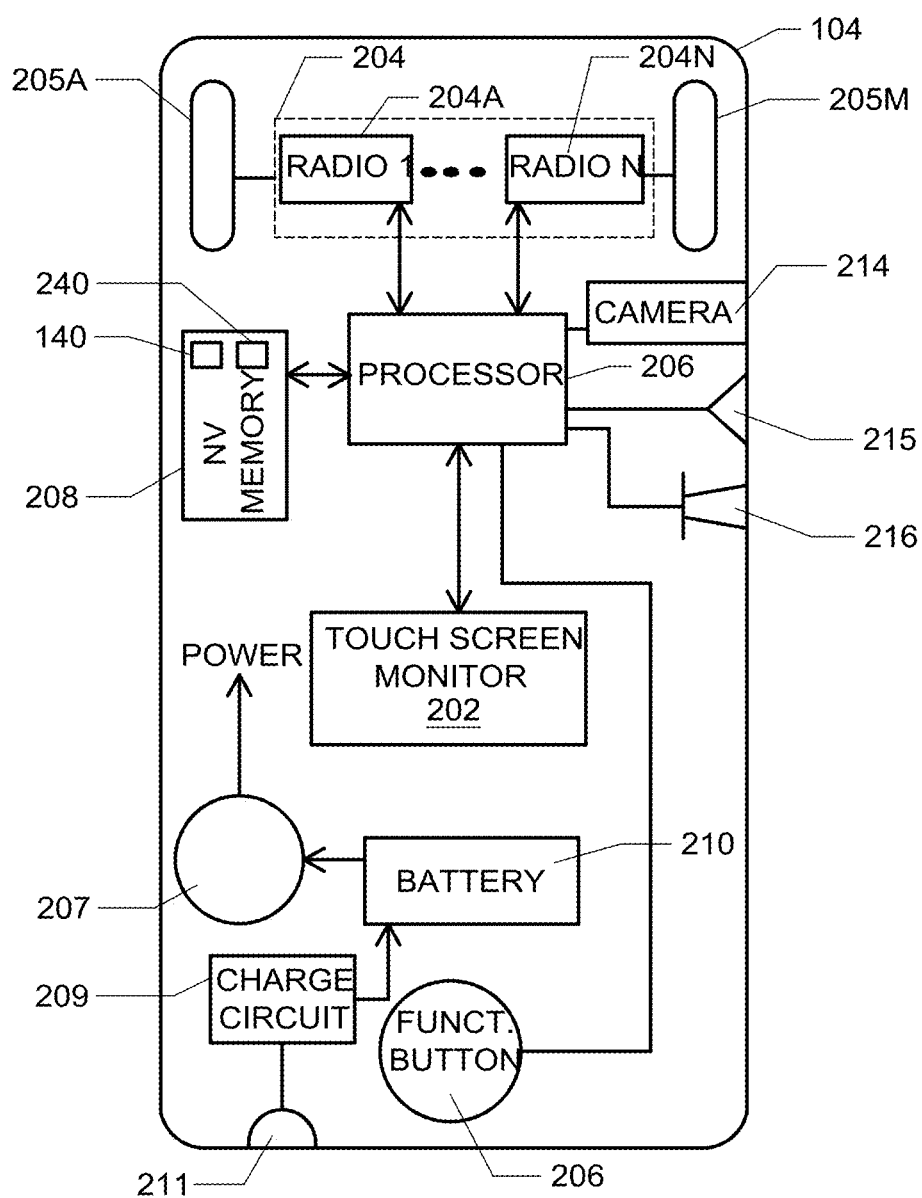
FIG. 2B illustrates a schematic representation of the components of the portable wireless multifunctional device.

Referring now to FIG. 2B, a block diagram of the personal wireless digital device 104 is illustrated. The portable wireless multifunction device 104 may be a smart phone, a tablet computer, a portable music player, or a wireless portable storage device, for example, that include a processor, a touch screen, and a memory from which application software instructions may be executed.

As shown in FIG. 2B, the portable wireless multifunction device 104 includes a touch screen monitor 202, one or more wireless radio transmitters-receivers (wireless radios) 204A-204M coupled to their respective antenna 205A-205M, a processor 206, non-volatile memory 208, at least one function button 206, and a cover button 207 that can switch power on to each electronic circuit within the portable wireless multifunction device 104. At least one of the wireless radios 204A-204M are compatible with the wireless radio in the wireless vital signs scanner 102.

The portable wireless multifunction device 104 may further include a camera 214, a microphone 215, and a speaker 216 coupled to the processor 206 as shown. Furthermore the portable wireless digital device includes a battery 210 coupled to the power button 207. Typically the battery 210 is a rechargeable battery such that an external power source may be coupled thereto via an external power connector 211 and a charge circuit 209.

Figure 10:
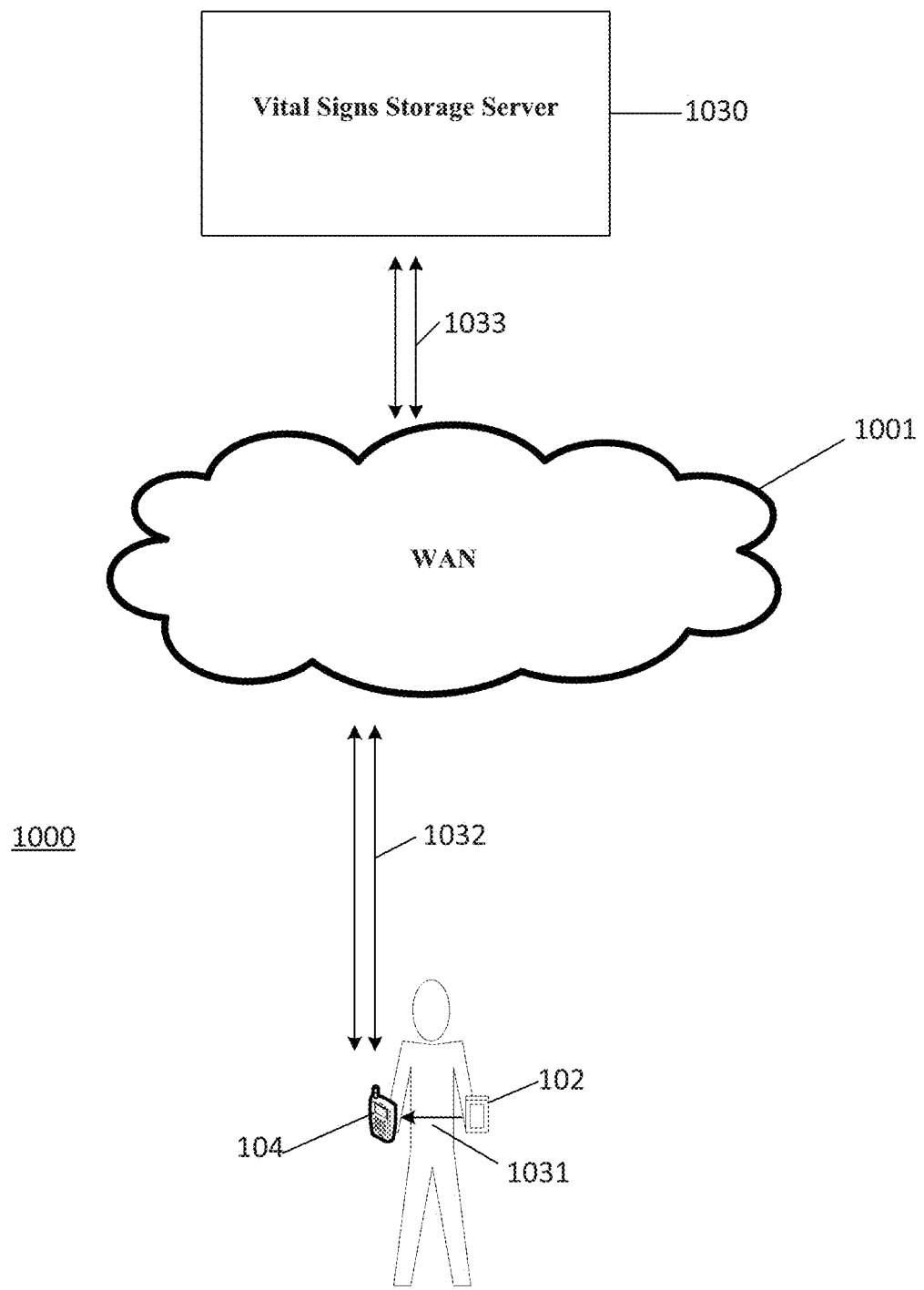
FIG. 10 is a block diagram illustrating an exemplary vital signs cloud system.

Non-volatile memory 208 of the personal wireless digital device may store the vital signs scanning application software 140 and data 220 related to the vital signs scan application software. The processor 206 can read and write to the non-volatile memory such that the vital signs scanning application software can provide a user interface to a user via the touch screen display device 202. As discussed previously, the initial vital sign scanning window 140I may be provided as shown in FIG. 10.

The camera 214 of the portable wireless digital device 104 may take photographs of a user's conditions or symptoms via the photograph entry button 175 of the user interface. The photographs may be stored as part of the data 240 in the non-volatile memory. The microphone 215 in the portable wireless multifunction device 104 may optionally be used to capture body sounds similar to the microphones in the scanner 102, as is shown in FIGS. 1E-1F.

The speaker 216 of the portable wireless digital device 104 may optionally be used to provide audible user feedback to the user of the vital signs scanner 102 to improve the vital signs scan quality as is discussed herein.

Figure 3A:
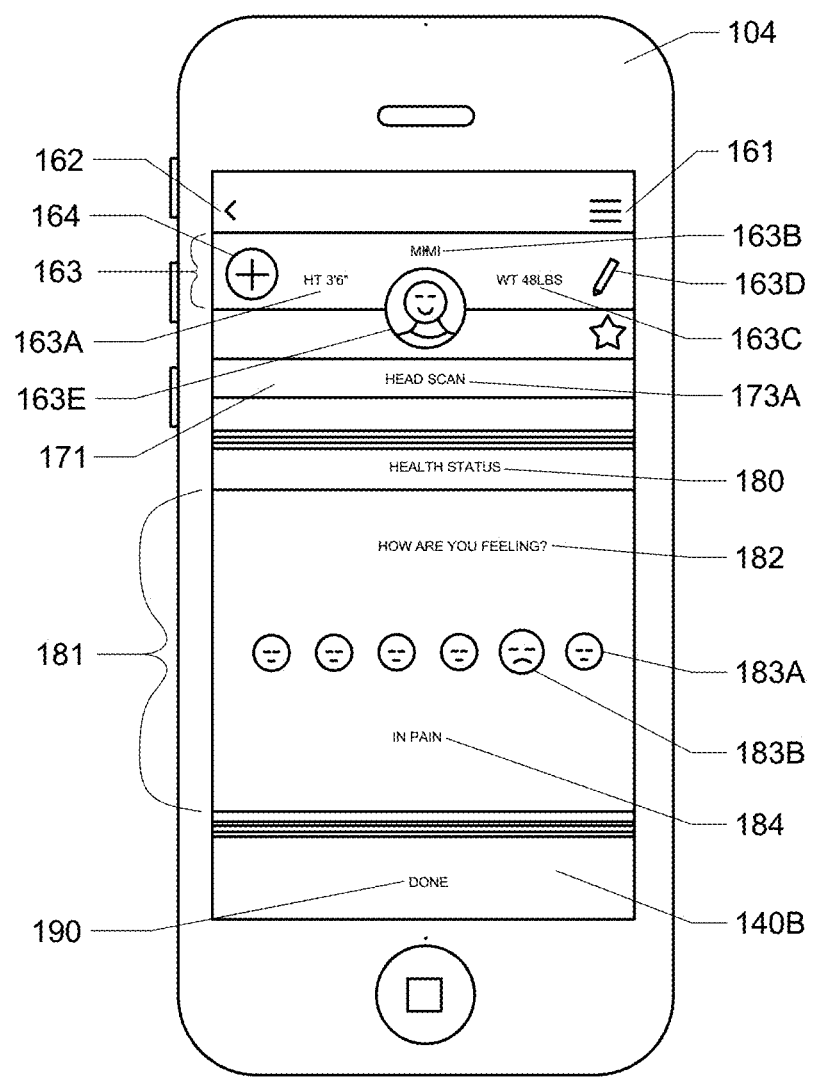
FIG. 3A is an exemplary health status window displayed on the portable wireless multifunctional device by the vital signs scanning user interface (VSUI).

Referring now to FIG. 3A, an exemplary scanning window 140A is shown being displayed by the touch screen display device 202 of the portable wireless multi-function device 104. The scanning application software 140 generates the various images consisting of a scanning progress bar 310, a scanning icon 312, a first vital signs graph 314A, a second vital signs graph 314B, one or more result buttons 320, and one or more status icons 324.

The status icon 324 may be a wireless connection status icon indicating that the portable wireless digital device 104 is connected to the vital signs scanner 102. The button 320 may be a results button to which to switch to another scanning window/screen of a user interface provided by the scanning application software 140. The scanning icon 312 may include the plurality of color bars 312A-312E that randomly vary in color and length to indicate that scanning is occurring. The scanning progress bar 310 illustrates the progress of the scanning session being performed by the portable wireless vital signs scanner 102. In this case data is being sent from the scanner 102 to the portable wireless multifunction device 104.

Briefly referring back to FIG. 1C, the initial window 140A includes a user menu button 161 that may be used to display a users menu on how to operate the vital signs scanner. The initial window 140A may further be changed to a graph window to show plots of prior scan data stored in the device 104. A graph button may be provided to do so or a finger swipe may be used.

Figure 4A:
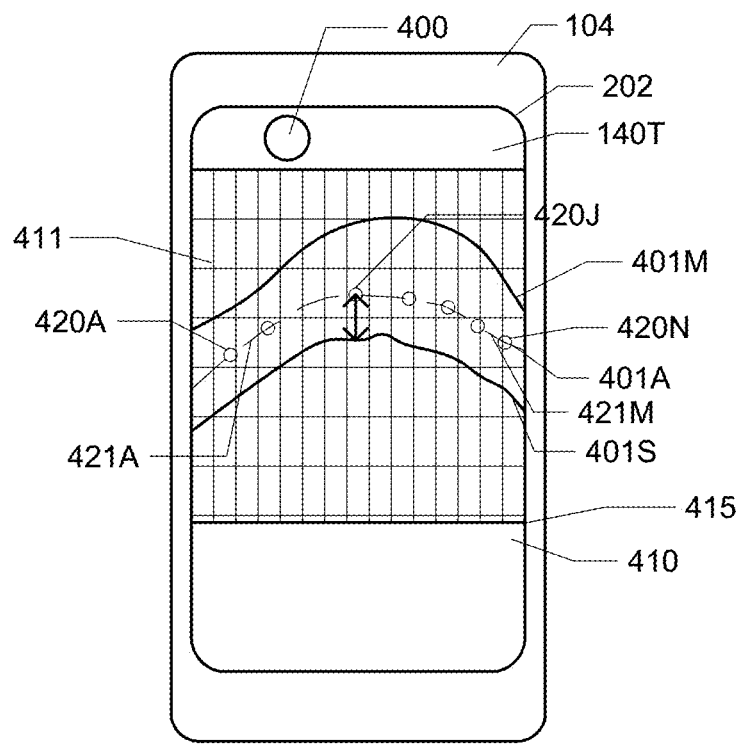
FIGS. 4A-4B illustrate a temperature averaging window generated in a touch screen of the portable wireless multifunction device by the vital signs scanning software application.
Figure 4B:
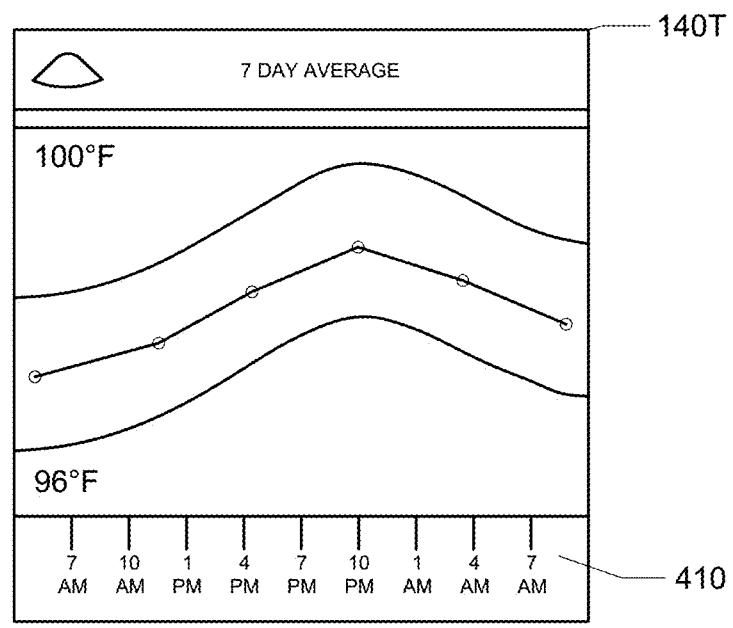

The first vital signs can be displayed in graph form over different day granularity such as 1 day, 1 week, 1 month, 3 months, 9 months and 1 year, such as the one week (7 day) graph illustrated in FIG. 4B. Graphs may be used to illustrate show the user's heart rate or heart rate variability. The waveforms displayed in the graphs are captured by the scanning process of the portable wireless vital signs scanner 102. A second vital signs graph may be oxygenation graph related to photoelectric plethysmogram (PPG) from the data obtained by the pulse oximeter. The scanner captures a user's blood volume pulse of both oxygenated and deoxygenated blood. From the photoplesmography waveforms (oxygenated and deoxygenated) a user's oxygen saturation can be obtained and displayed in the oxygenation graph.

Referring now to FIG. 3A, a health status window/screen 140B of the user interface software 140 is shown being displayed by the touch screen display device 202 of the device 104. The screen 140B includes a number of similar items illustrated in screen 140A of FIG. 1B and are not repeated here. The health status slider window/screen 140B (it can be slid sideways) includes a health status button 180, a health status window 181. The health status slider window 181 includes a display of a health status question 182 to obtain further information from a user. To respond, the health status slider window 181 includes a plurality of selectable health status response indicators 183A. The user selects one which becomes highlighted over the others, such as health status response selected icon 183B. The health status slider window 181 further includes a health status selected response information 184, such as "In Pain", that is displayed to the user to confirm the selected health status response.

Figure 3B:
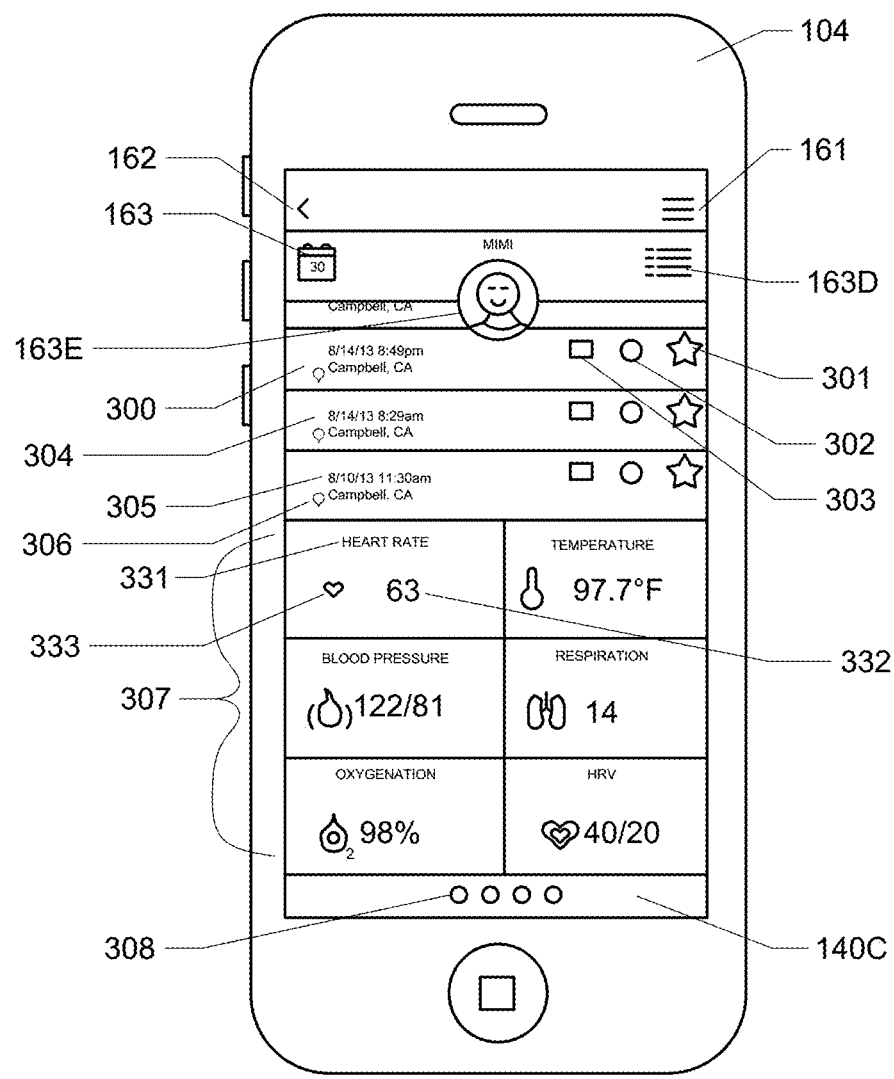
FIG. 3B is an exemplary scan results window displayed on the portable wireless multifunctional device by the vital signs scanning user interface.

Referring now to FIG. 3B, a scanning results window/screen 140C is shown being displayed by the touch screen display device 202 of the device 104. The screen 140B includes a number of similar items illustrated in screen 140A of FIG. 10 and are not repeated here. The exemplary scanning results window 140C may be generated by the user after selecting a results button under the menu button or by one or more sliding finger gestures (e.g., down and to the right).

The scanning results window 140C includes a results filter button 163D, and a calendar button 163. The scanning results window 140C displays one or more scanning sessions 300 each including a completed scan type indicator 301, an interpretive message indicator 302, a picture tag indicator 303, a date/time stamp 305, and a location time stamp 306. The scanning session that is selected for display on the device 104 is highlighted by a selected scan indicator 304. The scanning results window 140C further displays a results information slider window 307 and slider number indicators 308.

Figure 3C:
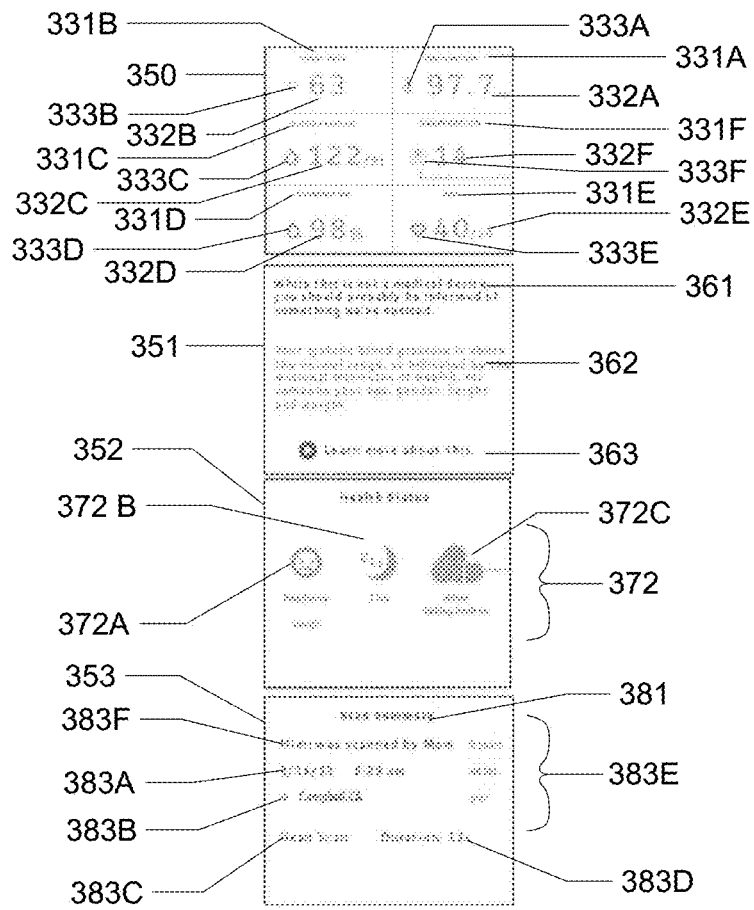
FIG. 3C illustrates exemplary slide windows generated on the portable wireless multifunctional device by the vital signs scanning user interface.

Referring now to FIGS. 3B-30, the results information slider window 307 can be slid sideways by a users finger to display different slides. As shown in FIG. 3C, the different slides include a vital sign measurements results slide 310, an interpretive message slide 311, a health status report slide 312, and a scan summary information slide 313.

The vital sign measurements results slide 310 includes a plurality of vital signs icons 333, a plurality of associated vital measurements 332), and a plurality of associated vital measured labels 331. The vital measured labels 331 indicated may be heart rate, breathing rate, temperature, blood pressure, and oxygenation. The associated vital signs icons 333 may be a heart icon, a breathing icon, a thermometer icon, a blood pressure icon and an oxygenation icon respectively.

The actual measurements captured during the scanning process are illustrated by the numeric number values of the vital sign measurements 332. For example, the heart rate of 63 is shown near the heart icon and the heart rate text. The numeric values of the vital measurements 332 may be the average measurements captured during the scan that was immediately performed recently or that scan session is selected by the user. The measurements 332 are illustrated near their respective icons 333 and the respective text label 331 indicating the vital sign that was measured. The results of the scan are typically automatically saved. However, a function button may be required to delete those scan results from the wireless portable multi-function device 104 or alternately a button to upload those results to a storage server.

The interpretive message slide 311 includes a medical information disclaimer 311A, a medical interpretive message 311B, and a learn more link 3110. The medical disclaimer message slide 311A may include a message such as "while this is not a medical device, you should probably be informed of something we've noticed". The medical interpreter message slide 311B may be something such as "your systolic blood pressure is above the normal range, as indicated by the National Institutes of Health, for someone your age, gender, height and weight." The learn more link 311C may include a selectable icon or text to transfer the user to a web browser and a health link where he may learn more about his or her condition.

The health status report slide 312, includes health status response buttons 312 A. Health status response buttons 312A may include a headache, a cough, indication of taking medication a sleeping response button including number of hours of sleep.

The scan summary information slide 313 includes a scan summary of a selected scan session. The scan summary may include the time and date stamp, the location of the scan, the type of scan (e.g., head or chest), and the duration of the scan, such as 13 seconds. The scan summary may further indicate the age, weight, and height of the user being scanned as well as whom performed the scan. In the example illustrated, the user Mimi was scanned by her Mom.

Figure 3D:
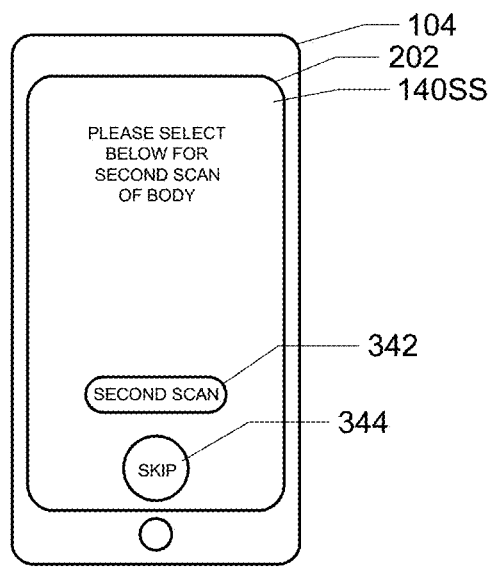
FIG. 3D illustrates an exemplary second scan selection window of the vital signs scanning application on the portable wireless device.

FIG. 3D is an illustration of an exemplary window of the vital signs scanning application on the portable wireless device. In this exemplary window displayed on touch screen 202 of the multifunction device 104, the vital signs scanning application 140 is prompting the user to select a second scan. A second scan may be selected by touching scan virtual button 342 or using a finger gesture on the touch screen. A third scan may also be selected after the second by touching scan virtual button 342 or using a finger gesture on the touch screen. The third scan may be performed at the chest region to measure respiration rate and collect body sounds. The user may desire to skip a secondary scan by touching a skip scan virtual button 344.

Referring now to FIGS. 4A-4B, a temperature averaging window 140C is shown being illustrated in the touch screen 202 by the scanning application software 140. This may be displayed as a result of selecting the graph button 165 of the initial scanning window 140I. The temperature averaging window 140C could include a textual heading 400 illustrating the types of graph that are plotted below. The textual heading 400 may recite "seven-day average" to let a user know that one or more seven-day average graphs are being displayed below. The portable vital signs scanner 102 may be used periodically throughout a 24-hour period each day. The seven day average may look back over a seven day window and time, plotting an average curve 401A, a maximum curve 401M, and a minimum curve 401S. The vital sign measurements are plotted on the Y-axis 411 and a time as the time of day on the X-axis 410. The portable wireless vital signs scanner 102 is expected to be used daily at multiple times during a day. In this, manner the vital signs of the user are captured periodically during the day by the vital signs scanner 102 and the personal portable wireless device 104 of the scanning system 100. The maximum curve 401M and the minimum curve 401S may be illustrating plots of the maximum value and minimum values over all scans that were previously performed. The time of day axis 410 illustrates periodic time values during the span of a 24-hour day. In one embodiment, the far most right point of the curves represents the given time of day 415 of a sliding window. In another embodiment, the time axis is fixed and the curve 401A grows from left to right during the time period as scans are made and time actually progresses. The scan points 420A-420M are illustrated along the average curve 401A. The scan points 420A-420M may represent actual scans during the day or some measure of average during the preceding seven-day period. Interpolation lines 421A-421M may be inserted between each scan point to show a trend line of how the vital sign that is measured varies during times of the day. For example, scanning point 420J may represent a scan that took place between 4:00 and 7:00 pm and how the body trends towards that during that time of day.

The illustrated seven day average graph illustrated in FIG. 4 shows a body temperature graph. This is for illustration purposes only. The vital sign measurement curves could be temperature curves, blood pressure curves, oxygenation curves, heart rate curves, breathing/respiration rate curves, for example, that represent measurements that are scanned by the vital signs scanner 102.

As more information is captured by the scanner 102 and stored in the personal portable multi-function device 104, additional results may be plotted over time to generate the curves for display by an averaging window, such as vital signs window 140C.

Figure 5A:
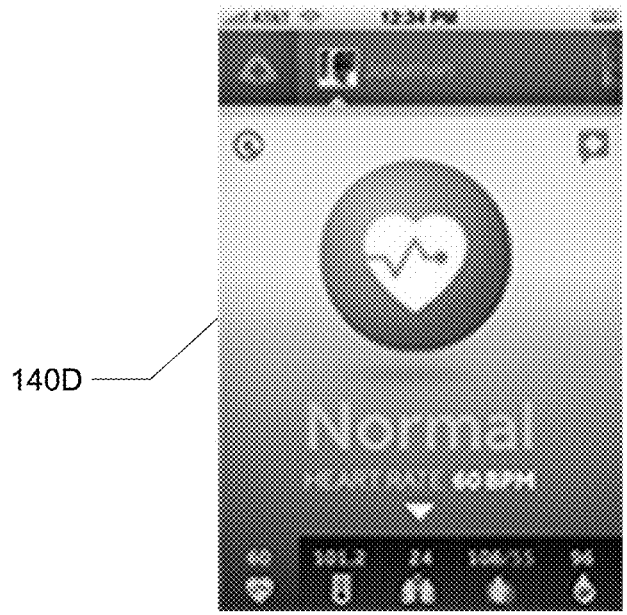
FIGS. 5A-5E illustrate prognosis windows for vital signs in a touch screen of the portable wireless multifunction device.
Figure 5B:
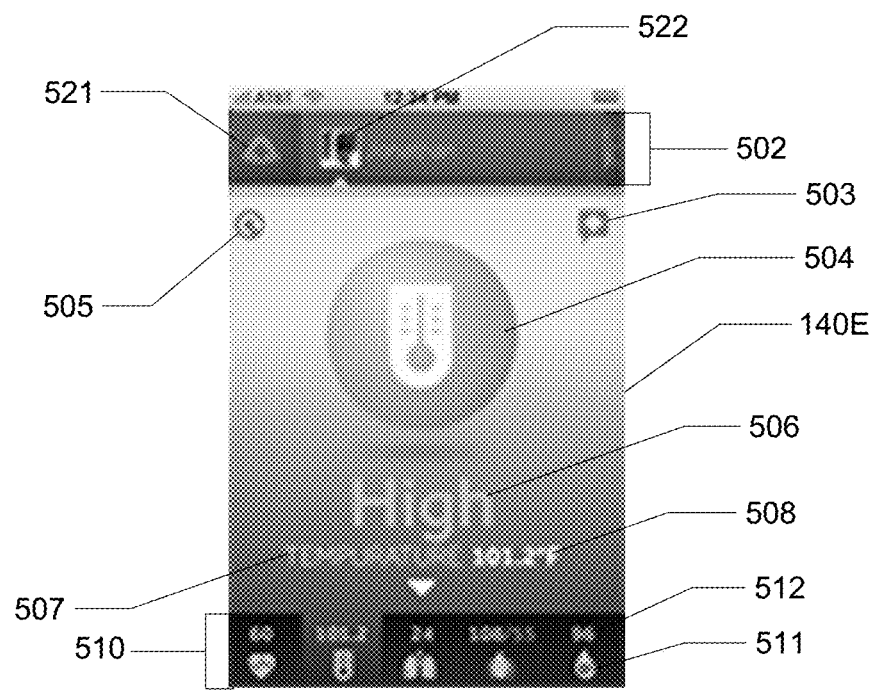
Figure 5C:
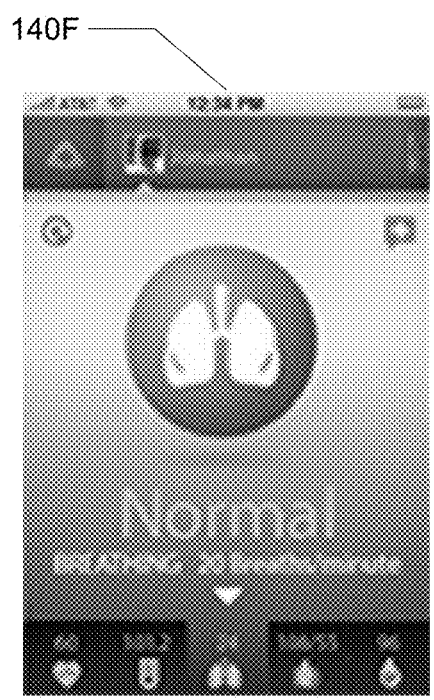
Figure 5D:
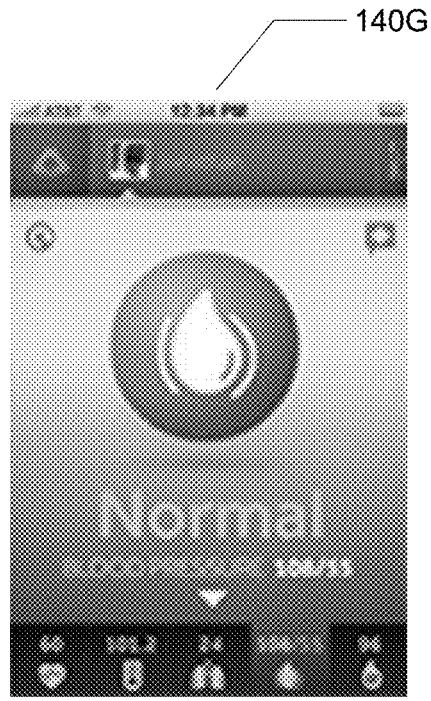
Figure 5E:
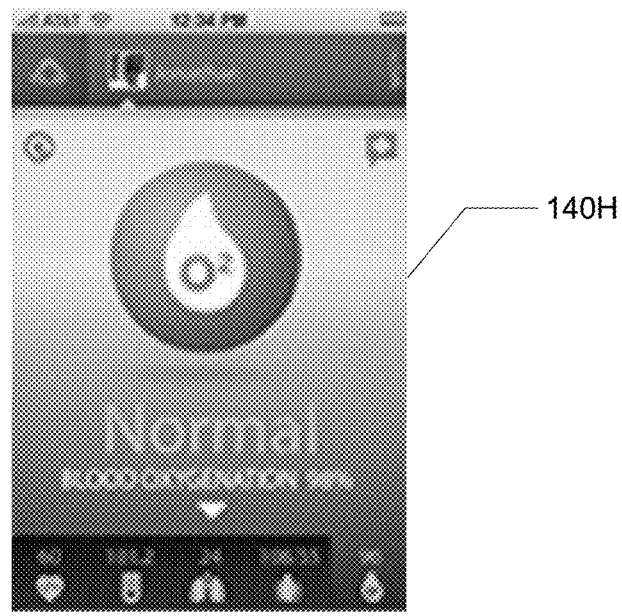

Referring now to FIG. 5A-5E, a plurality of prognosis windows 140D-140H are illustrated. In FIG. 5A, the heart rate prognosis window is shown. In FIG. 5B, the temperature prognosis window 140E is illustrated. In FIG. 5C, a breathing rate prognosis window 140F is illustrated. In FIG. 5D, a blood pressure prognosis window 140G is illustrated. In FIG. 5E, a blood oxygenation window 140H is illustrated. These windows may be selected through the use of the vital signs icons 333A-333E acting as buttons to display the respective prognosis window.

As illustrated in FIG. 5B, each prognosis screen 140D-140H, may include a navigation bar 502, one or more function buttons 503, a vital signs icon 504, a return button 505, a conditions indictor 506, a vital signs indicator 507, a measurements value indication 508, and a vital signs bar 510. The navigation bar 502 may allow a user to navigate the various screens of the vital signs application scanning software 140. For example, a scan screen icon/button 521 may be provided to jump to the scanning screen. A prognosis screen icon/button 522 may be provided to jump to the prognosis screens 140D-140H.

The vital signs bar 510 may be provided to navigate through the various vital signs prognosis windows/screens 140D-140H as well as providing a snapshot of the values of each of the vital sign measurements. In that case the vital signs bar 510 includes a measurement value indicator 512 and a vital signs icon 511 for each of the vital signs that are scanned and captured by the vital signs scanning system 100.

The return button 505 may be used to return to the previous screen that was displayed by the user interface of the scanning application software 140. The function button 503 may be an add a note button to add text about a users condition or circumstances under which a scan was taken. The vital signs icon 504 indicates at a glance what prognosis window is being displayed.

The conditions indictor 506 for each prognosis screen will provide an indication of the most recent scan in comparison with an expected average value for a given user. For example, a temperature's vital sign is illustrated in FIG. 5B as having the condition indication of high due to a measured value of 101° F.

In the vital signs bar 510 the measurement indicator 512 and the vital signs icon 511 may be highlighted to indicate which prognosis screen is being illustrated at a glance.

Figure 6A:
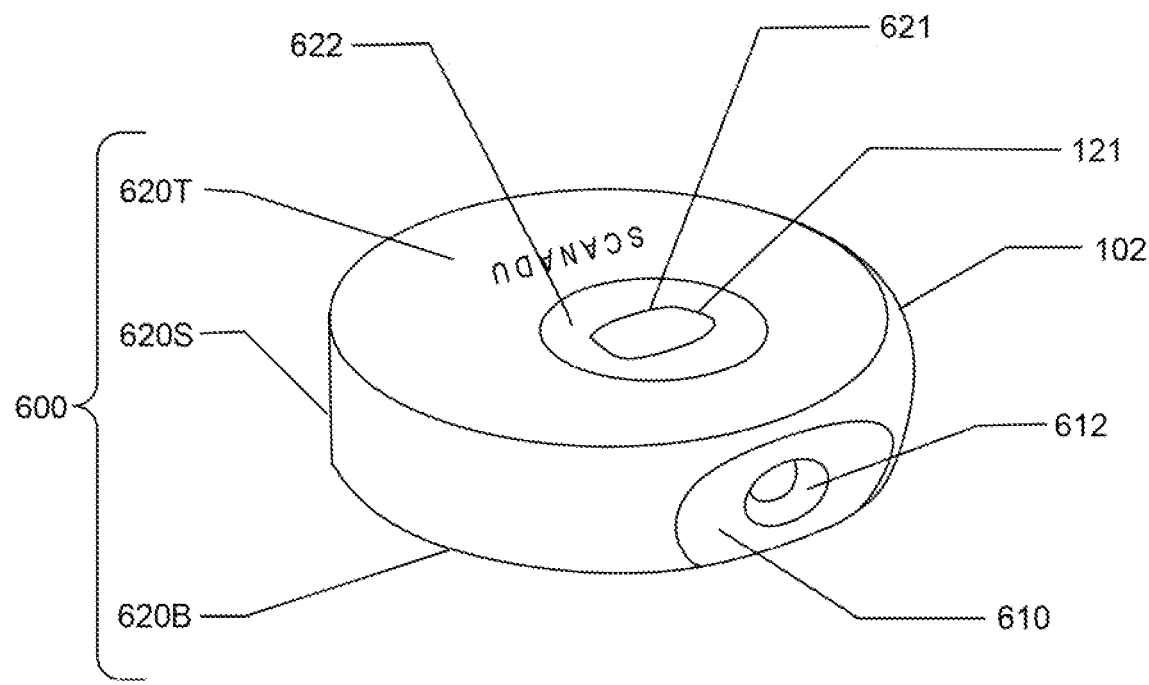
FIGS. 6A-6B are perspective views of an embodiment of the invention.

Referring now to FIG. 6A-6D, respective use of the portable wireless vital signs scanner 102 are illustrated. In FIG. 6A, a top front perspective view, the wireless vital signs scanner 102 includes a front electrode 610, and a front sensor 612 on a front side. The front electrode 610 is pressed against the user's forehead, preferably at the temple, in order for the scanner 102 to make an electrical connection to the body of the user.

In one embodiment the scanner 102, a top sensor window 621 and a top electrode 622 are provided in the topside of the scanner 102. A top sensor 121 may be located underneath the top sensor window 621 to obtain a vital signs measurement from a users finger that may be pressed on top of the window 621. A top electrode 622 may be used to form an electrical connection to a user's finger and complete a circuit of the users body such as illustrated in FIG. 1A.

The housing 600 of the vital signs scanner 102 may generally be circular shaped and include a circular top housing 620G, a circular bottom housing 620B, and a hollow cylindrical surface 620S. The side cylindrical ring 620S may be concave, or convex over a portion of the surface. Alternatively, the cylinder side surface 620S may be a toroid shape over a portion of its body.

Figure 6B:
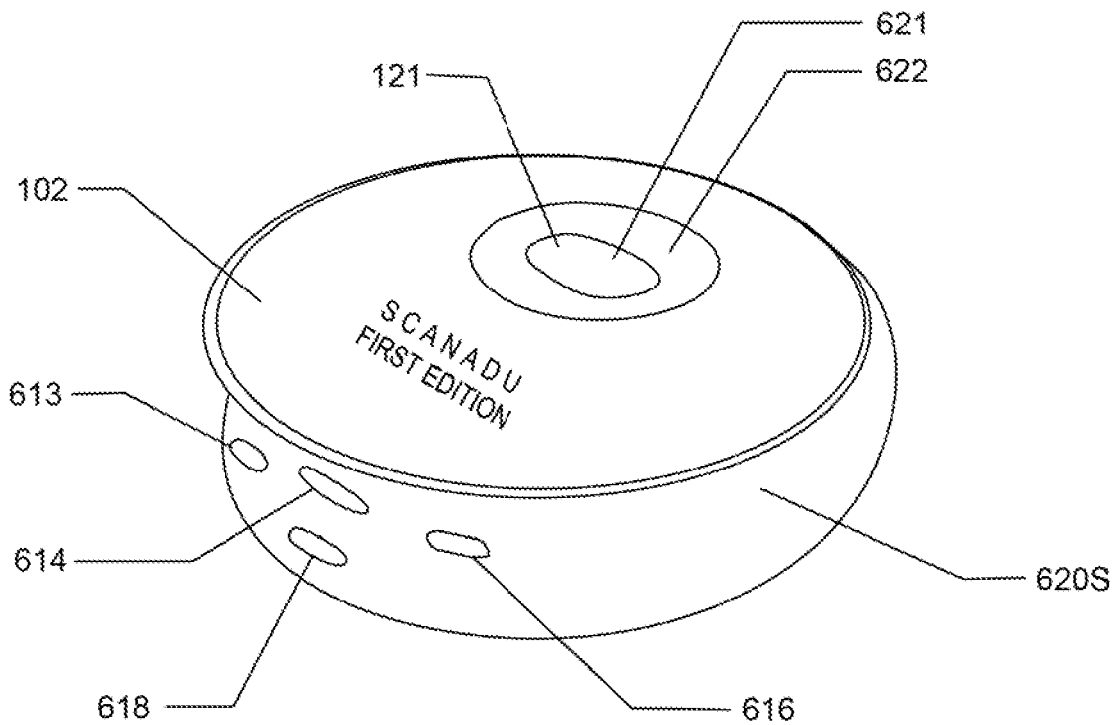

In FIG. 6B, a top back perspective view of the wireless vital signs scanner 102 is illustrated. The wireless vital signs scanner 102 illustrates various aspects of the invention in the side cylindrical surface 620S. The wireless vital signs scanner 102 includes a power button 613, a serial port connector 614, an optional wireless connection LED 618, and a power light-emitting diode 616. The power button 613 may be pressed to power the wireless vital signs scanner 102 on. The serial port connector 614 may be a micro universal serial bus connector to allow a micro USB cable to plug thereto. The micro USB port may provide an external power source to charge the rechargeable battery within the wireless vital signs scanner 102 and also may serve as a wired data port for updating firmware or transferring data to a computer or storage device. The optional wireless connection light-emitting diode 618 provides a visual indicator that the wireless vital signs scanner 102 is coupled to the wireless personal portable multi-function device 104 over its wireless communications channel 103A as illustrated in FIG. 1A. The power light-emitting diode 616 provides an indicator that the wireless vital signs scanner is powered on by the power button 613.

Figure 6C:
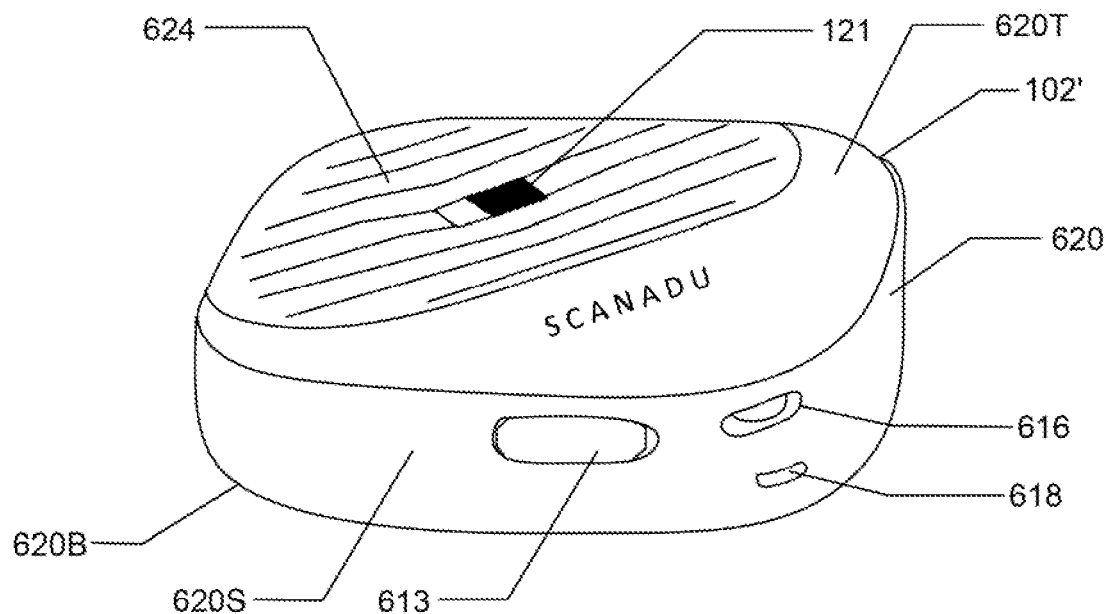
FIGS. 6C-6D are perspective views of another embodiment of the invention.

In FIG. 6C, a vital signs wireless scanner 102' is illustrated having a generally diamond shaped body housing 620. In this case the housing top 620T and the housing bottom 620B generally have a diamond or a square shape to match that of the side cylindrical surface 620S. The top or bottom housing portion 620T may each include a gripping surface 624 with corrugations or channels so that a user may comfortably and securely hold the wireless vital signs scanner 102'. The gripping surface 624 may be formed of a conductive material to aid the top and or bottom electrodes in forming an electrical connection to a user's body.

Figure 6D:
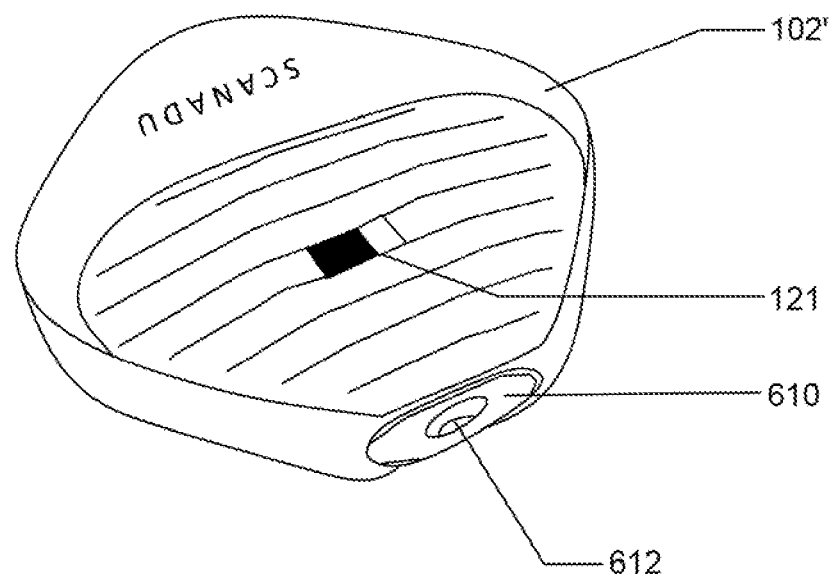

Referring now to FIG. 6D, a top front perspective view of the wireless vital signs scanner 102' is illustrated. The wireless vital signs scanner 102' includes the front electrode 610 and front sensor 612.

While the electrode 622 and the gripping surface 624 are illustrated in the top housing 620T, they may also be implemented in the bottom housing portion 620B instead of the top. Instead of an index finger making a connection with a top electrode 622, a thumb finger may couple to a bottom electrode (not shown) to provide a larger surface area contact to the body in the bottom housing portion 620B.

Figure 7A:
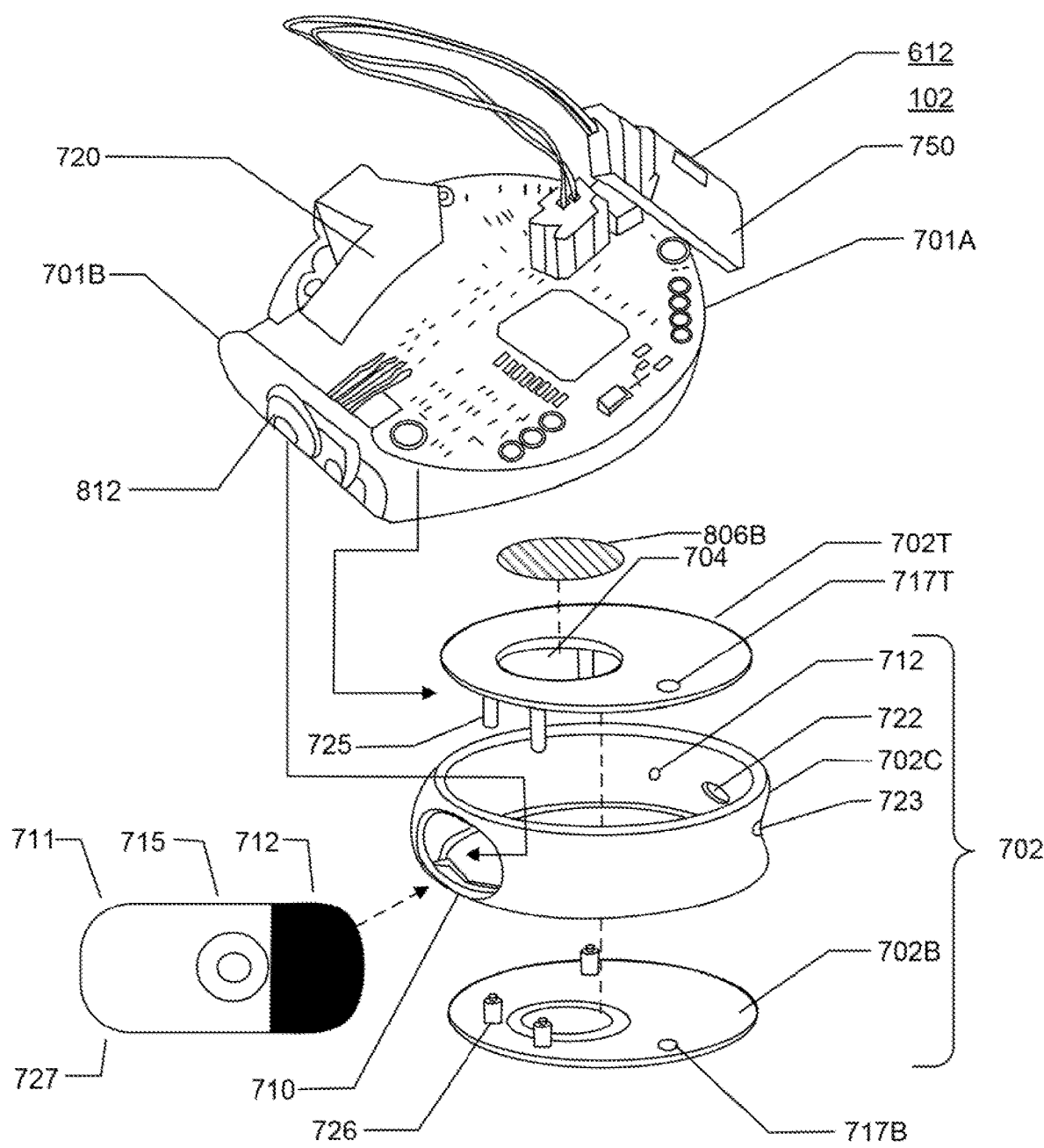
FIG. 7A is an exploded view of the exemplary portable wireless vital signs scanner.

Referring now to FIG. 7A, an exploded view of the wireless vital signs scanner 102 is illustrated. The exterior components of the wireless vital signs scanner 102 are formed of parts that can be wiped clean by a damp towelette or a disinfecting wipe. In this manner, the scanner 102 may be shared by users in a family with less worry about spreading bacteria and germs. Each user may have a personal profile or preferences stored in the scanning software application 140.

The wireless vital signs scanner 102 includes a main printed circuit board 701A and a daughter printed circuit board 701B coupled perpendicular to the main circuit board 701A. Because the scanner 102 is wireless, it includes a rechargeable battery and a connector port to which a cable may connect to recharge the battery. Preferably the battery may be charged in an hour or less. If the scanner 102 is used a few times a day, the charge of the rechargeable battery may last about a week. The main print circuit board 701A, the daughter printed circuit board 701B, and the rechargeable battery form an electronic sub-assembly 701.

The electronic sub-assembly 701 is inserted into a housing 702 of the vital signs scanner 102. The sensors on the front daughter board 701B are aligned into a front sensor opening 710 in the side housing ring 702C of the housing 702. A ribbon cable 720 electrically connects the front daughter board 701B to the main print circuit board 701A. A sensor 812 in the front daughter board 701B includes electrical leads that are coupled to the main printed circuit board 701A.

The main printed circuit board 701A is inserted into the housing ring 702C so that a serial bus connector 612 aligns with the connector opening 722 and the front sensor 812 is aligned into the front sensor opening 710. A top/bottom electrode 806B covers over an opening 704 and is electrically coupled to the main printed circuit board 701A and an ECG circuit mounted thereto.

The housing 702 of the wireless vital signs scanner 102 includes a top housing portion 702T with a top electrode 806B, a side housing ring 702C, and a base housing portion 702B. The orientation of the housing 702 for the scanner 102 may be altered such that the housing base 702B becomes the housing top 702T and the housing top 702T becomes the housing base 702B with a bottom electrode 806B to couple to a thumb. Electrodes may also be in both the housing base 702B and the housing top 702T to provide a lower resistive coupling to the user's body.

The top housing portion 702T includes a microphone opening 717T and a plurality of posts 725 and an electrical sensor opening 704. The housing base 702B may include a microphone opening 717B and a plurality of pillars 726 that can interface to the posts 725 when the housing is assembled together about the printed circuit boards.

The wireless vital signs scanner further includes a front cover 711 to fill in the front sensor opening 710 in the side housing ring 702C. The front side cover 711 includes a plastic cover portion 712 and a front electrode portion 727 with a lens 715 transparent to thermal wavelengths to allow the sensor 812 beneath it to capture a measure of temperature. The plastic cover 712 is also transparent to various wavelengths of light that are used by the vital signs sensors. The front electrode portion 727 of the front cover 711 is formed of a conductive material, such as stainless steel metal, to form a circuit when pressed up against the user's body at the forehead, finger, chest or elsewhere. The shape of the front electrode 727 can vary with the shape of the wireless vital signs scanner 102.

The side housing ring 702C includes one or more LED openings 712 to receive the power light-emitting diode 616 and the optional wireless connection light-emitting diode 618. The side housing ring 702C further includes a power button opening 723 through which the power button 613 may extend.

Figure 7B:
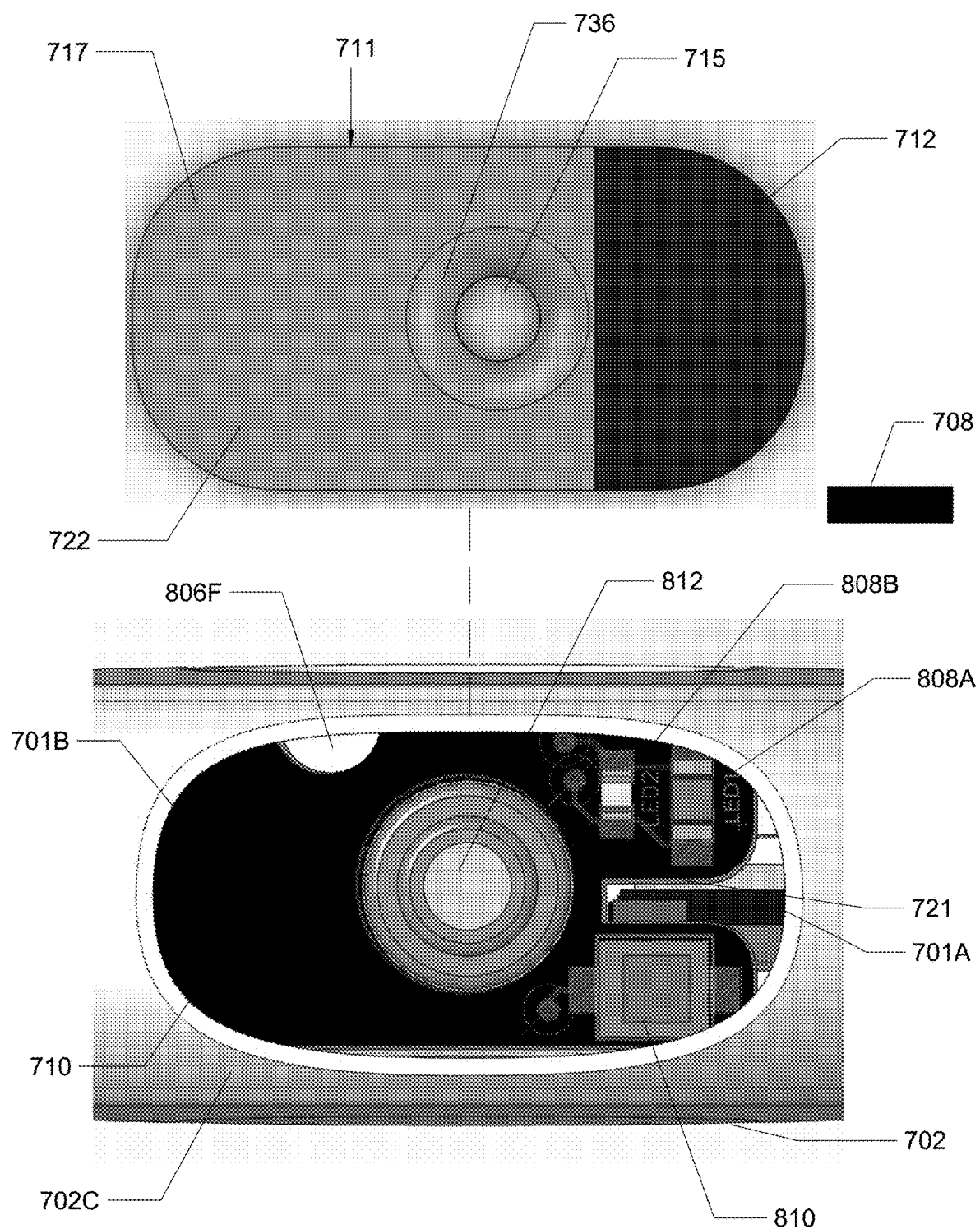
FIG. 7B illustrates a partially assembled exemplary portable wireless vital signs scanner

FIG. 7B illustrates a partially assembled wireless vital signs scanner 102. Through the front opening 710 in the side housing ring 702C, the front daughter printed circuit board 701B includes a slot opening 721. The slot opening 721 may be used to receive a shade 708 that separates the LEDs 808A-808B from the photo diode 810. The shade 708 deters light emitted by the LEDs 808A-808B from directly being impinged onto the photo diode 810. The wire (not shown in FIG. 7B) from the front electrode 727 may inserted through the opening 706 and then coupled to the main PCB and the ECG circuit. The front cover 711 can then assembled to cover over the front opening in the side housing ring 702C of the housing.

The daughter printed circuit board 701B is arranged to be substantially perpendicular with the main printed circuit board 701A. As previously discussed, the front cover 711 includes a transparent cover portion 712 and a metallic conductor portion 727, and the lens 715. The transparent cover portion 712 covers over one or more light-emitting diodes 808A-808B generating various wavelengths of light, and a photo diode 810 that receives various wavelengths of light. The light generated by the light-emitting diodes 808A-808B is shined onto the users forehead and reflected back to the photo diode 810. Light with known time periods may be generated by the light emitting diodes (LEDs) 808A-808B with different wavelengths and radiated onto a user's forehead. The reflection is detected by the photo diode 810 to form an electrical signal that is analyzed. In this analysis of the signal generated by the reflected lights of different wavelengths, a measure of oxygenation in the blood stream may be generated.

The front side cover 711 includes the transparent lens 715 with a center aligned into the optical axis of the front side sensor 812 so that additional vital signs measurement may be made from the forehead of the user. An opening 706 in the daughter board 701B allows a wire to pass through from the front electrode 727 and be coupled to a wire trace on the main PCB that is coupled to the ECG circuitry mounted thereto. When pressed against the user, the metallic electrode portion 727 of the front side cover 711 makes an electrical contact to the forehead or other body portion of the user. An insulating ring 736 under the electrode portion 727 of the front side cover may be used to isolate any metal of the infrared thermometer 812 from the electrode portion 727.

Figure 8A:
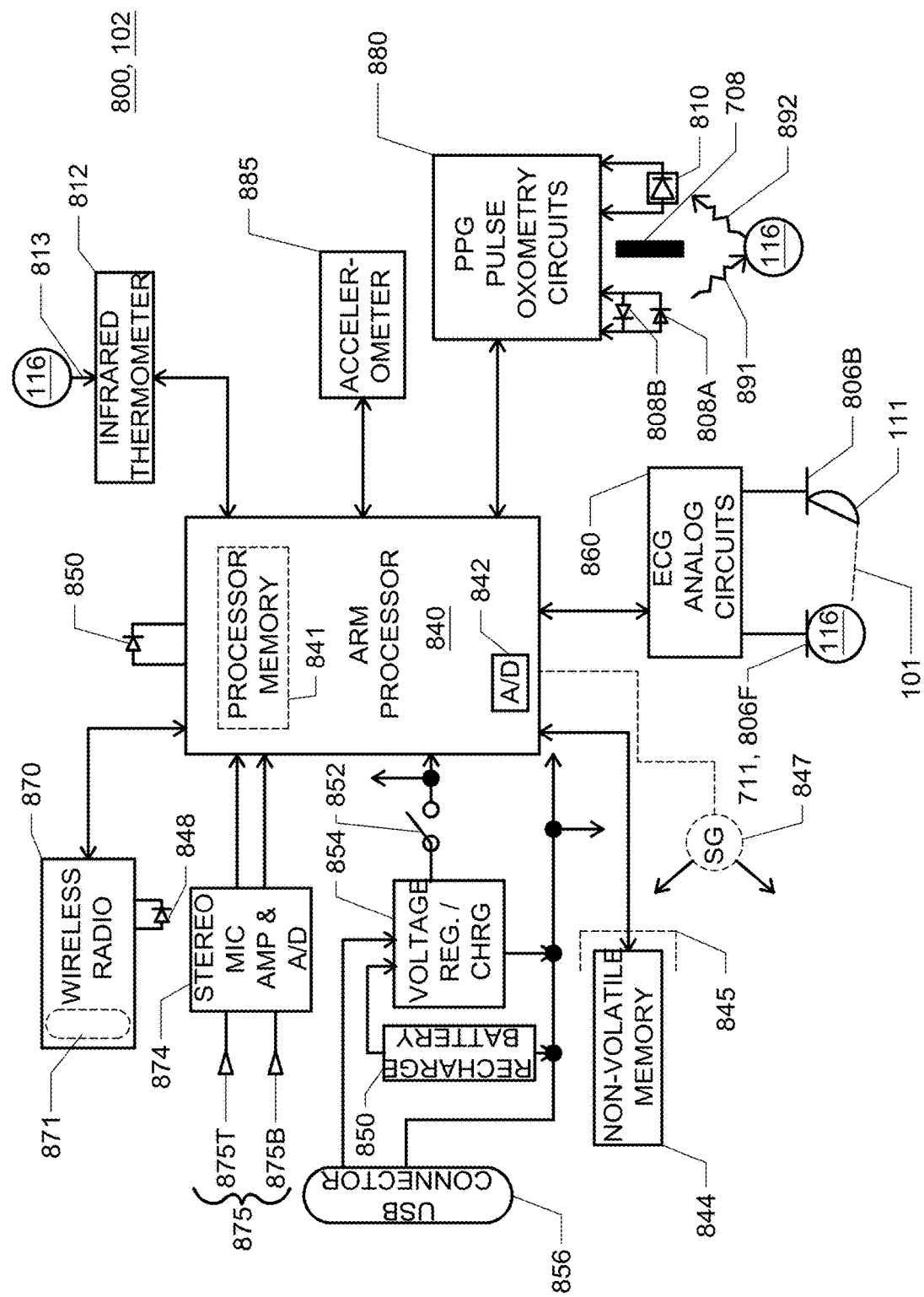
FIG. 8A illustrates a functional block diagram of electronic circuitry within the exemplary portable wireless vital signs scanner.

FIG. 8A illustrates a functional block diagram of electronic circuitry 800 within the portable wireless vital signs scanner 102. The personal portable wireless vital signs scanner 102 associated with a given user profile stored in the user data of the wireless personal multifunction device 104. The wireless communication channel 103A between the scanner 102 and the multifunction device 104 may be a secure connection with information passed between each. The devices are typically paired to each other by a code so that no other wireless device may utilize the wireless communication channel 103A. A different wireless communication channel 103B may be generated between the vital signs scanner 102 and a personal computer 150, for example. Each of the wireless communication channels 103A, 103B may be a Bluetooth communication channel, for example, in which case the signal strength between each over a Bluetooth communication channel is relatively short with a limited distance over a range between zero and twenty-five feet, for example.

Referring now to FIG. 8A, electronic circuitry 800 of the portable wireless vital signs scanner 102 includes a processor 840 at the heart of the system. The processor 840 may be a reduced instruction set processor operating with embedded operating system software. In one embodiment of the invention, the processor is an ARM processor operating with MICRIUM's embedded real time operating system (RTOS).

To provide the wireless communication channels 103A, 103B, a wireless radio 870 is coupled to the processor 841. The wireless radio 870 is coupled to an antenna 871 that could be internal, as part of an overall radio system, or external to the wireless radio 870. An optional light emitting diode 848, used as a wireless connection indicator, is coupled to the wireless radio to indicate a successful pairing with the personal portable wireless digital multifunction device 104. To scan for vital signs over a period of time such as 10 seconds, the electronic system 800 includes an infrared thermometer 812, an accelerometer 885, a pulse oximetry sensor and a pulse oximetry circuit 880, and analog electrocardiogram circuitry 860. Coupled to the electrocardiogram circuitry 860 is the bottom or top electrode 806B, the front electrode 711, bottom/top electrode connection, and the front electrode connection 806F. As shown in FIG. 1A, a portion of a human body is coupled to the front electrode 711 and the top/bottom electrode 806B to form a circuit.

The pulse oximetry circuit 880 is coupled to a pair of light emitting diodes 808A-808B. Each of these emit light patterns that are reflected off of the user's forehead internally. The reflected light is captured by a photodiode 810 and coupled to the circuit 880. That is, incident light 891 from the light emitting diodes 808A-808B reflects internally off the user's head 116 as reflective light 892 which is received by the photodiode (PD) 810.

The infrared thermometer 812 detects the surface temperature of a use's forehead (or elsewhere) by measuring thermal radiation (referred to as Blackbody radiation) 813 emanating from the head 116 (or other body portion to which the scanner is pressed) of a user.

To power the circuits in the system 800 of the personal portable wireless vital signs scanner 102, a rechargeable battery 850 and a voltage regulator and battery charge controller 854 are coupled together into the circuits in the system 800 when the switch 852 is closed. The battery charge controller 854 is coupled to power pins of a serial connector 856 to receive an external DC voltage supply. The external voltage supply may be used to recharge the battery and power the system 800 when it is connected. The rechargeable battery 850 may hold a charge for a period of seven days, even while scanning multiple times during each day, due to the low power consumption of the circuitry and the limited period of time needed to perform a scan of the vital signs of a user. That is, the vital signs scanner 102 is not expected to be continuously powered on during a day, but powered up periodically to perform the scans as needed.

The processor 840 may include a processor memory 841 to store system instructions to control the circuitry in the system to obtain the scans and process the information obtained through those scans into a proper user format. To store the user data from each of these scans, a nonvolatile memory 844 is coupled to the processor 840. The nonvolatile memory 844 may be soldered to a printed circuit board with the processor 840. In an alternate embodiment of the invention, a connector 845 is provided so that the nonvolatile memory 844 is a removable memory card so that a user's data may be transferred from one scanner to the next, if needed.

A power LED 851 may be coupled to the processor 840 to provide an indication that the electronic system 800 is powered up. The system can be manually shut down via the scanning software application 140 so that the scanner 102 powers off. However, the scanner 102 can also automatically shut off after a predetermined period of time to conserve power and a charge on the rechargeable battery 850. The user then just needs to press the power switch 852, once again, to turn the system back on and scan for vital signs of a user.

The processor 840 includes one or more analog digital convertors 842 in order to receive analog signals from the infrared thermometer 812, accelerometer 885, pulse oximetry circuits 880, and ECG analog circuits 860. Electronic system 800 may further include a stereo microphone 875 consisting of a top microphone 875T and a bottom microphone 875B each coupled to a stereo microphone amplifier 874. The stereo microphone amplifier may have its own analog to digital converter, or the processor's analog digital convertor 842 may be used to convert analog signals into digital signals. For example, an ECG analog signal may be converted into digital signals with the analog digital convertor 842 of the processor. The stereo microphone 875 captures audio signals near the wireless vital signs scanner 102. The accelerometer 885 captures movement of the portable wireless vital signs scanner 102.

The combination of the audio information and the movement information may be utilized to determine the quality of the scanning information being obtained by the vital signs capturing circuitry. For example, the stereo microphone 875 may be used to capture noise from a user talking and plot that on a graph indicating noise spikes, or noise lines 330, such as shown in FIG. 3A. This provides feedback to a user about the quality of the scan at these intervals. The accelerometer 885 and the motion information may be similarly used to make a judgment about the quality of the vital signs scanned information being captured by the vital signs circuitry of the infrared thermometer 812, the pulse oximetry circuits 880, and the ECG analog circuits 860.

The microphones 875 in the portable wireless scanner 120 may also used to capture body sounds such as shown in FIGS. 1E-1F and store the captured body sounds in memory 844 as a potential symptom of a medical condition of the users body. For example, heart beat sounds may be captured by the microphones 875 when the scanner 102 is positioned against skin of the chest near ones heart, as is illustrated in FIG. 1E. As another example, lung or breathing sounds of air entering and exiting ones lungs may be captured by the microphones 875 when the scanner 102 is positioned against skin of the chest near a lung in ones body, as is illustrated in FIG. 1F.

To further optimize scanning results, scan quality algorithm monitor the vita signs scanning process and can provide feedback (visual and/or audible) to the user, such as through the multifunction device 104.

An optional audible sound generator 847 in the scanner 102 may be coupled to the processor 840 to provide audible user feedback to the user during the scanning process. The user feedback may help the user to perform better vital signs scan with the wireless vital signs scanner 102 and acquire a higher quality of vital signs measurements. The audible sound generator 847 may generate alert sounds indicating when the scanning process begins and ends. It may also generate an error signal indicating to the user that he is not properly using the scanner 102 and look for instructions on the device 104.

Figure 8B:
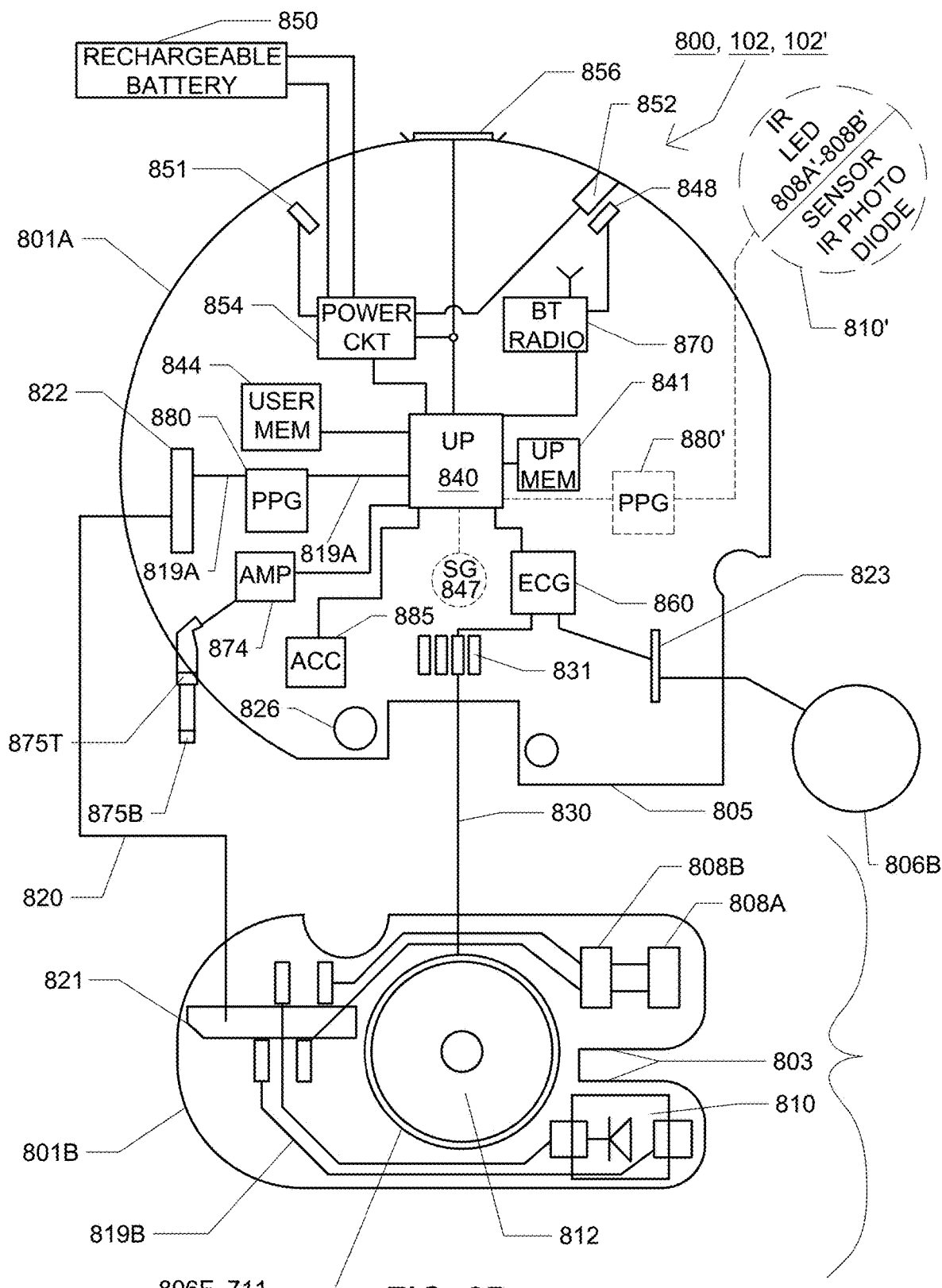
FIG. 8B illustrates a main printed circuit board coupled to a daughter printed circuit board with various electronic circuitries within the exemplary portable wireless vital signs scanner mounted to each.

Referring now to FIG. 8B, a functional block diagram of the electronic circuits 800 are shown mounted onto the main printed circuit board 801A and the daughter printed circuit board 801B. FIG. 8B also illustrates alternate locations for electronic circuits in the system 800 for alternate embodiments of the vital sign scanners 102, 102'.

A slot 803 in the daughter printed circuit board 801B receives a shade device 708. Light emitted by the LEDs 808A-808B is shaded by the shade device 708 so that it may not directly impinge onto the photo diode 810 in the daughter PCB 801B. Reflected light, reflected off the user's body, is desirable to be captured by the photo diode 810.

Wire leads 830 of the IR sensor 812 and the front electrode contact 806F are coupled to pads 831 of the main printed circuit board 801A. First and second LEDs 808A-808B and the photodiode 810 are coupled to connector 821 by conductive traces 819B on the daughter printed circuit board 801B.

The main printed circuit board 801A has a plurality of wire traces 819A coupling circuits mounted thereto together. The daughter printed circuit board 801B includes a plurality of traces 819B coupling circuits mounted thereto to connector 821. A ribbon cable 820 is used to couple signals between the daughter memory card 801B and the main printed circuit board 801A for the oximetry circuit 880. The oximetry electronic circuit 880 is coupled between the connector 822 and the processor 840 on the main printed circuit board 801A.

In accordance with one embodiment of the invention, if the oximetry sensors are moved to a top portion of the housing to sense oximetry through a finger, with the RLEDs 801A'-801B' and the IR photodiode 810', the oximetry circuitry may be moved to the opposite side coupled between the processors 840 and the LEDs 808A'-808B', 810 and mounted in the top portion of the housing. The bottom or top electrode 806B is formed of stainless steel to provide a good connection to either a thumb finger or an index finger. The electrode 806B is coupled to a connector 823 and to the ECG circuitry 860 on the main printed circuit board 801A.

The main printed circuit board 801A includes the processor 840, the wireless radio 870, the microprocessor memory 841 (either internal or external as shown mounted to the printed circuit board), an accelerometer 885, an amplifier 874, oximetry circuitry 880, 880', user memory 844, and battery charge circuit 854.

Top and bottom microphones 875T and 875B extend out from the main printed circuit board 801A by ribbon cables so that they may be mounted into the respective openings in the housing top and housing bottom. The microphones 875T, 875B may be coupled to the amplifier 874 which in turn may couple audio signals into the microprocessor 840. Mounted to the main printed circuit board is the power LED 851 and the connection LED 848. Further mounted to the main printed circuit board is a power on/off switch 852 coupled to the voltage regulator battery charge circuit 854 to signal for it to turn power on or off to components with the scanner 102. Additionally, mounted to the main printed circuit board 801A is a serial connector 856 coupled to the microprocessor. In one embodiment invention, the serial connector 856 is a micro universal serial bus connector.

An optional audible sound generator 847 may be mounted to the main PCB 801A and coupled to the processor 840 as shown. To avoid interference, the sound generator 847 may be positioned away from the microphones 875.

Main printed circuit board 801A includes a plurality of openings 826 that receive the pillars 725, 726 of the housing top 702T and housing base 702 B.

The daughter printed circuit board 801B includes a connector 821, light emitting diodes 801A-801B, and a photodiode 810 mounted thereto. The IR sensor 812 is inserted through a hole in the daughter PCB 801B, attached thereto with an adhesive, and supported thereby. The front electrode 806F around the IR sensor 812 is attached with an adhesive to the daughter PCB 801B for support.

The ribbon cable 820 couples signals of the light emitting diodes 801A-801B and the photodiode 810 regarding oximetry between the daughter board 801B and the main printed circuit board 801A for the oximetry circuit 880. With the terminals 830 of the IR sensor 812 coupled to the pads 831 of the main PCB 801A, signals of the IR sensor 812 regarding temperature are coupled into the processor 840. With the terminals 830 of the front electrode 806F coupled to one or more pads 831 of the main PCB 801A, signals of the ECG circuit 860 to measure heart activity (e.g., heart rhythm, heart rate, etc.) may be coupled into and out of a users body.

Thus, the personal portable wireless vital signs scanner integrates a plurality of sensors and a controller/processor together to synchronously obtain a plurality of vital signs at different times during a users day. Despite the integration of multiple sensors and a controller/processor into the scanner, the vital signs scanning device has a relatively low production cost. The integration with a ubiquitous consumer electronic device pre-owned by many users, the personal wireless multifunction device (e.g. smartphones, tablets, etc.), to display the vital signs data with vital signs scanning software, also keeps the costs low of the overall personal vital signs scanning system. The low costs of production of the vital signs scanner can allow lower retail pricing and higher volume of sales, enabling an average consumer to afford the vital signs scanning system to personally scan and monitor trends of their vital signs for as an important part of preventive medical care of their own bodies.

Figure 9:
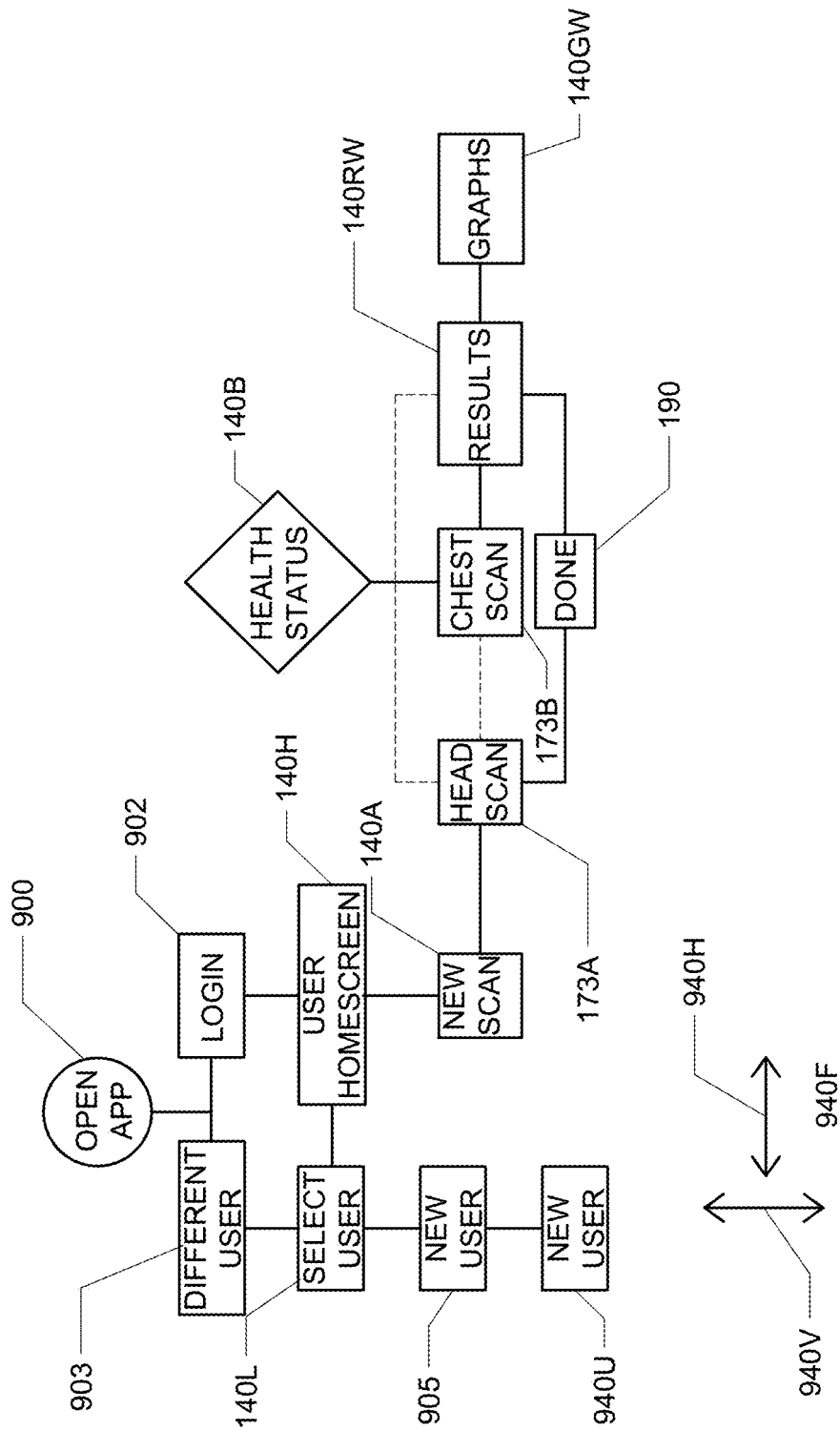
FIG. 9 illustrates an exemplary hierarchy of the vita signs graphical user interface provided by the vital signs scanning software application executed by the personal wireless multifunction device.

Referring now to FIG. 9, a diagram illustrating an exemplary hierarchy of windows provided by the scanning application software 140 is illustrated. A variety of vital sign scanning user interface windows of the scanning application software 140 have been described. The vital signs scanning application software 140 executed by a processor provides a user interface hierarchy of the vital sign scanning user interface (VSUI) windows. For example after the vital sign scanning application is opened at process 900, a scanning login button 902 may be presented to the user by the scanning application software 140. If the user is properly selected he chooses the login button to transition to a user home screen 140H. In the user home screen, a user inputs his login identification and password to gain access to personal vital signs scan data stored in the device 104. If the user is a different user a different user button 903 may be selected or a horizontal swipe finger gesture 940H may be used to go to a select user window 140L. If the user is not listed and is a new user, the select user window 140L may have a new user button 905 that jumps to a new user window 904U that is displayed to the user. In the new user window 940U, the new user may input his login user ID and password that he desires to use with the scanning software application to identify his personal vital signs scan data. Other information, such as sex, height, weight associated with a time and date may be entered by the user. As the days and/or years go by, the user may update this information in the profile so that the vital signs scanning system better knows what conditions might occur for the given user. The login and profile windows can also allow the scanning system to be shared with other users in a family. After logging in with user ID and password through the home screen, the scanning system application may display the initial scanning window 140A.

By using a horizontal finger gesture 948 over the scan type slider 171, the user may select a head scan 173A, a chest scan 173B, the results window 140C, or the graphs window 140D. If at any point in time the user feels the need to terminate the scanning process, the done button 190 in the user interface may be selected. By means of a vertical finger gesture 940 V in the scanning window 140A during a head scan 173A or chest scan 173B, or the results window 140C, the health status window 140B may be displayed. Alternatively a health status button 180 may be selected to display the health status window 140B.

Each of the screens/windows/slides of the vital signs scanning application may be navigated by pressing one or more virtual graphical buttons (e.g., back, done) and/or making one or more finger gestures 940F (e.g., vertically up/down 940V, horizontally left/right 940H) dragged across a touch screen. A navigation bar may alternatively be provided with navigation buttons to navigate between selected windows. The menu button may also be used to navigate to different windows. In other cases, pressing a button displays a different screen/window/slide such as the done button.

After scanning is completed, the scanning application software can automatically display the results window 140C. Additional buttons in the results window 140C may be used to navigate to various graph windows 140D, such as the temperature graph window shown in FIGS. 4A-4B. Additional buttons in the results window 140C may be used to navigate to various prognosis windows shown in FIGS. 5A-5B. In this manner, vital signs data and information can be displayed to the user in various ways.

The scanning software application 140 includes a number of instructions and routines that are executed by a personal wireless multifunction device 104. The personal wireless multifunction device 104 may include a smart phone, such as an APPLE IPHONE 5, IPHONE 4S, or SAMSUNG GALAXY S III, that supports Bluetooth Smart wireless communication with the vital signs scanner 102 and cellular wireless data communication, Wi-Fi wireless data communication, and/or Ethernet wired data communication over a communication network. To help everyone use the multi-function device 104, assistive technology may be added to the scanning software application 140.

The significant software routines of the scanning software application 140 include a scan procedure controller based on scan quality algorithm, UI implementation, wide area network interfacing to cloud services, scan results interpretation, and trend charting.

Cloud Data Service

The scanning device 102 detailed above allows a patient to effortlessly scan their vital signs multiple times throughout each day. The user-friendly scanning software application 140 running on the multi-function device 104 displays the client's vital signs in an easy to read manner. Combined, the two devices allow a user to take a more hands on approach to monitoring and maintaining their health. Further adding a cloud based/Wide Area Net (WAN) based access and storage system allows even further data analysis for an even more comprehensive health-monitoring program.

FIG. 10 is a block diagram illustrating an exemplary vital signs cloud system 1000 including a vital signs scanner 102, a multifunction device 104, and a vital signs server 1030 in communication together. A typical user scans their vital signs using the vital signs scanner 102. The raw sensor data is processed by a processor onboard the vital signs scanner into processed vital signs data. The processed vital signs data may then be wirelessly transmitted to the users multifunction device 104 and displayed by a scanning application running on the multifunction device 104.

The multifunction device 104 may store multiple monitoring sessions. For instance, the multifunction device 104 may store one years worth of processed vital signs data. Intermittently, the processed vital signs data may be uploaded to a vital signs storage server 1030. For privacy and data fidelity, the processed vital signs data are encrypted to minimize data security risks on the multifunction device before upload. The off-site vital signs storage server may hold multiple years' worth of the user's vital signs data, even a lifetime's worth of data. To upload processed vital signs data from the multifunction device 104 to the vital signs storage server 1030, a secure connection may be made via a wide area network (WAN) 1001, such as a wireless network, e.g., Wi-Fi (any wireless local area network and wireless access point products that are based on the Institute of Electrical and Electronics Engineers 802.11 standards) or cellular networking; a wired network; and/or a combination of a wireless network and a wired network.

In FIG. 10, a wireless communication connection or channel 1032 may be formed between the multifunction device 104 and the network 1001 for bidirectional data communication to/from the vital signs storage server 1030. A communication connection or channel 1033 may be formed for bidirectional data communication between the network 1001 and the vital signs storage server 1030. Vital signs data stored in the multifunction device 104 may be uploaded to the network 1001 and then to the storage server 1030. Historical vital signs data may be downloaded from the storage server 1030 over the network 1001 to the multifunction device 104 by the same the communication connections or channels 1032,1033. Data flows in both directions (bi-directional) over the communication connections or channels 1302,1033 as indicated by the parallel double-headed arrows.

To protect privacy, the multifunction device 104 encrypts the data that is transmitted to the vital signs storage server 1030 over the network 1001. The multifunction device 104 decrypts encrypted data that is received from the vital signs storage server 1030 over the network cloud 1001. To enable decryption of the encrypted data on another device, proper authorization is needed. Data flow back to the multifunction device 104 from the server 1030 may include, for example, summary data of several months or even years of the user's vital signs.

Personal Vital Sign Curves

A single page of a novel does not tell a complete story. Similarly a single day's scanning result does not accurately portray a patient's medical history. The aggregation of a patient's scanning results throughout an extended period of time may be more comprehensive and thereby more useful to both the user and the user's medical professional. Accumulated vital signs data may be offloaded to cloud servers, such as the server 1030 shown in FIG. 10. The accumulated vital signs data may be processed to show trends in the user's vital signs over time. The accumulated vital signs data for a given user may also be compared with groups of users with similar traits to check for normal and/or abnormal health conditions. The accumulated vital signs data for a given user may also be shared with the user's medical professional to verify normal and/or abnormal health conditions.

Figure 11A:
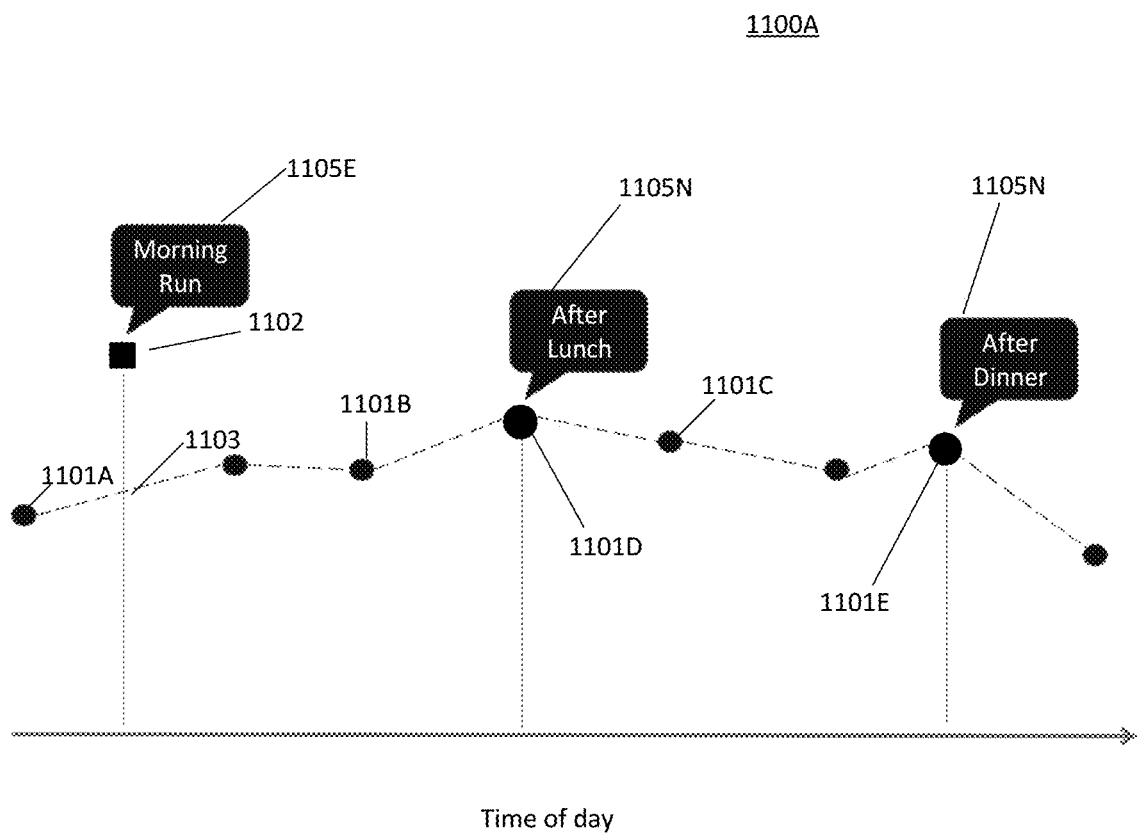
FIG. 11A illustrates a basic daily vital sign curve over one twenty-four hour period.
Figure 11B:
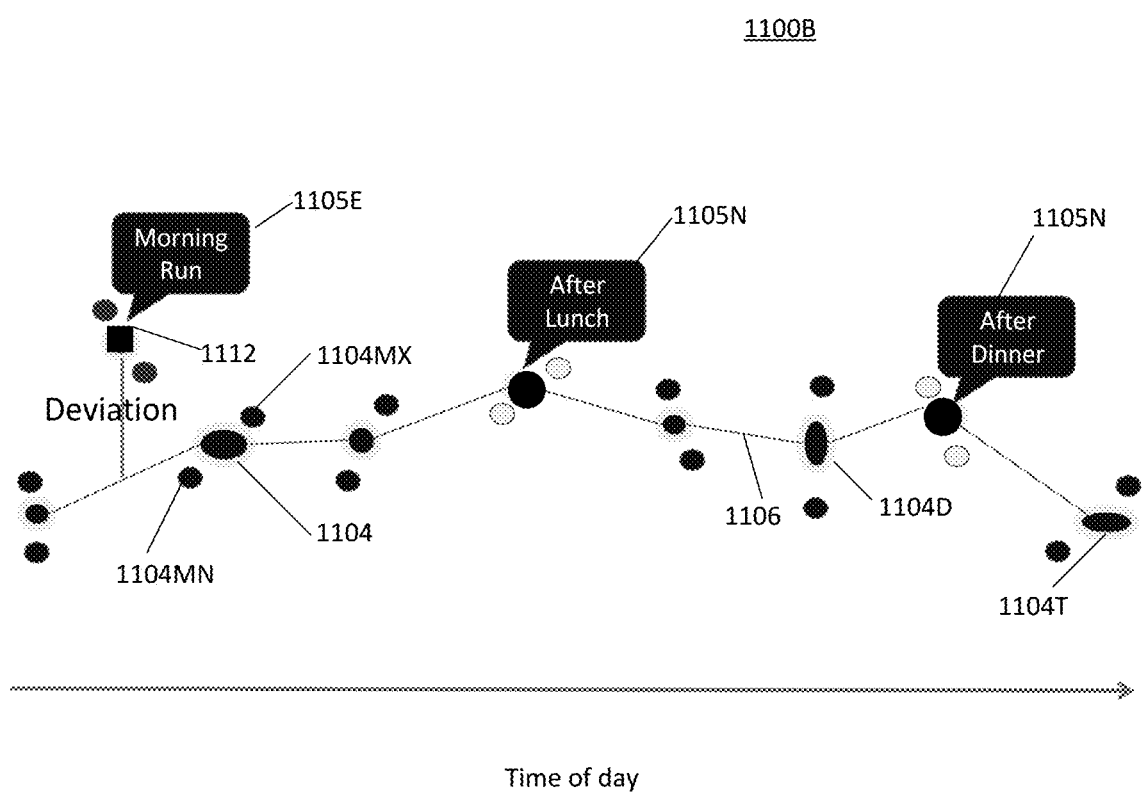
FIG. 11B illustrates a canonical average vital sign curve including a graphical representation of standard deviations.

The basic health of a user can be represented by reference vital sign curves of multiple vital sign measurements. Every user is different so their personal vital sign curves will be different. A tagged reference vital sign curve can be represented as a canonical vital sign curve plus tagged deviations, such as shown in FIG. 11B. Everyone will have his/her own canonical vital sign curve as the base temporal representation of one vital sign measurement.

Easy-to-use vital sign scans that may be done anytime and anywhere, motivates the average user to start building personal vital signs curves that lay the foundation of their basic health. The ease of using the vital signs scanner will encourage a healthy routine of constant monitoring. Over time the accumulated vital signs data may be processed to show trends.

To build useful reference vital signs curves, the vital signs are aggregated according to time. FIG. 11A illustrates a basic vital signs chart 1100A over a single twenty-four hour period. The x-axis indicates the time of day and the y-axis indicates the magnitude of the given vital sign being displayed. Plotted points represent discrete vital sign scans at different time points during the same day. Events may occur during the day that can effect the vital signs data during a vital signs scan. Some events may be extraordinary that occur infrequently and not considered in forming the curve 1103. Other events may be normal or ordinary, occurring regularly or frequently, and are to be considered in forming the basic health curve 1103.

The plotted points on the chart may have different shapes (e.g., circular, square, or triangular) or different colors (e.g., blue, red, green) to indicate additional information about a plotted point. Circular plotted points, such as points 1101A, 1101B, and 1101C, may represent normal discrete vital sign scans at different time points during the same day. Square plotted points are also vital sign scans captured at a different time point during the same day, such as square plotted point 1102. The square plotted points, such as square plotted point 1102, may be tagged with an extraordinary event tag 1105E, such as a morning run, during which time point the vital signs scan may be taken and substantially deviate from normal.

Other ordinary or normal occurring daily events may be tagged with a normal event tag 1105N after which vital signs are taken, such as when vital signs are taken after eating a meal. The circular plotted point for vital sign scans taken after such normal tagged events, such as plotted points 1101D-1001E, may be colored differently, shaded differently, or shaped differently than other circular plotted points for which no event is tagged. These points are still considered to be normal and plotted on the curve 1103. For example, vital signs may be taken after lunch and/or after dinner and tagged as a normal event with a normal event tag 1105N for plotted points 1101D-1101E, such as shown in FIG. 11A.

The curve 1103, a one-day vital sign curve, may be plotted between the circular or normal plotted points to show a selected days trend for a selected vital sign of the user. The curve 1103 represents the daily trend of a single vital sign, such as body temperature for example. For different vital signs, such as blood pressure, blood oxygenation, heart rate, respiration rate, ECG values, etc., additional one-day vital sign curves may be generated and displayed to the user by additional user interface screens. While a one day vital sign curve is useful in determining a given days base health condition, historical vital signs data may be useful in determining averages and health trends of the user.

FIG. 11B illustrates a vital signs chart 1100B comprising data from multiple twenty-four hour periods. Historical vital signs data stored in storage devices (e.g., non-volatile memory) of the multifunction device 104 and in storage devices of the vital signs storage server 1030 are used to update a default canonical average curve 1106 for each vital sign. A canonical average curve 1106 may be plotted for a given vital sign that represents an averaging of the user's stored historical vital signs data. The canonical average curve 1106 may be an average of all the scans made by the user. Alternatively, the user may select the period of scans that are to make up the canonical average curve 1106. For example, the user may select a given week, month, year, or range of years of vital sign scans to plot and form the canonical average curve 1106 for each vital sign. Alternatively, a user may select all vital signs scans up to a selected age or all vital signs scans within a range of ages to plot and form the canonical average curve 1106 for each vital sign.

The canonical vital sign curve includes an indication of the standard deviation, as does the averaged tagged scans, e.g., Morning Run. Instead of circular plotted points, oval plotted points 1104 are used to show the standard deviations. The vertical deviation in an oval plotted point 1104 along the curve 1106, such as shown by the oval data point 1104D, indicates the standard deviation in the magnitude of the vital sign value that is taken over the historical scans. The time differences between the scanning sessions that make up the oval data points 1104 along the curve 1106 can also be indicated. A horizontal stretch of the oval data points 1104 indicates the variation in times of day when aggregation of historical scans were taken. For example, the oval plotted data point 1104T illustrates an elongation along the curve 1106, indicating that there is a variation in time (e.g., 30 minutes for vital signs scans and data obtained at 10:00 PM, 10:05 PM, 10:15 PM, 10:20 PM, and 10:30 PM that are aggregated together into the plotted data point) when the vital sign scans were taken over the selected period of days, months, or years.

A rectangular plotted point 1112 may also be used to indicate history of similar extraordinary events that are not considered in forming the curve 1106. Similar to the oval plotted points, the rectangular plotted point 1112 may be stretched vertically to show the standard deviation in the vital signs data over the selected history of daily scans. Additionally, the time when the vital signs scan is taken after the same extraordinary event can differ. The rectangular plotted point 1112 may be stretched horizontally to show the time variation in the vital signs data over the selected history of daily scans for the event.

The maximum sign data point 1104MX and the minimum vital sign data point 1104MN associated for each oval plotted data point 1104 may also be plotted about each as shown in FIG. 11B. The maximum sign data point 1104MX and the minimum vital sign data point 1104MN may be vital sign values that influence the oval plotted data point 1104.

A user may tag additional information about each vital signs scan. For example, additional information that may be tagged to the vital signs scans includes where and why a user is taking the vital signs scan. A tag 1105 may be a standard event that occurs every day, such as a meal at breakfast, lunch, and dinner. A tag 1105 may also describe the basic health condition of a user at the time of the scan. If the user is sick, has a fever, or feels dizzy during a vital signs scan, the user can annotate that information in a tag to the vital signs scan. Other health information that may tagged includes medication information, such as a tag for the name and dosage of the medication taken at or near the time of the vital signs scan. Even dietary information may be important information that can be added to a vital signs scan by use of a tag. For example, a user may input tags describing a high protein or high carbohydrate meal before a scan.

To be more specific, each vital sign measurement is presented by a tagged reference curve or a temporal curve with sample points annotated by attributes. As a result, the reference vital curves are tagged curves of vital sign measurements. These are vital signs curves with knowledge tags that capture knowledge in the form of descriptions, categorizations, notes, annotations, or even hyperlinks regarding the scan.

The information in an event tag may provide an explanation for a scan that lies outside the canonical average curve. For example, in FIG. 11B, the square plot point 1102 tagged with the event tag 1105 "Morning Run" lies well above the canonical average curve. A user looking at that scan without the benefit of an event tag may not remember why their vital sign was so elevated during that scanning event. However, with the event tag, a user may review their aggregated vital signs data and filter such deviations. Standard tag events such as morning, lunch and dinner that repeat, for example, can be added to the canonical curve, while other tag events that are infrequent or less repetitive (e.g., one time events) can be excluded from the canonical curve calculation.

Optionally, similar events may even be aggregated and displayed so that all "Morning Runs" for a month or a year could be plotted together in an event tag 1105, such as the event tag 1105 in FIG. 11B. Elevated vital signs outside the normal average for a "Morning Run" event could then alert the user to potential medical problems that may have remained undetected without the event tag system.

In one embodiment of the invention, canonical curves and tagging may be facilitated through a user interface of the vital signs scanning software application 140 that is executed by a processor. Upon initialization, the scanning software application 140 provides a default canonical vital curve without tagged deviation. After each successful scan, the scanning software application 140 asks users for optional tagging information.

Figure 12A:
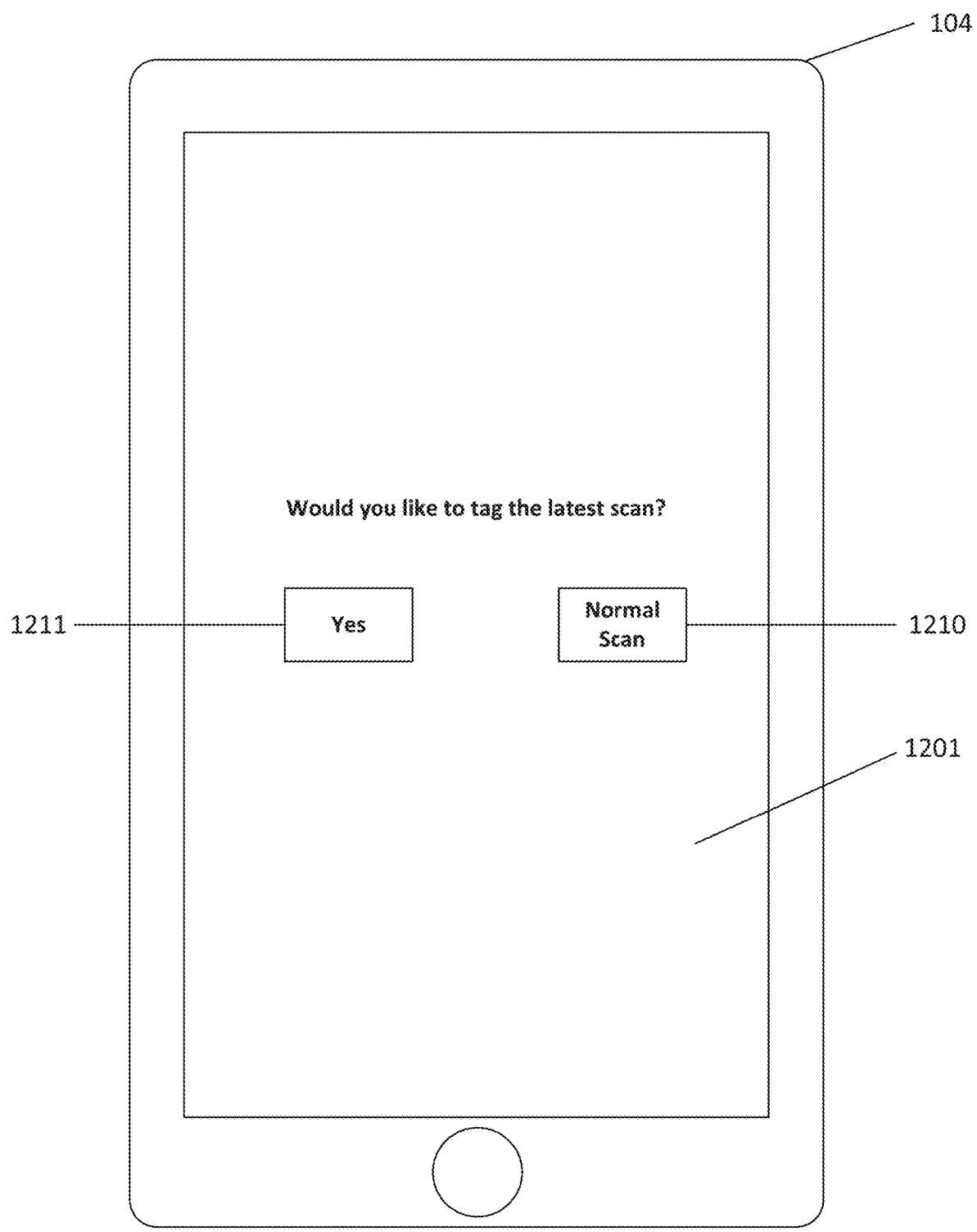
FIG. 12A, illustrates an exemplary tagging screen displayed on a multifunction device.

FIG. 12A, illustrates an exemplary initial tagging user interface screen 1201 displayed by the vital signs software application 140 on the multifunction device 104. The software application 140 queries the user through the tagging user interface screen 1201 as to whether they wish to add a tag to the latest vital signs scan. The user can select a decline to tag the vital signs scan by selecting a normal scan user interface button 1210. The user can select to tag the vital signs scan with additional information by selecting the yes user interface button 1211. If the user selects the yes user interface button 1211, another user interface screen is displayed by the vital signs software application 140.

Figure 12B:
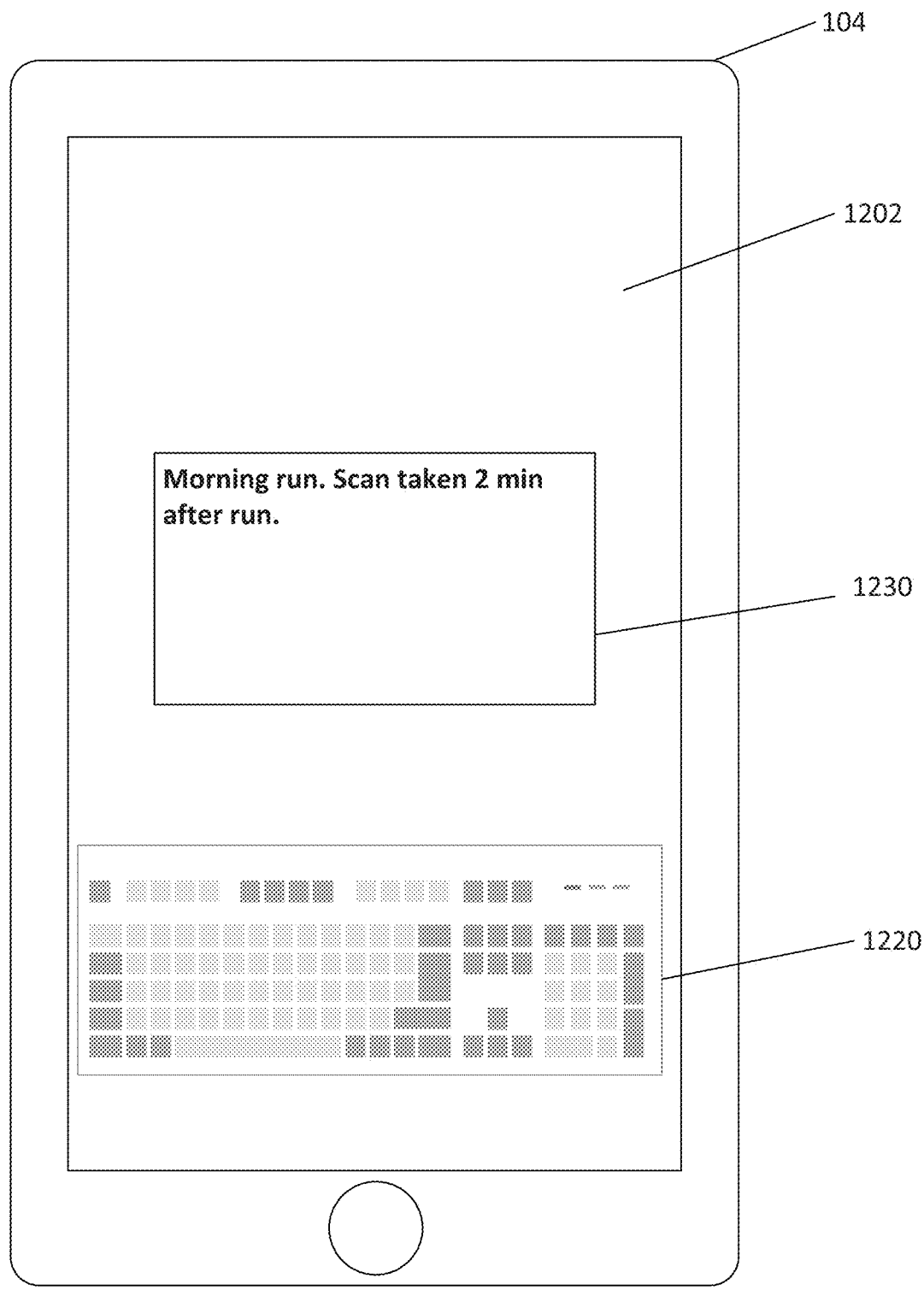
FIG. 12B, illustrates an exemplary tagging screen with virtual keyboard to enter the tagged information.

Referring now to FIG. 12B, a tag entry user interface screen 1202 is displayed by the vital signs software application 140 on the display screen of the multifunction device 104. The tag entry user interface screen 1202 includes a virtual keyboard 1220 to allow input of the tag information that is to be tagged to the vital signs scan. A tag information window 1230 displays the tag information that was input and is to be tagged to a vita signs scan.

By not tagging any information or by simply clicking the normal scan button 1210, the software application 140 will understand this is to be a normal vital signs scan with normal sample points, and add the normal scan as an update to the canonical vital curve.

With a tagged scan and tagging information, the canonical vital signs curve will not be updated. Rather, one tagged deviation will be calculated by subtracting the measurements against one canonical point with the same or similar timestamp from the canonical vital curve.

When more and more scanned points are added, the vita signs software application 140 will perform a clustering algorithm to keep the representation of the canonical vital curve and tagged deviations compact. Once enough vital sign data is accumulated, with the user's acknowledgement and authorization, the vital signs software application 140 can start making useful recommendations based on a comparison of the current vital signs scan data from a current vital signs scan with a historical canonical vita signs curve associated with the user.

Figure 13:
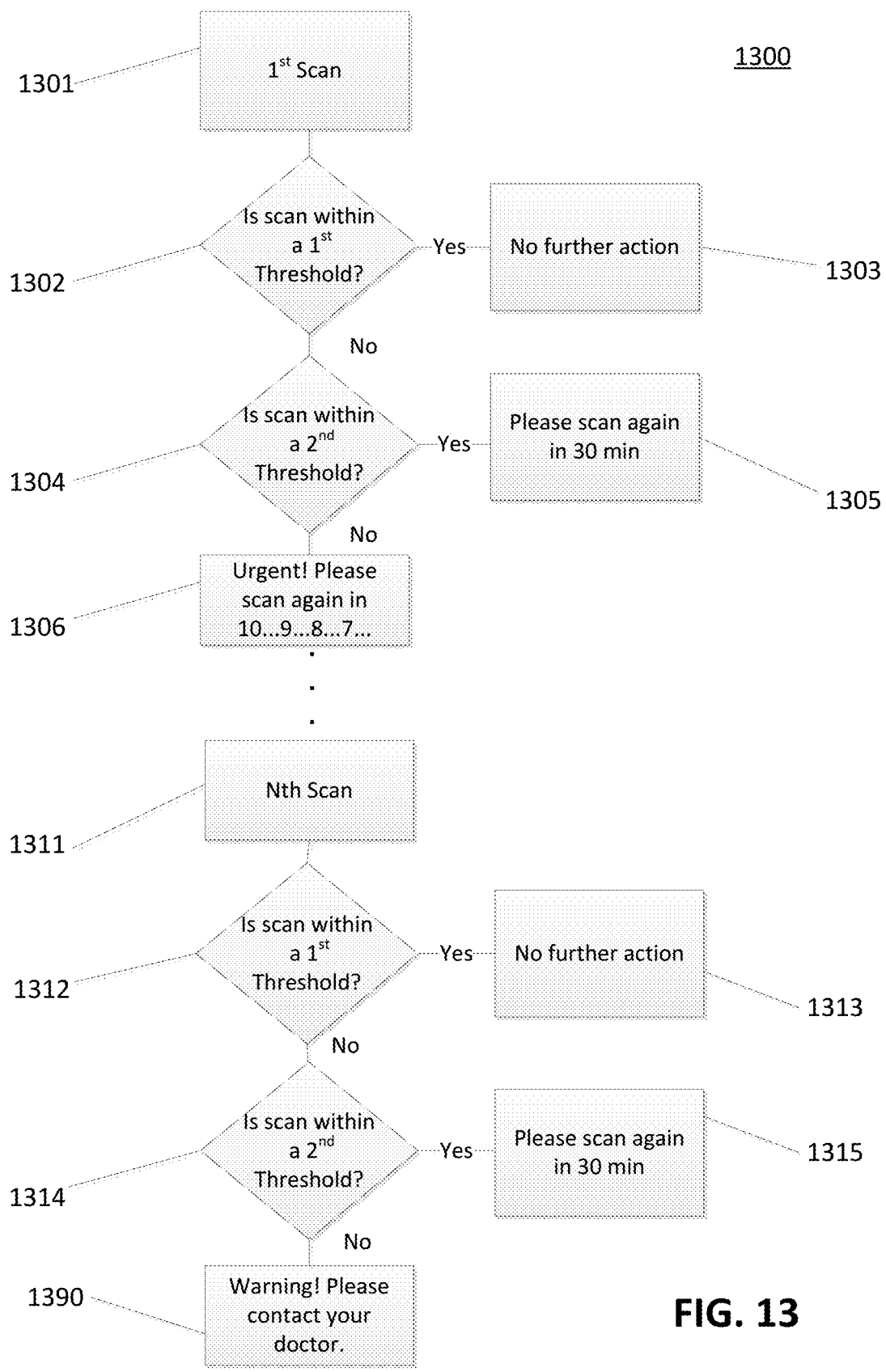
FIG. 13 illustrates a flow diagram for giving users recommendations during the vital sign scanning process.

Referring now to FIG. 13, a flow chart of a method 1300 of providing user recommendations during the vital sign scanning process is shown. The vital signs software application 140 may make scanning recommendations to improve vital signs monitoring. In one embodiment of the invention, the software application may assign thresholds that trigger certain recommendations. Alternatively, users may set up the thresholds themselves based on well-known thresholds (e.g., low grade fever at 100 degrees Fahrenheit, high grade fever 104 degrees Fahrenheit, Hyperpyrexia at 106.7 degrees Fahrenheit, constant fever over 24 hours, chronic fever over three days, prolonged fever of 10 days or more) available to the public.

The method 1300 starts with a first vital signs scan 1301. The process then goes to process block 1302.

At process block 1302, a determination is made if the current (tagged) vital signs scan is within a first threshold from the (tagged) reference vital curves. If yes, the process goes to process block 1303 and the user is informed that no further action is needed on their part. With current vital signs data being within the first threshold difference, it indicates a more normal condition of the user with the current vital signs scan. If the current vital signs data is not within the first threshold difference, it may indicate a less normal condition. If the current vital signs data is outside of the first threshold difference from the reference vital sign curves, further investigation is undertaken with the process going to process block 1304.

At process block 1304, a determination is made if the magnitude of the vital signs data associated with the current (tagged) vital signs scan deviates from the (tagged) reference vital curves by more than a second threshold. That is, is the magnitude of the vital signs data within the second threshold value while exceeding the first threshold value. The second threshold could represent for example a maximum set value and/or a minimum set value for the vital sign data. If the vital signs value does not exceed the magnitude of the second threshold, perhaps some event or activity caused it to be temporarily be outside the first threshold. Another scan may be advisable after waiting a predetermined period of time. The process can go to process block 1305.

If the current (tagged) scan data of the most current vital scans deviates from the (tagged) reference curves beyond the second threshold, the process goes to process block 1306.

At process block 1305, the vital signs software application 140 can display a reminder on the display of the multifunction device 104 that the user should take a follow-up scan within a predetermined period of time, such as within the next thirty minutes.

At process block 1306, the vital signs software application 140 can display a warning sign on the display of the multifunction device 104. The vital signs software application 140 can automatically set a timer instructing the user to urgently take a follow-up vital signs scans.

The vital signs software application 140 can repeatedly step through the scanning and the determination processes N times. At process block 1311, an Nth vital signs scan is performed with the vital signs scanner and multifunction device. At process block 1312 a determination is made if the magnitude of the vital signs data of the current vital signs scan exceeds or is within the first threshold. At process block 1314, a determination is made if the magnitude of the vital signs data of the current vital signs scan exceeds or is within the second threshold. If the vital signs scan results continuously exceed the second threshold difference or get exceedingly worse, the process goes to process block 1390. If the vital signs scan results continuously decrease and fall below the first threshold difference, then the process goes to process block 1313.

At process block 1313, an encouraging icon e.g. smiley face or thumbs up may be displayed with no further actions recommended.

At process block 1390, the vital signs software application 140 can display another warning on the display of the multifunction device 104. The vital signs software application 140 displays an urgent recommendation that the user immediately contacts a doctor or visit an emergency room.

If the vital signs scan results fluctuate between the first threshold difference and the second threshold difference, the software application 140 can display a recommendation that more follow-up scans be performed with the vital signs scanner within a time threshold or that a primary care practitioner be contacted for more information about the user's health.

Group Vital Sign Curves

With cloud storage of vital signs data by the vital signs storage server 1030, such as shown in FIG. 10, and a user interface provided by the vital signs scanning software application 140 of the multifunction device 104, users can share personal tagged reference vital curves with their physician or primary care provider (PCP). A user may elect to anonymously share his or her vital signs data with trusted vital sign groups.

Figure 18:
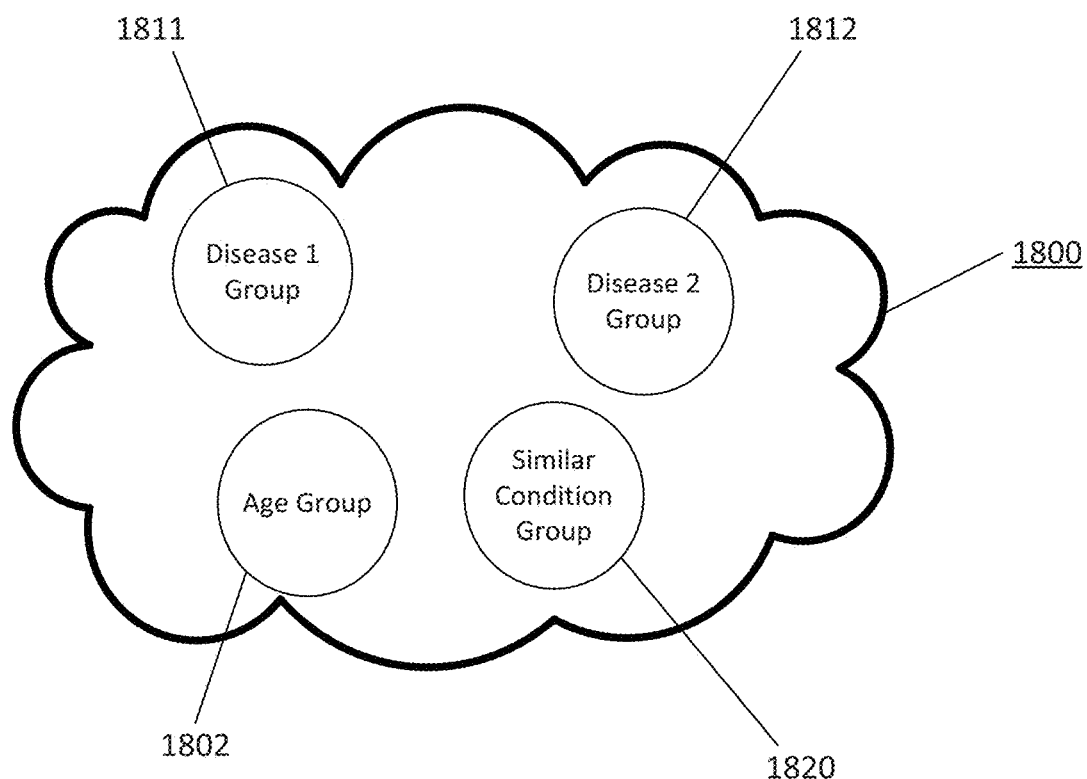
FIG. 18 illustrates a diagram of a global group of users.

Referring momentarily to FIG. 18, each user of a global group 1800 in cloud storage provided by a server may elect to be part of a vital sign group (e.g., one or more of groups 1802, 1811,1812, 1820). Vital sign groups may be formed according to similar traits or similar conditions that the user has that may be shared anonymously by the user, such as age (e.g., group 1802), gender, height, weight, and/or infirmity. For example, a vital signs group (e.g., group 1820) might be composed of senior citizens with high blood pressure, diabetes and kidney conditions. Another vital signs group (e.g., group 1802) might be composed based on age, such as infants under the age of two for example. Another vital signs group (e.g., group 1811) might be composed based on a first disease, such as diabetes for example. Another vital signs group (e.g., group 1812) might be composed based on a second disease differing from the first disease, such as cancer for example. While the groups shown in FIG. 18 do not overlap, some groups may intersect sharing users between each group as the user may have both conditions of each group. A user having the characteristic disease or trait of a vital signs group can elect to be a member of some vital signs group or not. To be automatically included in the global group, a user operates the vital signs scanner 102 to obtain his/her vital signs, uses the multifunction device 104 to perform a login process to a group vital signs server agreeing to share his vital signs data, and uploads his/her vital signs data form the multifunction device 104 to the group vital signs server to share data. Further, to be automatically included in basic vital signs groups, such as age, gender, sex, height, and weight, a user has the underlying characteristic of the basic vital signs group, such as being a male for example of a male vital signs group.

Figure 14:
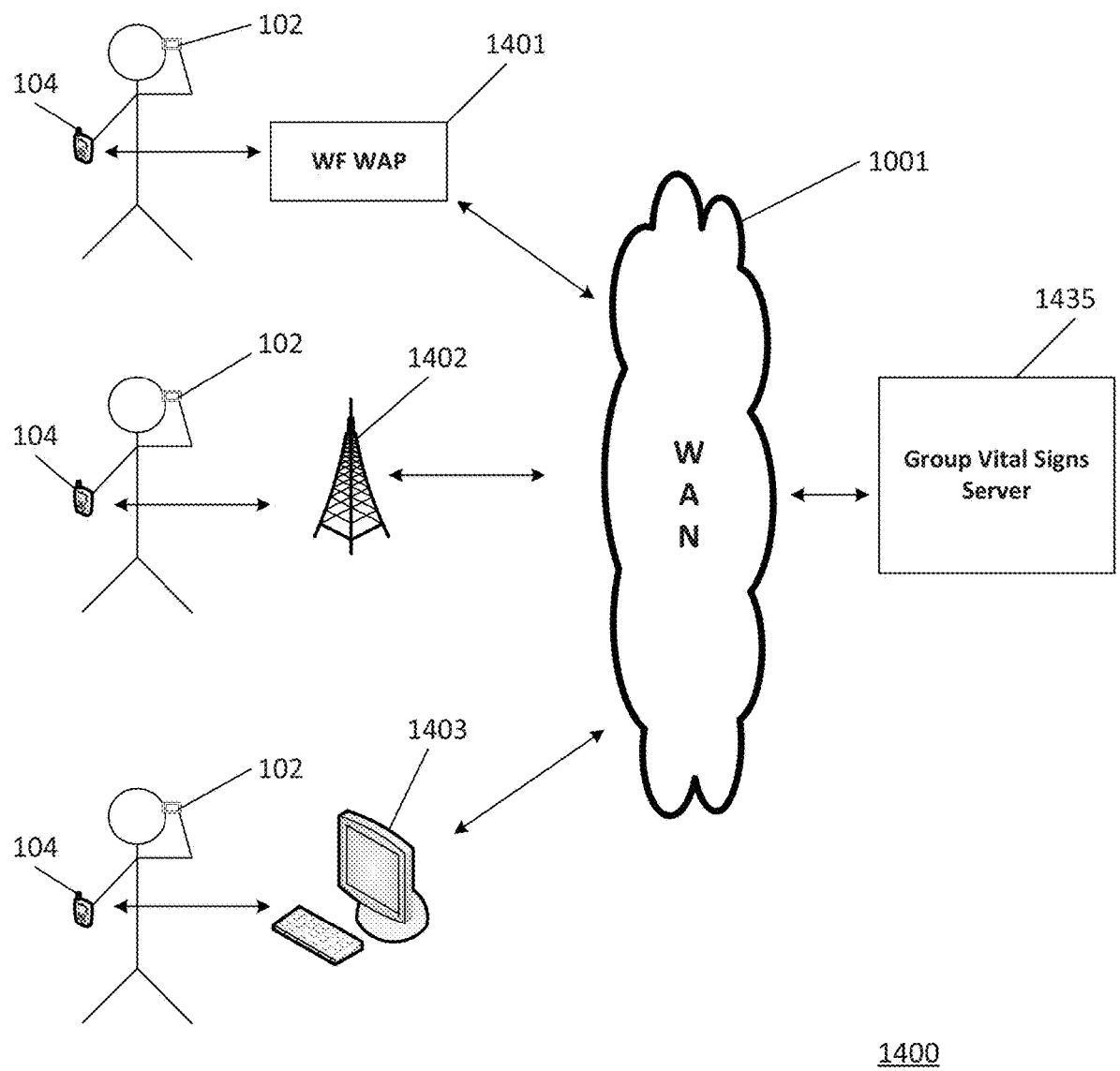
FIG. 14 illustrates a block diagram of an exemplary cloud server system with multiple users accessing a group server.

Referring now to FIG. 14, each user of the vital signs scanner 102 can elect to encrypt data and form a secure connection (e.g., an encrypted data connection) between a group vital signs server 1435 and their multifunction device 104 to exchange data over a network 1001.

The exemplary cloud server system 1400 depicted in FIG. 14 includes a plurality of vital sign scanners 102, and a plurality of multifunction devices 104 in communication with a group vital signs server 1435. The multifunction devices 104 can connect to the group vital signs server 1435 in different manners. Some multifunction devices 104 may connect to a network 1001 and the group vital signs server 1435 through a wireless access point (WAP) 1401. Other multifunction devices 104 may connect to the network 1001 and the group vital signs server 1435 through a wireless cellular data network 1402. Other multifunction devices 104 may make a wired connection with their personal computer 1403 that in turn is connected to the network 1001 and the group vital signs server 1435.

As with any cloud based application, the security of personal information can be important. Users can retain control of their group vital sign associations to maintain security of their personal information. Users can select which vital signs group they wish to belong and may change group affiliation as they see fit. The user may also select the people with whom they can share data. Only trusted people and primary care providers (PCPs) are given strict authorization to access the user's personal information. To others when sharing, the vital signs data is anonymous.

One exemplary method of maintaining information security is to limit the type of information that is transferred to the group vital signs server 1435. In one embodiment, only non-identifying (anonymous) information about the user is transferred to the group vital signs server. For example, each user can upload only their aggregated vital signs processed data.

The ability to select and change group affiliation also allows a user to compare their personal vital signs curves to different group reference vital signs curves. This feature can be beneficial if the user suspects that they are starting to develop a new chronic condition and wish to compare themselves against a different group before visiting their PCPs for an actual diagnosis. Potentially, the PCPs could recommend the user continue monitoring their vital signs at home using the vital signs scanner 102 and vital signs scanning software application 140 executed by the multifunction device 104 with follow-up office visits, saving both time and medical expense.

Figure 15:
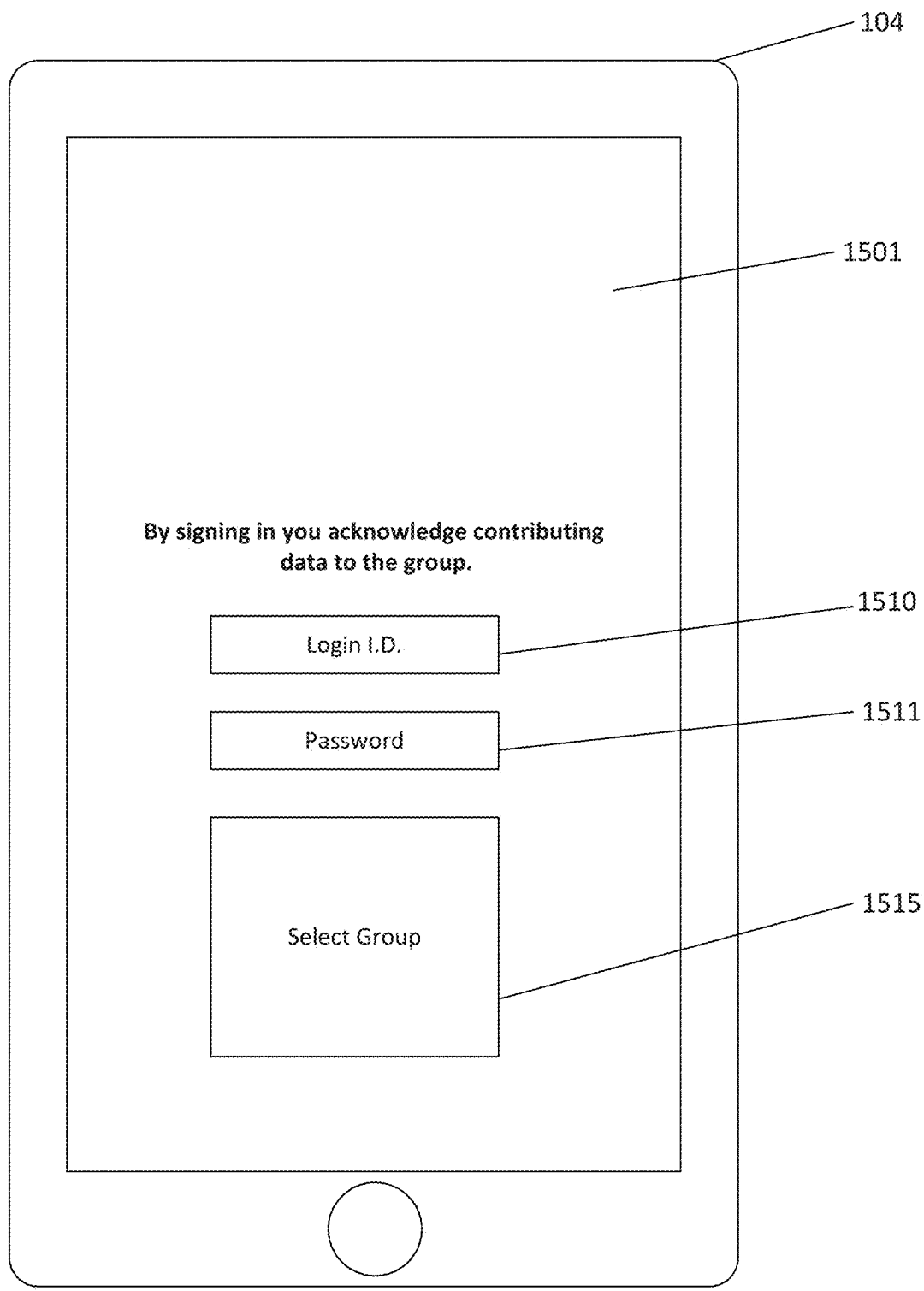
FIG. 15 illustrates an exemplary user acknowledgment screen of the software application.

Referring now to FIG. 15, an exemplary user acknowledgment screen 1501 generated by the software application 140 is shown displayed by the display screen of the multifunction device 104. The screen 1501 includes a login warning statement "By signing in you acknowledge contributing data to the group." The screen 1501 includes a login identification (I.D.) entry field 1510 and a password entry field 1511 that the user completes to log into the group vital signs server 1435. By logging in, the user acknowledges that they are contributing data to the group. The screen 1501 further includes a vital signs group selection field or menu 1515.

The group vital signs server login process provides extra security and reduces the chance that personal data will be shared inappropriately with a wrong group. The user controls what information is shared with the selected vital sign groups and has to authenticate their identification before sharing is allowed. The user's device 104 can then upload his/her data to the group vital signs server 1435. With user vital sign data uploaded to the selected vital signs groups, the group vital signs server 1435 can cluster reference curves of single vital sign measurements of different users together to provide group reference vital sign curves.

Each member of a vital signs group performs scans at different times throughout the day. Thus, a group vital signs curve plotted strictly by the time of day may not accurately portray the group's average. The group vital signs server 1435 may optionally time warp the individual vital sign curves by performing clustering algorithms around standard events that most people perform throughout the day, such as eating breakfast, lunch, and dinner. Time warping shifts the vital signs data in time to make the given vital sign scan data more relevant.

Another feature of the group vital signs server 1435 is the aggregation and clustering of reference vital sign curves of multiple vital sign measurements. Mathematically, this means that the group vital signs server 1435 clusters multidimensional data together, rather than clustering individual measurements independently. The aggregation and clustering of reference vital sign curves can provide a more accurate description of the base map of a certain group of people. For example, senior citizens with high blood pressure, diabetes and kidney conditions may be anonymously grouped together for comparison with a user having the same conditions.

Figure 16:
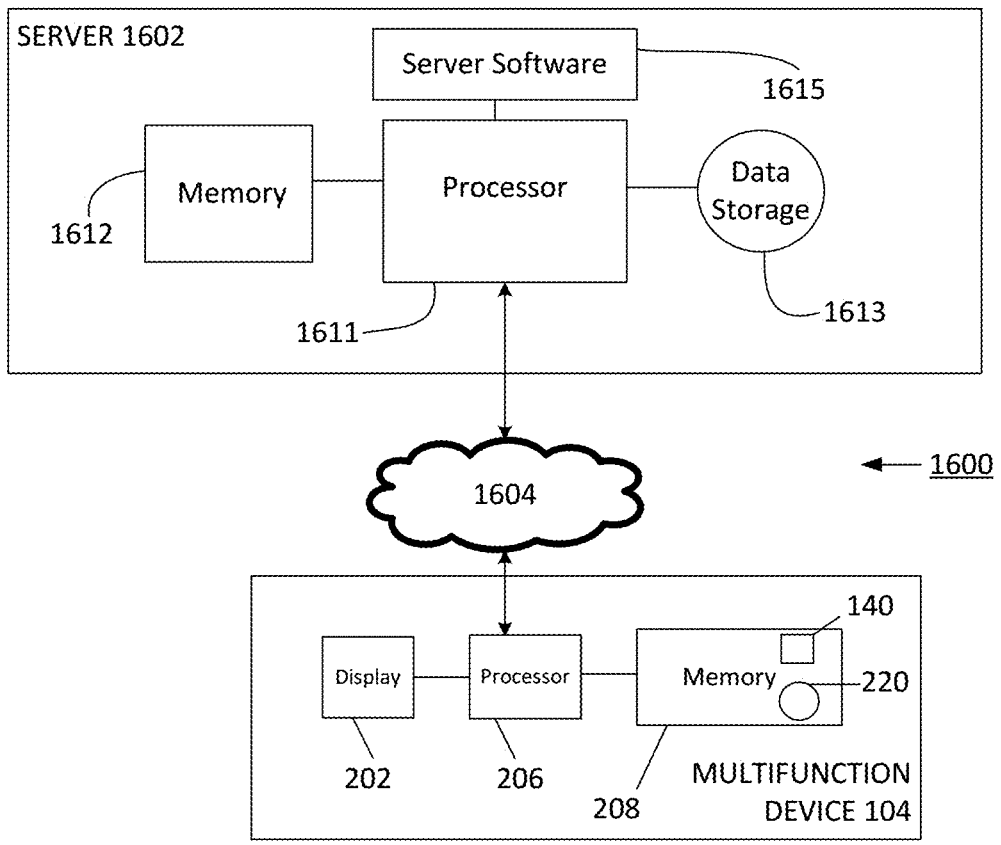
FIG. 16 is a functional diagram of the cloud based server system of an exemplary embodiment of the invention.

FIG. 16 is a functional diagram of a cloud based vital signs client server system 1600 in accordance with one embodiment of the invention. The vital signs client server system 1600 includes a server 1602 and one or more multifunction devices 104, the client, in communication with the server 1602 over an internet cloud 1604.

The server 1602 includes a processor 1611, a memory 1612, and one or more storage devices (e.g., hard disk drives) 1613 to store instructions of vital signs server software 1615 and vital signs data. The processor 1611 executes instructions of the vital signs server software 1615 to carry out a number of the server related functional processes described herein.

The portable multifunction device 104 includes a processor 206 and a non-volatile memory 208. The non-volatile memory 208 of the personal wireless digital device 104 may store the vital signs scanning software application 140 and the user data 220 related to the vital signs scanning software application. The processor 206 can read and write to the non-volatile memory 208 such that the vital signs scanning software application can provide a user interface to a user via the touch screen display device 202.

Processor 206 executes instructions of the vital signs scanning user interface (VSUI) software application 140. The VSUI software application 140 may include instructions for creating canonical vital signs curves, updating canonical vital signs curves with successive vital signs scan data, tagging vital signs scans, and periodically uploading vital signs data to the cloud and downloading group canonical curves.

Periodically, vital signs data may be transferred via the internet 1604 to the server 1602. Uploaded vital signs data may be stored in data storage devices 1613 and/or non-volatile server memory 1612. The vital signs server software 1615 may be executed by the processor 1611 to facilitate uploading and downloading of user vital signs data and group vital signs data.

Figure 17:
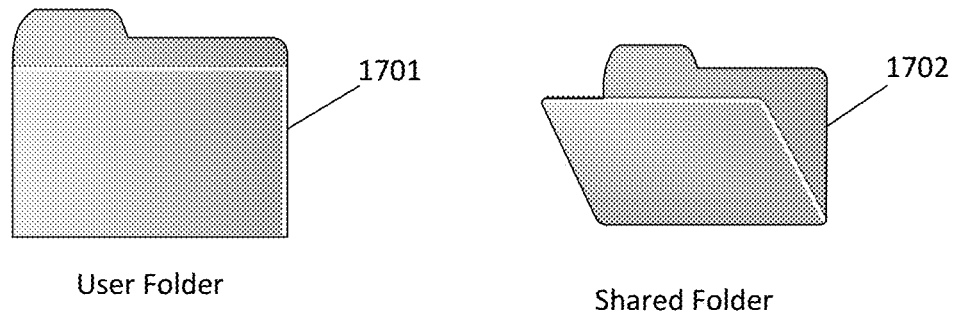
FIG. 17 illustrates an exemplary method of organizing the users data within a cloud system.

FIG. 17 illustrates an exemplary method of organizing the users data within a cloud system. Within the cloud data storage, a user may upload their data including personal data such as name, date of birth, address, infirmities, etc. into an encrypted user folder 1701. Within the cloud data storage may also be another folder 1702 that contains the user's shared vital signs data. All the data sent to the cloud data storage will be encrypted on the multifunctional device 104 before being sent to cloud. Only the user can decrypt their encrypted data using their specific multifunction device 104 or another device authorized by the user. The user can also authorize their PCPs to decrypt this data.

The data stored within the shared folder 1702 is medical grade data. This data is uploaded from the user's multifunction device 104 with full encryption and typically is not editable by the user. The user can choose and authorize whom they wish to share this data, for example, the user can share this data with their PCP and certain groups, but the user cannot edit this data. The user can also share their data with their groups, but preferably only non-identifying data would be shared with the group. For example, the group may receive the user's accumulated vital signs data along with the user's age, gender, and medical condition, but the user's name, address and other non-essential information would not be associated with this data. In either case, whether sharing with a PCP or with a group, the data is not editable by the user. A physician needs accurate unedited data to correctly diagnose the user and groups need accurate unedited data to form true vital sign group curves in order to provide all users with useful information.

FIG. 18 illustrates a diagram of a global group 1800 of users. The global group 1800 includes a plurality of vital sign groups 1802,18011,1812,1820 of a subset of users. A user may belong to one or more vital sign groups depending upon their condition. The user can choose to share their medical grade data with their groups. By belonging to a group, the user receives group canonical vital signs curve data formed from the crowd-sourced data of the groups.

Figure 11C:
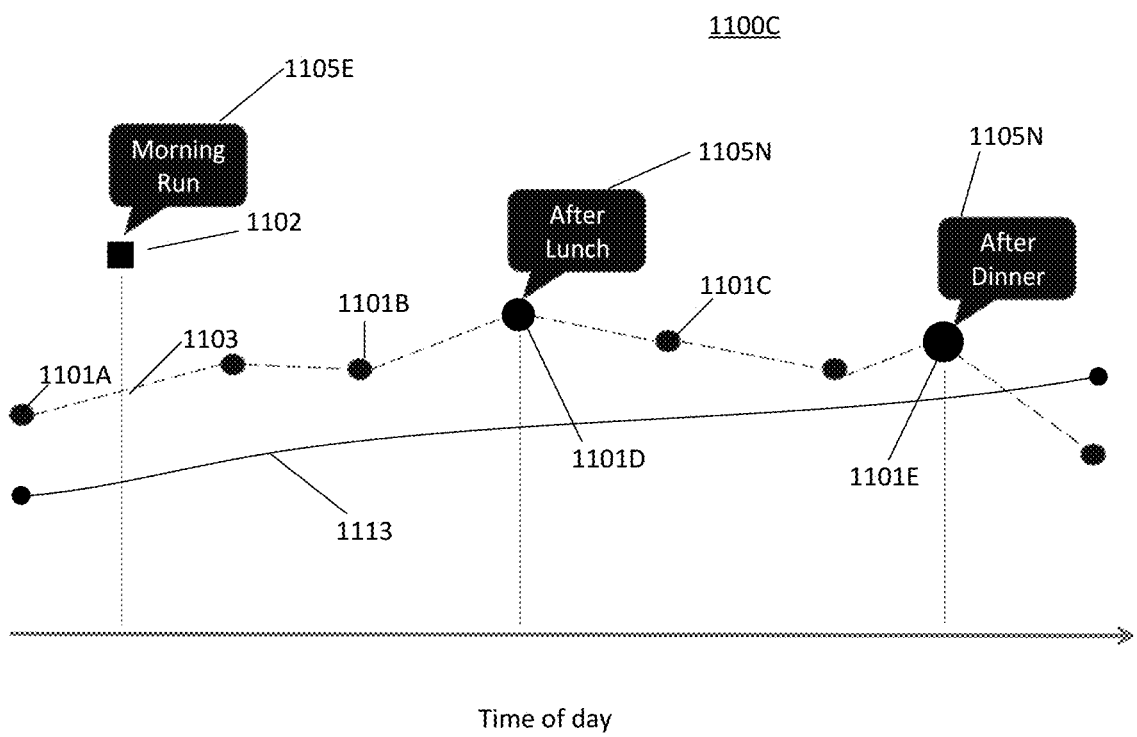
FIG. 11C illustrates a vital sign curve of a vital signs group plotted against a users vital sign curve shown in FIG. 11A over a twenty four hour period.
Figure 11D:
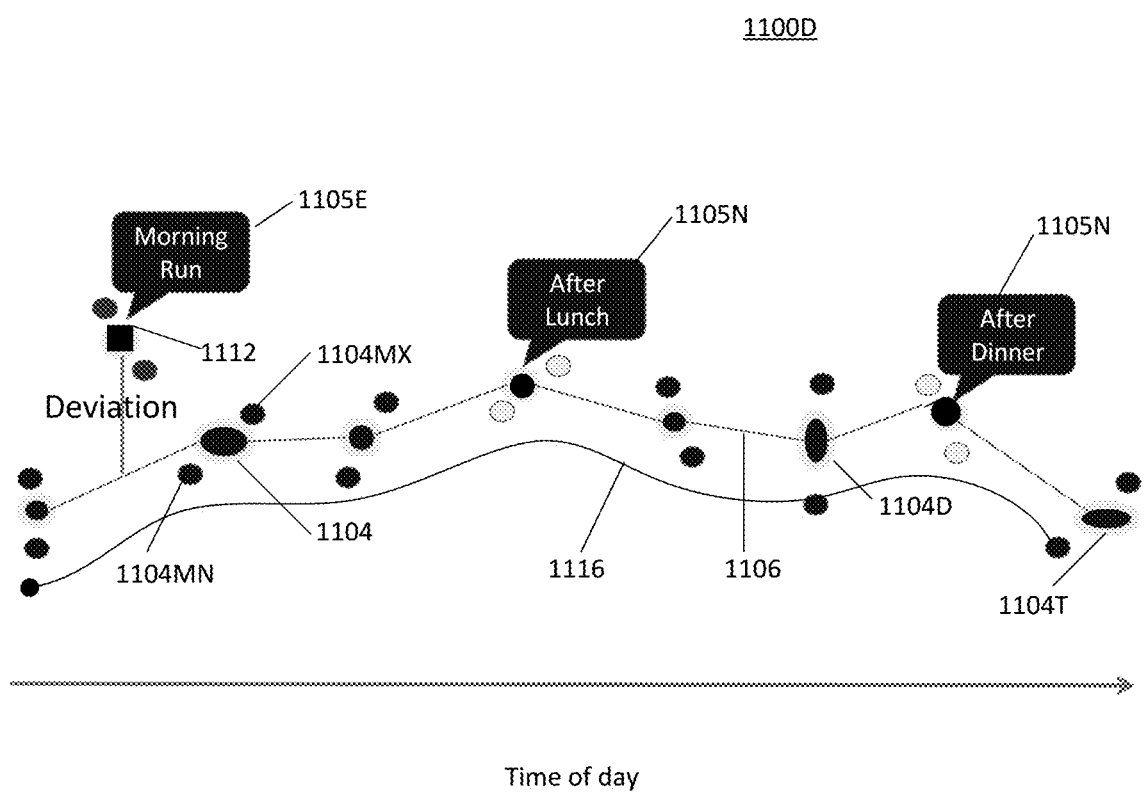
FIG. 11D illustrates a group canonical vital sign curve of a vital signs group plotted against the user's canonical average vital sign curve shown in FIG. 11B.

Group canonical curves can be compared with a users personal canonical vital signs curves. As illustrated in FIG. 11C, the multifunction device 104 can display on its display screen a chart of both a days vital signs curve 1103 and a group canonical curve 1113 for the same vital sign. A user can visually compare the curves to see the difference between them. As illustrated in FIG. 11D, the multifunction device 104 can display on its display screen a chart of both the user's canonical average curve 1106 and a group canonical curve 1116 for the same vital sign. The user again can visually compare the curves displayed on the display screen to see differences between them.

In some cases, the difference between a users curve 1103,1106 and the group curve 1113,1116 may be beneficial, such as in the case of lower blood pressure for example. In other cases, the difference between curves may be detrimental, such as in the case of higher blood pressure for example. From differences between the user data and the group data, conclusions or observations may be automatically made by the vital signs software application 140 and shared with the user and/or his doctor or primary care provider.

The comparison of the user's personal canonical vital signs curves and the group canonical curves can be used by the user to better understand his/her basic health condition. The comparison of the users personal canonical vital signs curves and the group canonical curves can be used by a doctor to help make a diagnosis of the user, if needed. Group vital signs information from the group vital signs server may be made valuable to doctors and public health professionals to monitor current trends in vital signs groups. The vital signs software application 140 may provide specific recommendations to the user (e.g., take more vital signs scans with the vital signs scanner 102 to gather additional vital signs data) based on the user's affiliation with one or more vital signs groups.

Figure 19:
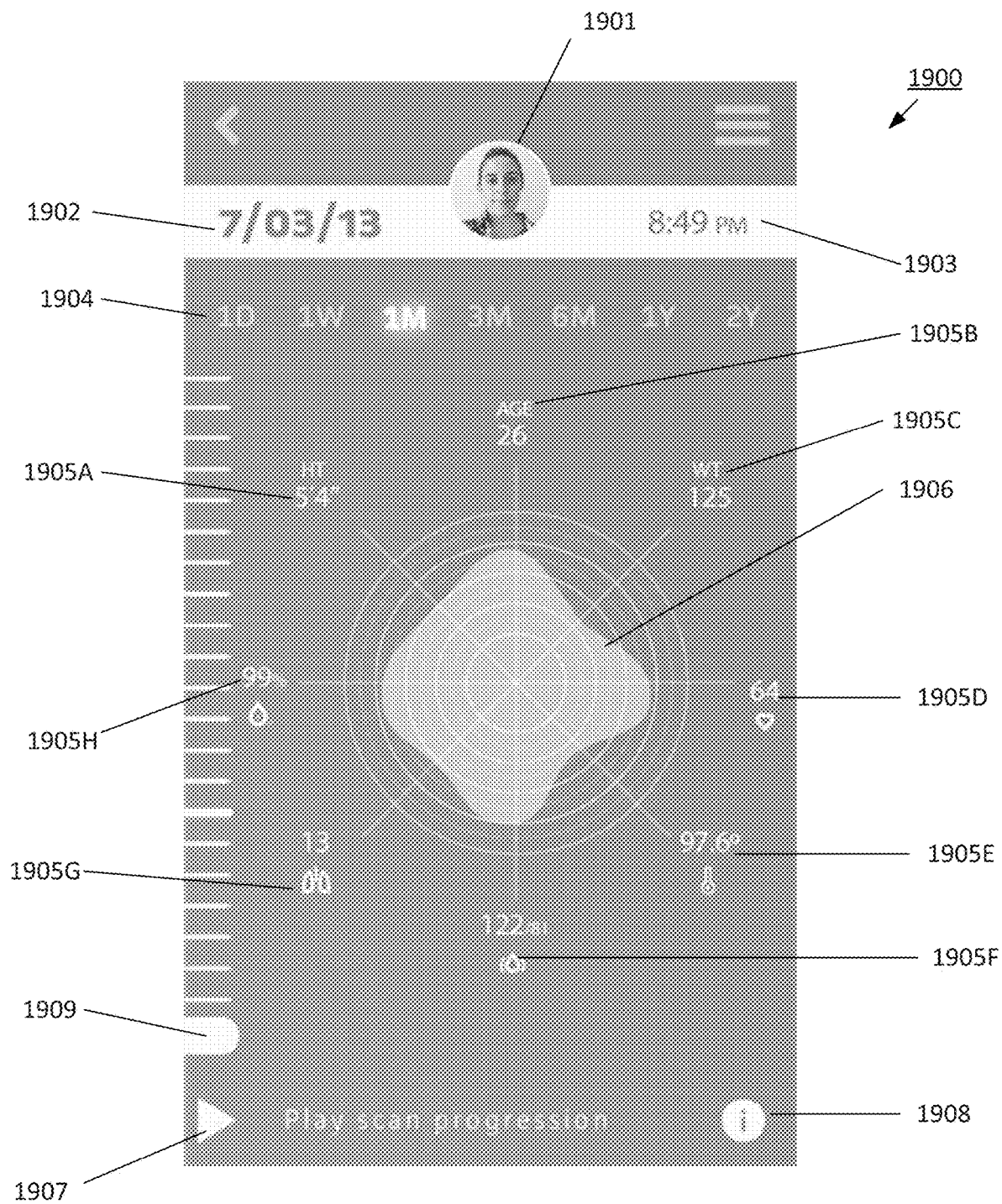
FIG. 19 is an exemplary graph of the users vital signs.

FIGS. 11A-11B illustrate static graphs for a single vital sign of a user. FIG. 19 illustrates an alternate way to display multiple vital signs of a users vital sign history in an easy to read comprehensive manner by using a dynamic multidimensional graph.

Referring now to FIG. 19, a user interface 1900 is displayed on a display device of the multifunction device 104. The user interface 1900 includes an exemplary multidimensional graph 1906 of a user's vital signs. The users vital signs are indicated along a plurality of axes or spokes radiating out from a center point with a curve being formed from values between each spoke. The multidimensional graph resembles a spider web and is often referred to as a spider graph 1906. The spider graph 1906 also allows the user to see their vital signs dynamically change over a selectable progression of time or history.

The user interface 1900 further includes a profile icon 1901 that may be the user's photo or some other icon or avatar chosen by the user. The profile icon 1901 identifies the user so that multiple users of a multifunction device 104 are aware of whose profile they are viewing. The user interface 1900 further includes a date display 1902 and a time display 1903 of the present date and time and may be provided by the multifunction device's calendar function.

The user interface 1900 further includes an interval bar 1904 that shows the user which progression interval is currently being displayed by the user interface. The progression interval of vital signs that may be displayed are for vital sign scans within a predetermined period of time such as one day (1D icon), one week (1 W icon), one month (1M icon), three months (3M icon), six months (6M icon), one year (1Y icon), or two years (2Y icon) for example. The interval bar 1904 may allow selection of the progression interval by touching the icon for the predetermined interval. For example, the 1M icon may be touched in the touch sensitive display screen such that the progression interval is one month. The 1M icon is highlighted to indicate it is the progression interval that is desired to be displayed. In this case, the progression of vital signs displayed are within one month of the date 1902 as shown by the highlighted 1M icon.

Underneath the interval bar 1904, and forming axes of the spider graph 1906 are user characteristics and selected vital signs data.

The three user characteristics shown in the upper hemisphere of the graph 1906 are height 1905A, age 1905B, and weight 1905C that may be obtained by user input or by interfacing with other components, such as an electronic scale. If the multifunction device is equipped with a camera, another application may be able to photograph the user next to a linear chart and automatically derive the user's height by comparison to the linear scale. The users age may be calculated from the present date 1902 and the users date of birth input into the software application 140.

The other characteristics 1905D-1905H plotted along the other spokes or axes of the graph 1906 are vital signs obtained by the user through the use of the vital signs scanner 102. Each vital sign is shown as a number and an icon representing the vital sign measured. For example, 1905D shows a heart representing the users heart rate and 1905E shows a thermometer representing the users body temperature. The position of these characteristics around the cardinal axis can be rearranged based on the users choice. The graph 1906 is an amalgam of the different user characteristics or vital signs 1905A-1905H.

The user interface 1900 may further include a slider bar 1909 that changes or selects a predetermined time of day about which information is desired. The user may slide the slider bar 1909 to select the measurement at a particular time of day that are desired for display. For example, a user may want to display measurements of vital signs data for vital sign scans that occurred around 8 P.M.

Play button 1907 activates the progression. When the progression is activated the software application 140 displays the change in the characteristics 1905A-1905H over the period of time selected. Certain characteristics just as age and height are likely to remain unchanged over the period of one month, but other vital signs may be more dynamic. The spider graph allows the user to visually see the change in their vital signs over a period of time. If the shape of the user's spider graph changes drastically, the user is more likely to be alerted to the change than if the results were displayed only numerically in a list.

A group vital sign curve 1950 of a plurality of vital signs associated with a vital signs group may also be displayed along the axes of the spider graph. The group vital sign curve 1950 selected by the user for comparison remains fixed as the user vital sign curve 1906 progresses over the selected period of time.

Figure 20:
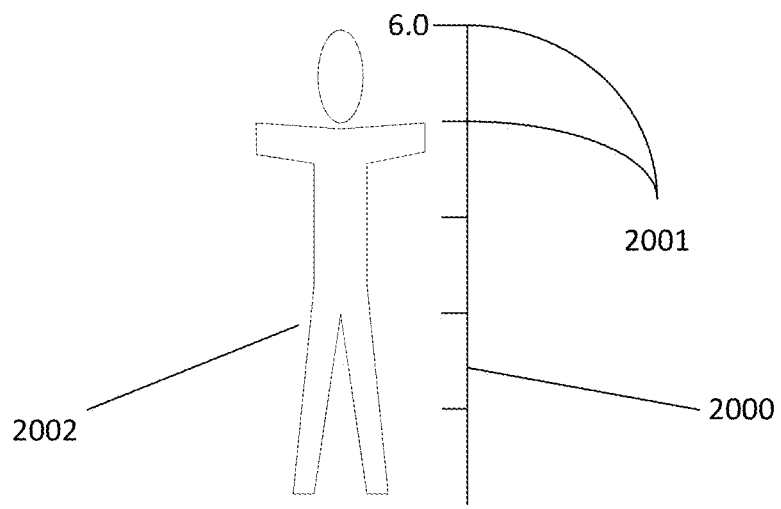
FIGS. 20 and 21 illustrate automated methods of obtaining a users height and weight.
Figure 21:
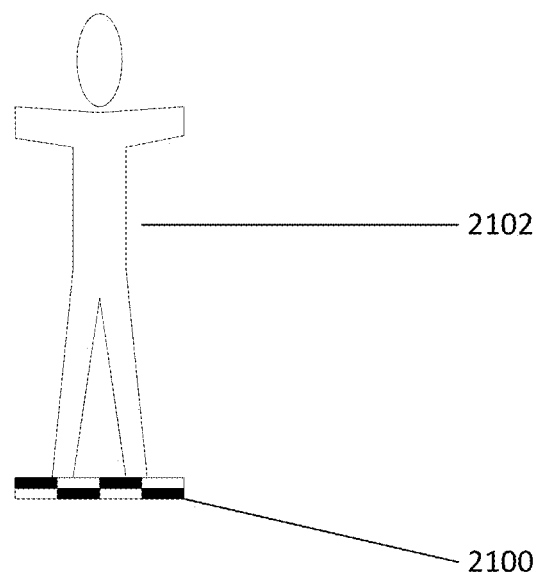

FIGS. 20 and 21 illustrate methods of automatically obtaining the user's height and weight, without needing manual input by the user. Regardless, the user's height and weight may be measured manually and manually input into the vital signs software application 140 and associated with the given date and time.

In FIG. 20, the user 2002 is illustrated standing next to a linear chart 2000. A photograph function on the user's multifunction device 140 can be used to photograph the user 2002 standing next to markings 2001 on the linear chart 2000. A third party application linked to the vital signs software application 140 or a sub-routine in the vital signs software application 140 may derive the user's height by comparison of the user's body position with the respect to the markings on the linear chart. Detecting the end point of the user's head against the marking on the linear chart 2000 indicates the height measurement of the user 2002. The height measurement is then reported to the vital signs software application 140 to be recorded as a characteristic of the user. The height measurement may change over time, particularly in younger users of the vital signs software application.

Referring to FIG. 21, a user's weight may be automatically measured and reported to the vital signs software application 140 as a user characteristic. A user 2102 stands on an electronic scale 2100 as shown in FIG. 21. The electronic scale 2100 is in communication with the multi-function device 104 and the vital signs scanning software 140. The electronic scale 2100 measures the user's weight each time the user 2102 steps on the scale 2100 and communicates each weight measurement to the vital signs software application 140. Each weight measurement for the user 2102 can be time stamped with date/time and recorded by the software application 140 for inclusion as a user characteristic and monitored vital sign. One can expect that a users weight varies over the user's age and date/time and can generally have an influence on a user's health.

Medical Records

Figure 22A:
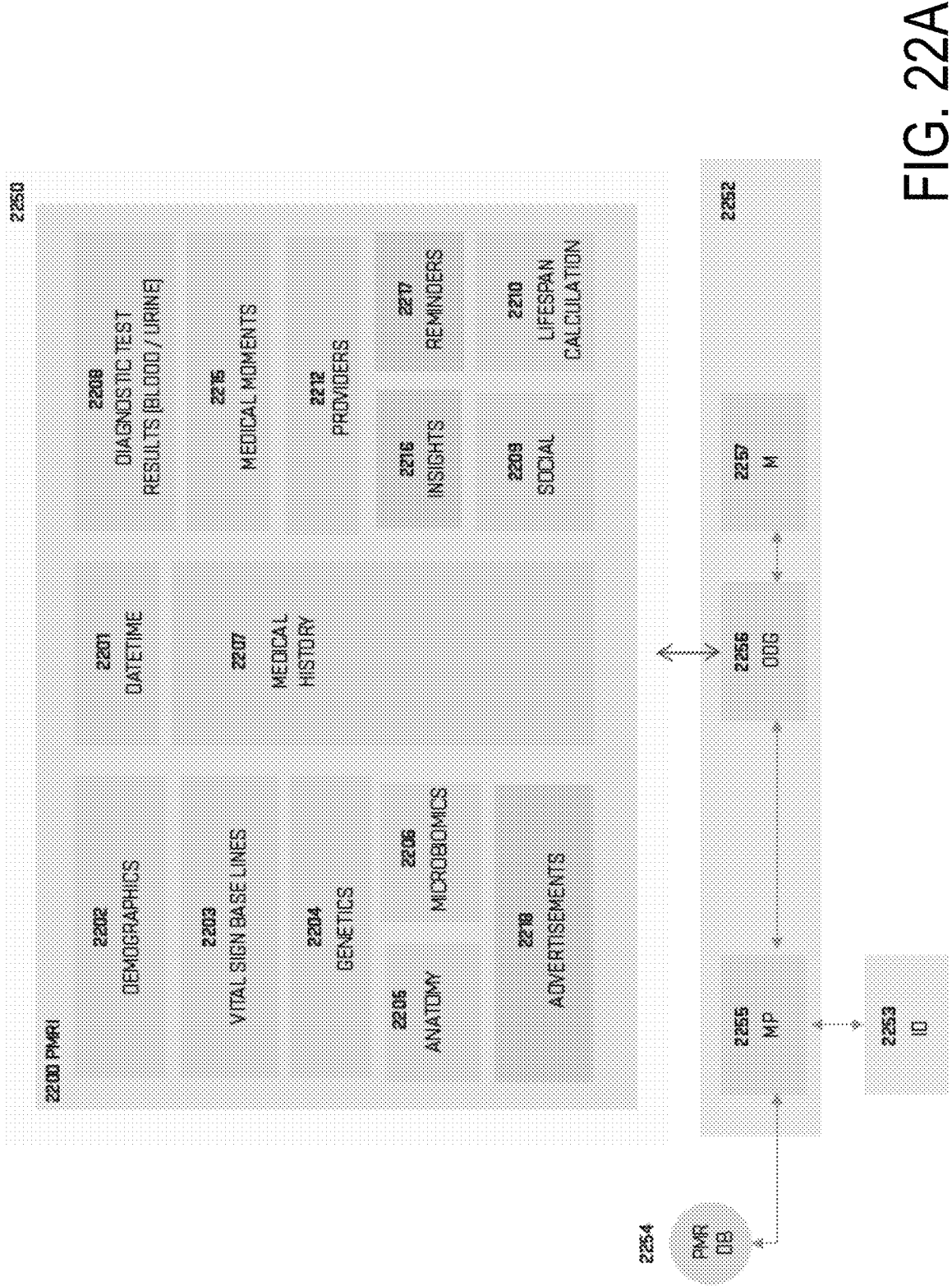
FIG. 22A illustrates a personal medical record displayed on a display device of a computer or other electronic device.

Referring now to FIG. 22A, a personal medical record (PMRi) 2200 for an individual at an $i^{th}$ given date and time 2201 is shown displayed by a display device 2250. The display device 2250 may be a non-touch screen display device, or a touch-screen display device (to also accept user input) of an electronic device, such as the touch screen display device 202 of the portable electronic device 104 shown in FIG. 2A. The display device 2250 may interface to a personal medical records data base (PMRDB) 2254 in the cloud through a computing device 2252 such as a computer server (e.g., server 1030 shown in FIG. 10, server 1435 shown in FIG. 14, or server 1602 shown in FIG. 16) or other electronic device to display the personal medical record. The computing device 2252 includes a processor 2255, a display device controller 2256, and a storage device 2257 (e.g., memory). The personal medical record (PMRi) 2200 may be formatted over one or more pages/screens to fit various display screens, such as large format computer display screens and small format smart phone display screens as a mobile personal medical record.

Medical record data may be input into the data base 2254 by an input device (ID) 2253 or a touch screen of a touch screen display device 2250, such as the touch screen display device 202 of the portable electronic device 104 shown in FIG. 2A for example. In other cases, the medical record data associated with the user is automatically populated into the fields of the personal medical record as it is received into the database. The data base 2254 stores personal medical records of a user so that it can be used to recall medical record history over time and dates.

The user can not only read his/her personal medical record (PMRi) 2200 but also help construct it through a collaboration by causing information to be written into the data fields therein. Some of the information can be self aggregated or automatically populated into the data fields of the personal medical record (PMRi) 2200, referred to as self aggregated data. In other cases, some of the data fields in the personal medical record (PMRi) 2200 are populated by querying the user for information (simple questions) over time and manual entry of that information by the user. One question follows the other in a logical sequence, as a caregiver (e.g., doctor, nurse) proceeds to categorize and sub-categorize patients. These user questions may be context based adapting in that they are responsive to one or more characteristics of the user, such as age and sex (gender). For example, younger users may not be concerned with colonoscopy testing until the age of 45. As another example, female users may be asked demographic questions regarding pregnancy while male users would not.

Moreover, the user questions are more explanatory by explaining medical terminology and expanding medical acronyms in layman terms if possible. Similarly, explanations are provided in layman terms when possible about the personal medical record and the information stored therein to educate the uninformed user in health care, so they can be more proactive and be in better control of his/her own health care. The personal medical record is user friendly to those users not well versed in medical or health care. Moreover, the personal medical record provides a means of training a user in health care in order to better care for their own personal health.

In other cases, the user may select a data field with a user input device, such as a mouse click of a mouse button or touch on a touch screen over the data field, and manually enter or update information in the data field. Additionally, the user may associate backup files (e.g., photographs, diagnostic test results, x-ray scan data, magnetic resonance imaging scan data, etc.) by uploading it and associating it with a data field in the personal medical record (PMRi).

Some of the data fields in the personal medical record (PMRi) 2200 of the user are automatically populated by service providers (e.g., laboratory testing) after evaluation or tests are run, with or without backup. Some of the data fields are automatically populated by devices (e.g., vital signs scanner, urine scanner, blood scanner, tooth brush, weight scale) that the user uses to capture information for the data fields in the personal medical record.

The personal medical record (PMRi) 2200 may have access to user pharmacy information and prescriptions being filled, access to user hospital records and procedures that are undertaken; and access to user genomics of DNA sequencing that are undertaken of the user biological cells. To better integrate with diet and fitness applications, the personal medical record (PMRi) 2200 may have access to an application programming interface, such as Apple's Healthkit for Apple iOS.

Figure 30:
FIG. 30 is a chart illustrating an example of life expectancy information for a given user.

Referring now to FIGS. 29-30, a key parameter of the personal medical record (PMRi) 2200 may be actuarial information (life expectancy data/information). An actuarial equation may give weightings to particular data/parameters (life expectancy parameters) input in the personal medical record and the personal medical records data base associated with the user. The actuarial equation can then calculate the users life expectancy and probable cause of death in response to the weighted life expectancy parameters. The users calculated life expectancy may be used to associate the user with quartiles, lower, median, and upper, each of which have an age prediction and odds/probability associated with the predicted age. For example, a given user may be computed to be in the lower quartile at an expected age of 73.90 years with a 75% probability of living longer. A median expected age is 82.32 years old with a 50% probability of living longer. An upper expected age is 89.31 years old with a 25% probability of living longer. A life extension age may be computed if set health goals are met by the user. For example, if health goals are met, a user can expect to extend his life to a life extension age of 95 years old. If health goals are not met, a user would not expect an increase in the life expectancy age. If a person regularly exercises performing a physical activity, a positive health benefit for example, the life expectancy calculator can show an increase in life extension. Without regular exercise, a user would not expect an increase in the life expectancy age.

Obviously, if a user undertakes adverse health behavior, such as smoking cigarettes, drinking alcohol, poor eating habits (nutrition), multiple sex partners, lack of sleep for example; a user should expect a decrease in the life expectancy age. The life expectancy calculator can calculate and show a lower life expectancy age as a result of such adverse health behavior. Furthermore, if a user undertakes risky behavior such as a particular job occupation (e.g., deep sea diver, sky diving), undergoes life stress/depression, or undertakes hazardous behavior such as regularly driving a car long distances each year, the life expectancy calculator can also consider such behavior/incidents and calculate a lower life expectancy age.

A mortality table, a table of probably death rates for males and females as a function of age, may be used to determine a basic life expectancy age for a person of a given age. Then health goals, health risks, health behavior making up a plurality of positive life expectancy factors, along with the risky behavior making up a plurality of negative life expectancy factors, can be weighted to the particular user such that the life expectancy age of the particular user can be calculated by the life expectancy calculator. The life expectancy calculator may weight and sum some the positive and negative life expectancy factors and/or weight and multiple some the positive and negative life expectancy factors to the basic life expectancy age of the user given a particular age. Appendix I of U.S. provisional patent application No. 62/286,310 filed on Jan. 22, 2016 and incorporated herein by reference, illustrates an exemplary actuarial equation, exemplary mortality table, and how some life expectancy factors may be used by a life expectancy age calculator to determine the life expectancy age of a given user. Appendix II of U.S. provisional patent application No. 62/286,310 filed on Jan. 22, 2016 and incorporated herein by reference, indicates a plurality of life expectancy parameters (e.g., education level, ethnicity, gender, blood type, average vital signs over time (heart rate, heart rate variability, oxygenation, blood pressure), health screenings, primary care consultations, colonoscopy, gastroscopy, pulmonary checks, bowel movements, religion/beliefs participation, physical activity, medications, vitamins, herbs, supplements, hormones, sleep, traumatic stress, health plan level/insurance, etc.) in conjunction with the age of the user that may be considered by the actuarial equation of the life expectancy calculator and the expected variance on life expectancy age. Generally, the older the user (greater age) currently is, the more of these factors may be considered by the actuarial equation of the life expectancy calculator and the expected variance on life expectancy age. Thus, the actuarial equation used by the life expectancy calculator can vary as the user ages and alter the calculated life expectancy.

Figure 28:
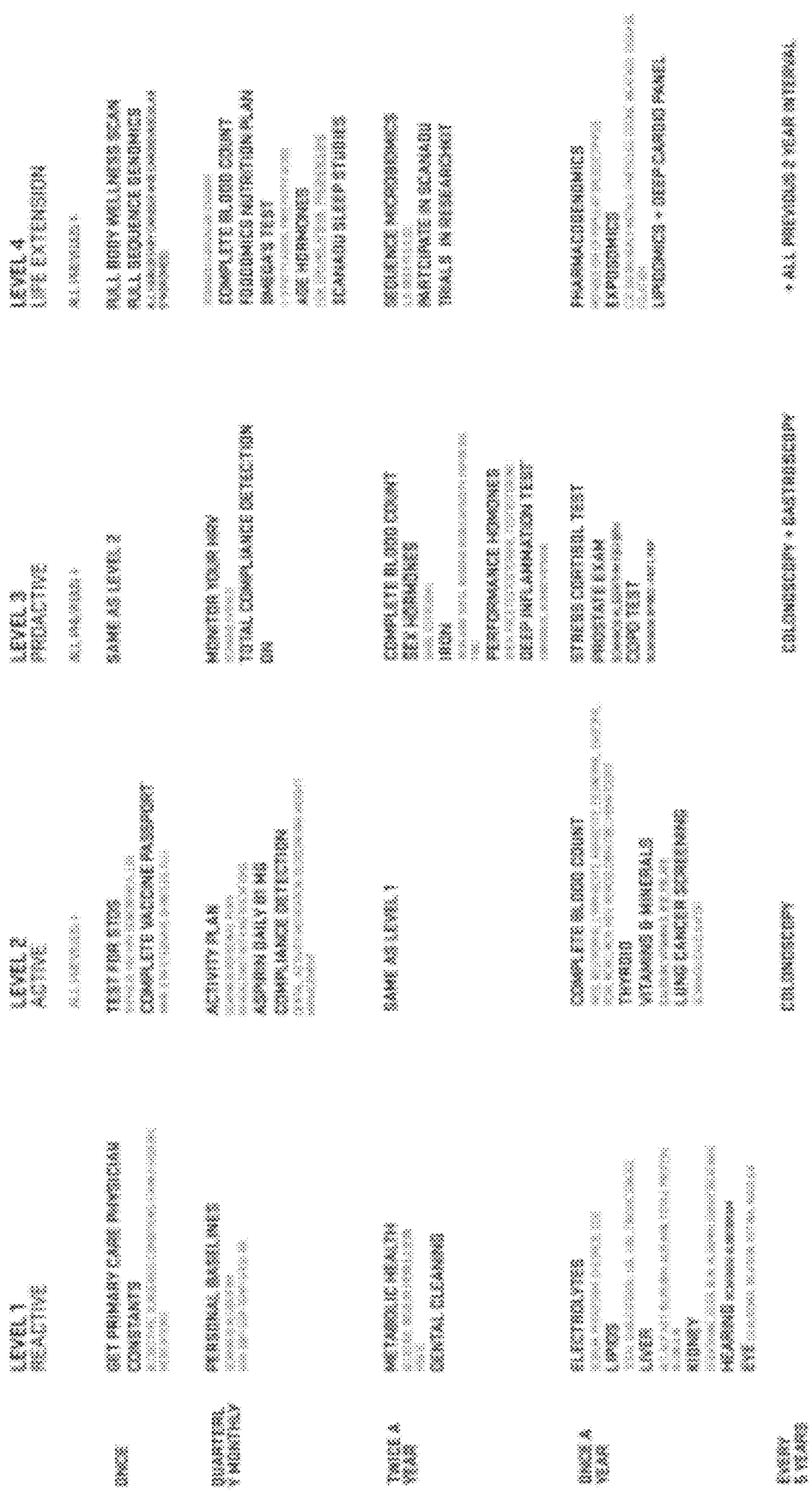
FIG. 28 illustrates a chart of progressively more aggressive levels of health care plans that may be associated with the personal medical record.

The personal medical record (PMRi) 2200 may be driven by a personal health plan which can be reactive (level 1), active (level 2), proactive (level 3), or a plan for life extension (level 4), each level having additional requirements to the previous one, such as shown in FIG. 28, for example. The goals set and the compliance thereof may be based on this personal health plan. Personal baselines (range of values) of the parameters in the record may be indicated below the latest value captured for that parameter in the PMRi 2200 for visional comparison by the user. Furthermore, average baselines for the parameters may be determined from all participating users in the personal medical record system. These may be indicated in the personal medical record near the value of the parameter displayed for a given user. In this manner, the given user can visually compare his latest value and baseline range for the parameter against the average baseline range from all participants.

One objective of the personal medical record 2200 is to give consumers control over their health. Actuarial science allows users to assess health risks of given health parameters or life expectancy parameters. The health risks of the parameters are built in to the personal medical record system, dynamically changing, allowing users to set and/or adjust their goals to lead to a healthier life in real time.

The personal medical record (PMRi) 2200 may be generated by a mobile personal medical record application executed by an electronic device, such as a smart phone. A plurality of personal health plans, one of which is chosen by the user, may be tied into the personal medical record (PMRi) 2200. For example, the plurality of personal health plans may include reactive (Level 1), active (Level 2), proactive (Level 3), and life extension (Level 4), such as show in FIG. 28. As the health plan varies, different goals set for the health and medical record parameters can change along with additional parameters being added as levels increase. The mobile personal medical record application performs compliance detection of the goals set for the health and medical record parameters and visually indicates in the personal medical record if the user is meeting or failing to meet the goals with the values being captured.

The personal health plan chosen by the user may change over time as the user ages, such as from Level 1 reacting at a young age to Level 4 Life Extension at older ages. Health care strategy can be dynamically built in real time and displayed in the personal medical record by the personal medical record application. The personal medical record (PMRi) 2200 can on the fly adapt to the change in plans and how the user ages. The personal medical record (PMRi) 2200 can include diet information (e.g., daily calorie, daily fat intake) and exercise or fitness information (e.g., number and type of daily workouts, distance ran/swam/biked, and calories burned) or be associated to other applications that obtain measures of diet and fitness.

For example, with reference to FIG. 28, in the reactive plan one may select to a primary care physician (offline or online); Use a vital signs scanner and vitals signs algorithm to determine your personal baselines; Twice a year—test your metabolic health including glucose, insulin, hemoglobin hba1c levels; Once a year—test your electrolytes: (sodium, potassium, chloride, co2); Once a year—test your lipids (total cholesterol: ldl, hdl, triglycerides); Once a year—test liver (alt, alp, ast, bilirubin, albumin, total protein, globulin); Once a year—test kidney (creatinine, egfr, bun, albumin, bun/creatinine); Once a year take an eye exam (glaucoma, dilation, retina, macula); Once a year do a hearing exam (audiogram) 10.twice a year go for dental cleaning.

For example, in the active healthcare plan the user would once a year—do a complete blood count (wbc, neutrophil, lymphocyte, monocyte, eosinophil, basophil, rdw, mchc, mch, mcv, hemoglobin, rbc, hematocrit, immature granulocyte); Once a year—test thyroid (tsh); Once and for all: test for stds (syphilis class a and b, hiv, gonorrhea, lgv); Complete your vaccines (mmr, dtap (tedivax), shingles, flu); Do a snip genetic test (23&me); Once a year—measure your calcium, vitamin d, b12, folate; Daily —take one baby aspirin (81 mg) for the rest of your life; Once a year—use a cancer calculator to see if you need a lung cancer x-ray; Every five years a colonoscopy; and All the year—choose an activity plan (in healthkit with notifications).

For example, in the pro-active healthcare plan one may do all the previous mentioned blood tests twice a year; Add test for your stress: cortisol and a complete deep cardio panel (lipids); Prostate exam: calculator bph, physical exam, psa; Use the spirometer for copd test (fev1, fef); Twice a year—test your iron: iron and total binding iron capacity, ferritin, tibc; Twice a year—test your performance hormones: dhea, free testosterone, testosterone; Twice a year—test your sex hormones: shbg, estrodial; Start monitoring your hrv; Twice a year—measure deep inflammation: fibrogen, homocysteine; and Do an EKG.

For example, in the life extension healthcare plan one may do every blood test every quarter and make a plan with goals to improve the values; Full sequence genome (all hereditary cancer and cardiovascular syndromes); Sequence the microbiomics of gut and mouth twice a year; Engage pharmacogenomics: metabolism of popular drugs (cyp450); Study your exposomics (cdc db on heavy metals, particles, ozone, weather-disease relation); Do full allergy test panel; Actively follow your clinical nutrition plan; Every quarter add tests for omega's: o-3 fatty acids, free fatty acids and age hormones: hgh, epo, melatonin, pregnenolone; Parse your sleep and improve the rem values; and Go for a full-body wellness scan once.

Figure 25:
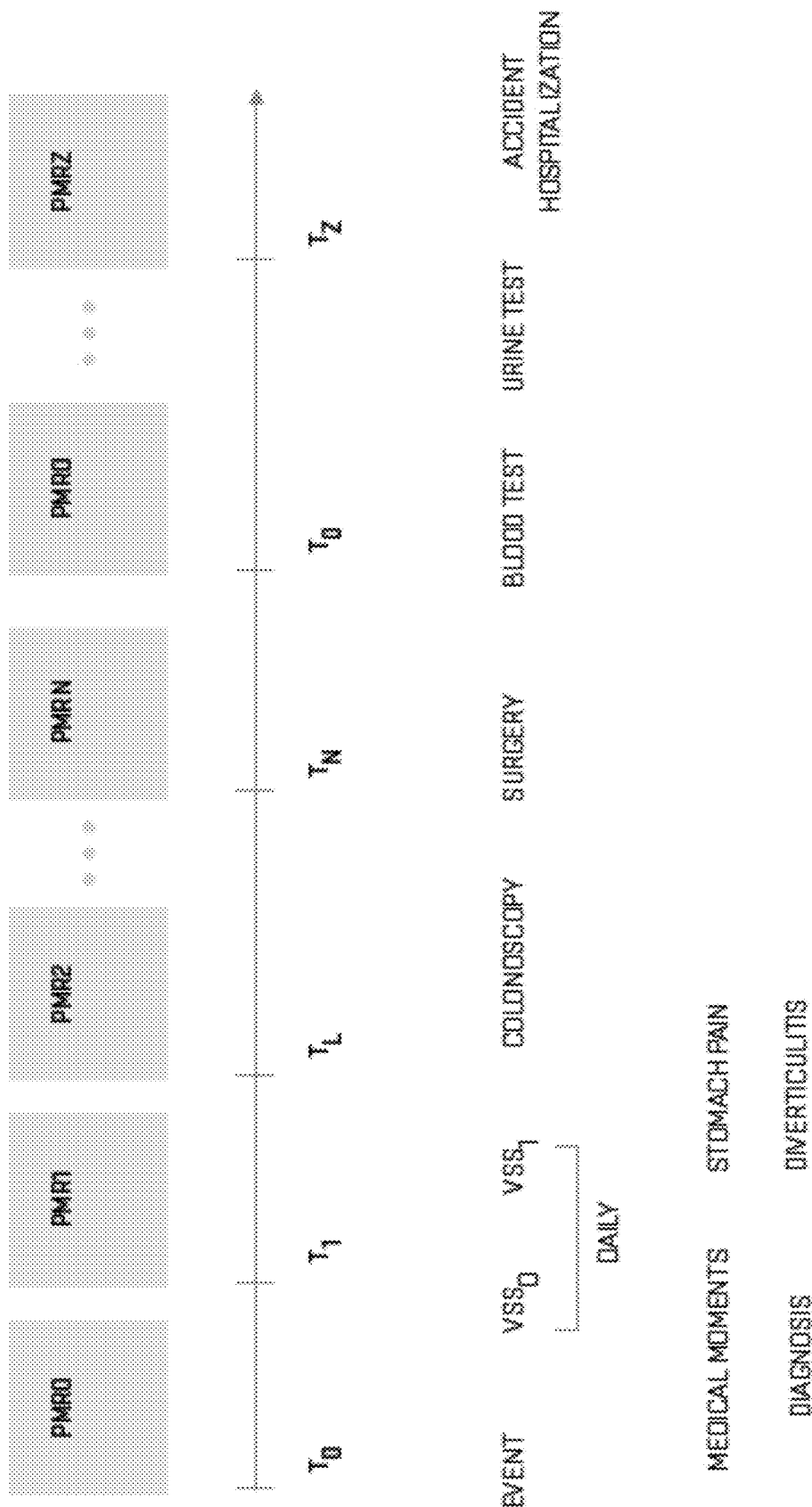
FIG. 25 illustrates a historical timeline of personal medical records that can be stored in a server.

Referring now to FIG. 25, a time line of personal medical record history is shown for different times/dates from time/date T0 to time/date TZ. A snapshot of the personal medical record is captured for different events, such as daily vital sign scans PMR0, PMR1 (e.g., VSS0 and VSS1 at times/dates T0 and T1 respectively; colonoscopy PMR2 (at time/date T2); surgery and/or child birth PMRN (at time/date TN); diagnostic tests PMRO (at TO); or an accident/hospitalization PMRZ (at time/date TZ).

The personal medical record (PMRi) 2200 is a nonlinear dynamic system. The entry parameters are dynamic and can change in real time as new information/data becomes available. Average baselines and ranges for the parameters may be used for comparison purposes against the users parameters to determine a measure of health of the use. Computations can be performed over the medical record history of the stored personal medical records in the database to determine health improvement, health degradation, and life expectancy of a user over time. The display device 2250 can display a personal medical record 2200 in response to receiving medical record data from the data base 2254.

Referring now to FIG. 22A, the single personal medical record PMRi 2200 includes, without limitation, the following information: demographics 2202, vital sign baselines 2203, genetics 2204, anatomy information 2205, microbiomic information 2206, medical history 2207, diagnostic test results (blood/urine test results) 2208, medical moments 2215, health or medical care service providers 2212, social data 2209, and a life expectancy/mortality calculation 2210. The life expectancy/mortality calculation may be based on the Wharton Mortality Calculator in response to information in the personal medical records. The personal medical record PMRi 2200 may further include medical insights 2216, medical/health appointment reminders 2217, and medical advertisements 2218.

The medical insights 2216 may be in response to medical moments 2215, trends or other data analysis of the data in the personal medical record. The medical insights may be indicative of a likely or potential medical, health, and/or wellness condition or issue (or indicative of an impending medical, health, and/or wellness condition or issue), which requires subsequent action. The medical insights may be any of a condition, a potential condition, an elimination of a potential condition, an analysis, a severity of a condition, a severity of a potential condition, a relevancy of a condition, a recommendation, medical data, health data, wellness data, or any combination thereof. The medical insights are created and provided to the user for informational purposes as well as to present an action plan/recommendation. For example, the recommendation may include at least one of the following: a recommendation for further analysis, a recommendation for further monitoring, a recommendation for medical consultation, a recommendation for tele-medical consultation, a recommendation for an in person consultation, a recommendation for urgent care, a recommendation for emergency care, a recommendation for further assistance, a recommendation including further information, a recommendation including health data, a recommendation including wellness data, or any combination thereof. Therefore, the user is provided with a plan for the further handling or management of the actual or potential medical, health, and/or wellness issue.

After analysis, a recommendation may be associated with a timing issue or a need for urgent care. Accordingly, the recommendation can be associated with an alarm of some type, such as an audible alarm, a visual alarm, a tactile alarm, a message, an audible message, a visual message, a tactile message, an indicator that attracts a user's attention, or any combination thereof. This helps to be sure the user is aware that some action should be taken. In some cases, the alarm may be transmitted as message to a hospital, doctor's office, or other health services location.

The reminders 2217 are date/time appointments for meeting with a doctor (physician), a care-giver, or a lab technician such as for a diagnosis, test, surgery or other treatment. The medical advertisements 2218 may be for relevant medical products, devices, and services that could be used with the medical record or otherwise to reduce the usage/support costs of the database of personal medical records.

Figure 22B:
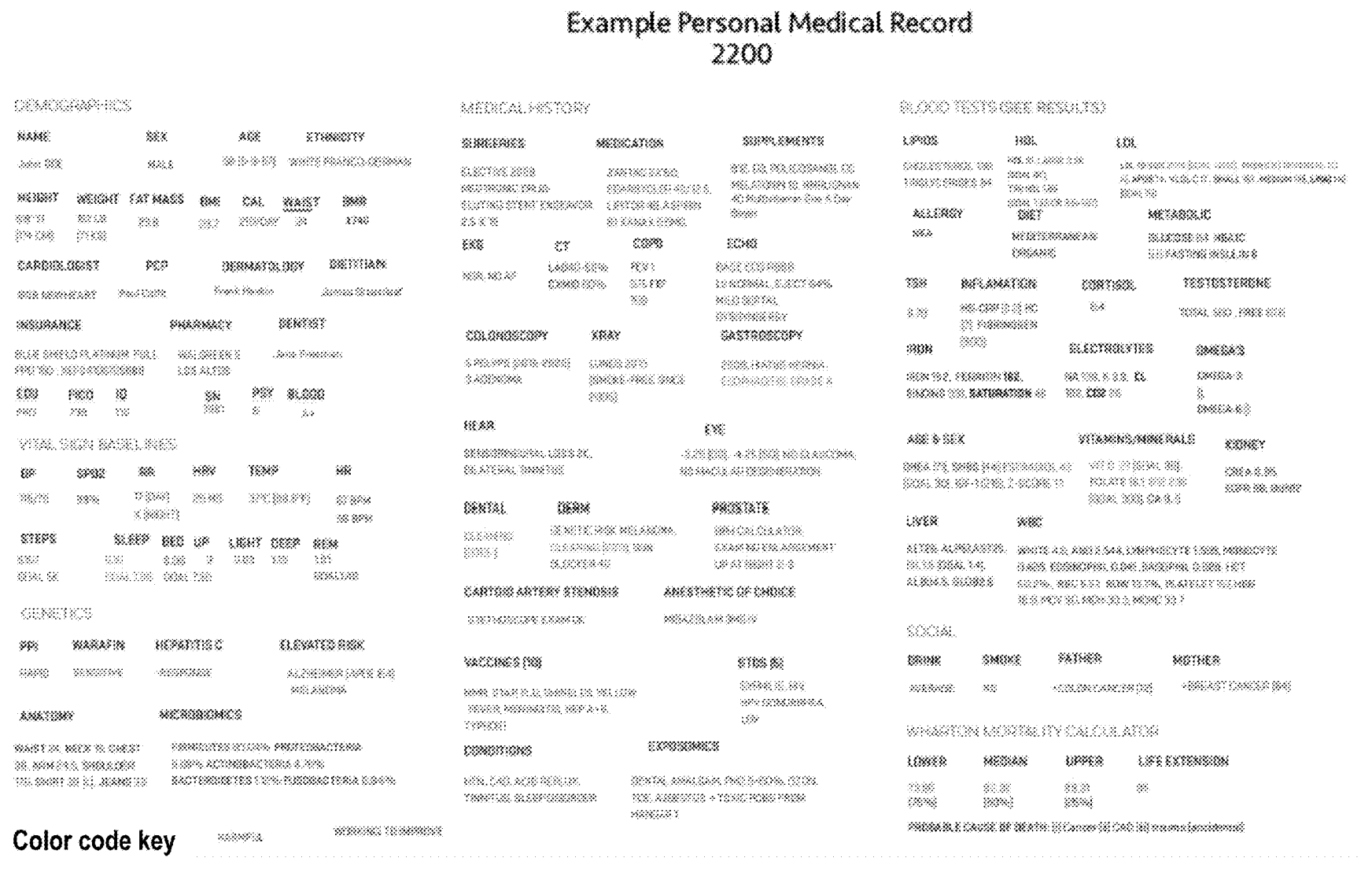

Referring now to FIG. 22B, a screenshot of an example of a single personal medical record 2200 for an individual (e.g., John Doe) is shown. Referring to both FIGS. 22A-22B, the demographics information 2202 includes, without limitation, data about the following: name, sex, age, ethnicity, height, weight, fat mass body mass Index (BMI), waistline measurement, basal metabolic rate (BMI), cardiologist, primary care physician (PCP), dermatologist, dietician, medical insurance provider, preferred pharmacy, and dentist.

The vital sign baselines information 2203 includes, without limitation, data about the following: blood pressure (BP), blood oxygen level (Sp02), Riva-Rocci's blood pressure (RR), heart rate variability (HRV), body temperature (temp), heart rate (HR), steps per distance walked, sleep data (e.g., bed sleep, up, light sleep, deep sleep, rapid eye movement (REM) sleep).

The genetics information 2204 includes, without limitation, data about the following: protein-protein interaction (PPI), Warfarin therapy, hepatitis C, heart rate variability (HRV), elevated risk (e.g., Alzheimer's disease, melanoma, etc.).

The anatomy information 2205 includes sizes of waist, neck, chest, arms, shoulders, shirt, and waste size of pants. Over time sizes can change indicating obesity or abnormal growth.

Microbiomics 2206 information include the commensal, symbiotic, and pathogenic microorganisms that are found in human bodies such as the digestive tract. Proteobacteria, actinobacteria (e.g., corynebacterineae, propionbacterineae, micrococcineae), bacteroidetes, cyanobacteria, fusobacteria, firmcutes (e.g., staphylococcaceae) are a few microbiomics.

The human microbiome may have a role in auto-immune diseases like diabetes, rheumatoid arthritis, muscular dystrophy, multiple sclerosis, fibromyalgia, and perhaps some cancers. A poor mix of microbes in the digestive tract can aggravate obesity. Some microbes may be associated with the production of neurotransmitters known to occur in the brain.

The medical history information 2207 includes, without limitation, data about the following: surgeries, medications (e.g., prescription drugs and non-prescription drugs), supplements (e.g., vitamins), electrocardiogram (EKG), computed tomography (CT) scan, chronic obstructive pulmonary disease (COPD), echocardiogram (echo), colonoscopy, X-ray, gastroscopy, hearing, eyesight, dental, dermatology, prostate, carotid artery stenosis, anesthetic of choice, vaccines, sexual transmitted diseases (STDs), conditions, and exposomics.

The diagnostic test results information (e.g., blood test results and urine test results) 2208 includes, without limitation data about the following: lipids, high-density lipoprotein (HDL) cholesterol, low-density lipoprotein (LDL) cholesterol, allergy, diet, metabolic, thyroid stimulating hormone (TSH), inflammation, cortisol, testosterone, iron, electrolytes, omegas, age and sex, vitamins/minerals, kidney, liver, and white blood cell (WBC) count.

The social information 2209 includes, without limitation, data about the following: drinking, smoking, fathers health, and mothers health.

The life expectancy/mortality calculated information 2210 (e.g., Wharton Mortality Calculator) includes, without limitation, data about the following: lower life expectancy, median life expectancy, upper life expectancy, life extension, and probable cause of death. The life expectancy/mortality calculated information 2210 can serve as a summary of the aggregation of the medical information. That is, the life expectancy/mortality calculated information 2210 is responsive to the medical information of the user in the PMRi. For example, more frequent doctor visits and tests, such as blood tests for diabetes, cholesterol, etc. can increase the measure of a the user's life expectancy 2210. As another example, at age 50 having a colonoscopy every 2-3 years can increase the measure of life expectancy 2210 over having never having one or less frequently (e.g., only having a colonoscopy every 5 years) to check for colon cancer and remove polyps. Including the life expectancy/mortality calculated information 2210 amongst the medical information illustrates the relationship between each so that a user may take more charge of his/her health care to improve life expectancy. Diet and frequency of alcohol intake may also be considered in the personal medical record and life expectancy/mortality calculation. Even teeth cleaning may effect ones life expectancy/mortality calculated information 2210.

The personal medical record PMRi 2200 may include certain goals with dates of taking tests or performing health related tasks and compliance—whether a user completed the tests or tasks or not by the date indicated or not. For example, data field 2270 in the personal medical record 2200 shown in FIG. 22C has a plan or a goal 2271 that is desirable to meet. If no goals are set, statistical numbers (e.g., normal number/range of a population for a given age) may be used as a comparable from which a comparison for compliance of the users data values may be made. A compliance bar or a numerical compliance score 2272 may be displayed near the data field 2270 in order to indicate how successful the goal/normal number is presently being met. For example, a goal of 7.00 hours of sleep may be set and only 5.16 hours were achieved. In which case, a compliance bar may be smaller than a length of 100%. Color coding may also be used to indicate a measure of the level of compliance (e.g., green for substantial compliance, yellow for medium compliance, and red for low compliance). For example, the numeric value 5.16 hours may be in red for a low compliance with a sleep goal or the normal number hours of sleep.

To lower and defray costs to users, the personal medical record PMRi 2200 that is displayed on the display device may include a portion dedicated to health or medical related advertisements 2218. For example, the advertisements 2218 may be for those devices and services that may be used with the personal medical record PMRi 2200 to automatically populate data into the data fields. The health or medical related advertisements 2218 may be context based if a user has a certain condition to which certain drugs or medical devices may be helpful. In other cases, health or medical related advertisements 2218 may pop up and have the user click through to view his personal medical record PMRi.

Figure 22C:
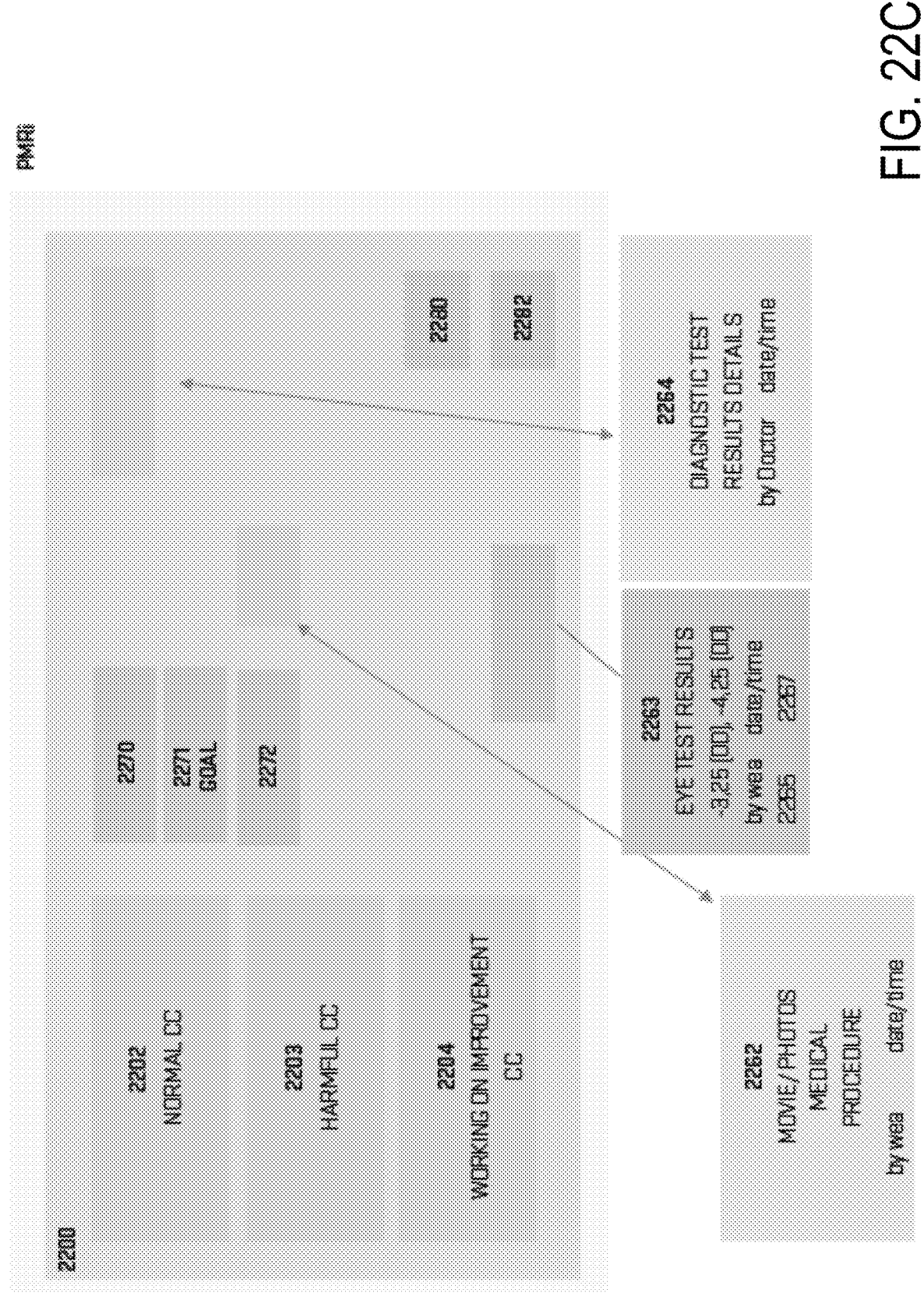
FIG. 22C illustrates links and color-coding that may be used with a personal medical record.

Referring now to FIG. 22C, each personal medical record PMRi 2200 for each captured time/date can include color coding (CC) or highlighting to emphasize specific information in the personal medical record. The personal medical record 2200 may have a color coding key near an edge of the record. A normal color coding (CC) indicating normal medical information may be indicated in the PRMi with black letters/numbers on a white background (or white letters/numbers on a black background) on the display device for example. A harmful color coding (CC) indicating abnormal medical information may be indicated in the PRMi with red letters/numbers on a white background (or black back ground). For example, the user John Doe may only be getting 5.16 hours of sleep that are highlighted in red, short of a goal of 7 hours of sleep. A "working on improvement" color coding (CC) indicating medical information that has a set goal for improvement may be indicated in the PRMi with yellow letters/numbers on a white background (or black background). For example, a goal of exercise by climbing 5000 steps of a stairmaster may be set and indicated in yellow with 5157 being achieved.

Furthermore, each personal medical record PMRi 2200 for each captured time/date may include links to detailed backup information from which information was extracted. A media link 2262 may be used to link media to one or more of the personal medical records from a given date/time and stored in the medical record data base. The media link 2262 may be photographs or a movie of a medical procedure. For example, photographs or a movie captured during a colonoscopy may be linked to a personal medical record. A results link 2264 may be linked to one or more of the personal medical records from a given date/time and stored in the medical record data base. The results link 2264 may be detailed lab results from a doctor or a medical lab that includes medical data that was extracted into the personal medical record. For example, a pathology report of the biopsy of tissue samples taken during a colonoscopy may be the lab results linked to a personal medical record.

A user may choose to share his personal medical record (PMRi) 2200 with his doctors (primary care physician), medical service providers, love ones (e.g., husband, wife, family members), close friends, and/or guardian/care taker. Each may be allowed to read data only access, or both read and write data access into all or part of a patient's medical records. For example, an eye doctor may only be only granted access to write information into the personal medical record with regards to the patient's eyes and not genetics, for example. Accordingly, file protections may be set for the users personal medical records based on login identification of doctors, medical service providers, family members, close friends, and/or guardian/care taker associated with the user. If they are not associated with the user, no access is granted to the user personal medical records.

Moreover, with file sharing, a doctor or patient may update portions of the personal medical records. Information into one or more various data fields 2263 in the personal medical record 2200 may be stored by patient, doctor, loved one, or other care giver. The data fields 2263 can indicate the author 2265 of the information and the date/time 2267 when it was stored into the personal medical record 2200. The media links 2262 and results links 2264 may similarly indicate author and the date/time when they were associated with the personal medical record 2200.

The user may elect to even anonymously share information within his personal medical record with others within a group. For example, a user with diabetes may elect to share his conditions with a group of other uses to show trends and averages of diabetes patients. As another example, a user may elect to share blood pressure information to show trends of those in a similar age group.

The personal medical record PMRi 2200 may include a photograph 2280 of the user, such as a self taken photograph captured with a smart phone. The photograph 2280 may be initially taken upon start up and used to automatically guess at a number of user parameters using facial recognition of the user's face in the photograph. For example, the length of a user's face can be used with his height and a face/height ratio to automatically guess and populate a weight data field in the personal medical record PMRi 2200. As another example, sex (gender) and age may be automatically guessed and populated using facial recognition of the users face in the photograph 2280.

In another embodiment, the personal medical record PMRi 2200 may include all or a part (snippets) of genome sequence 2282 of the Deoxyribonucleic acid (DNA) of the user. All or portions of the genome sequence may be analyzed for heredity health trends of the user. Saving family genome sequences can assist in diagnosing heredity health trends in children of a pair of user.

Figure 27:
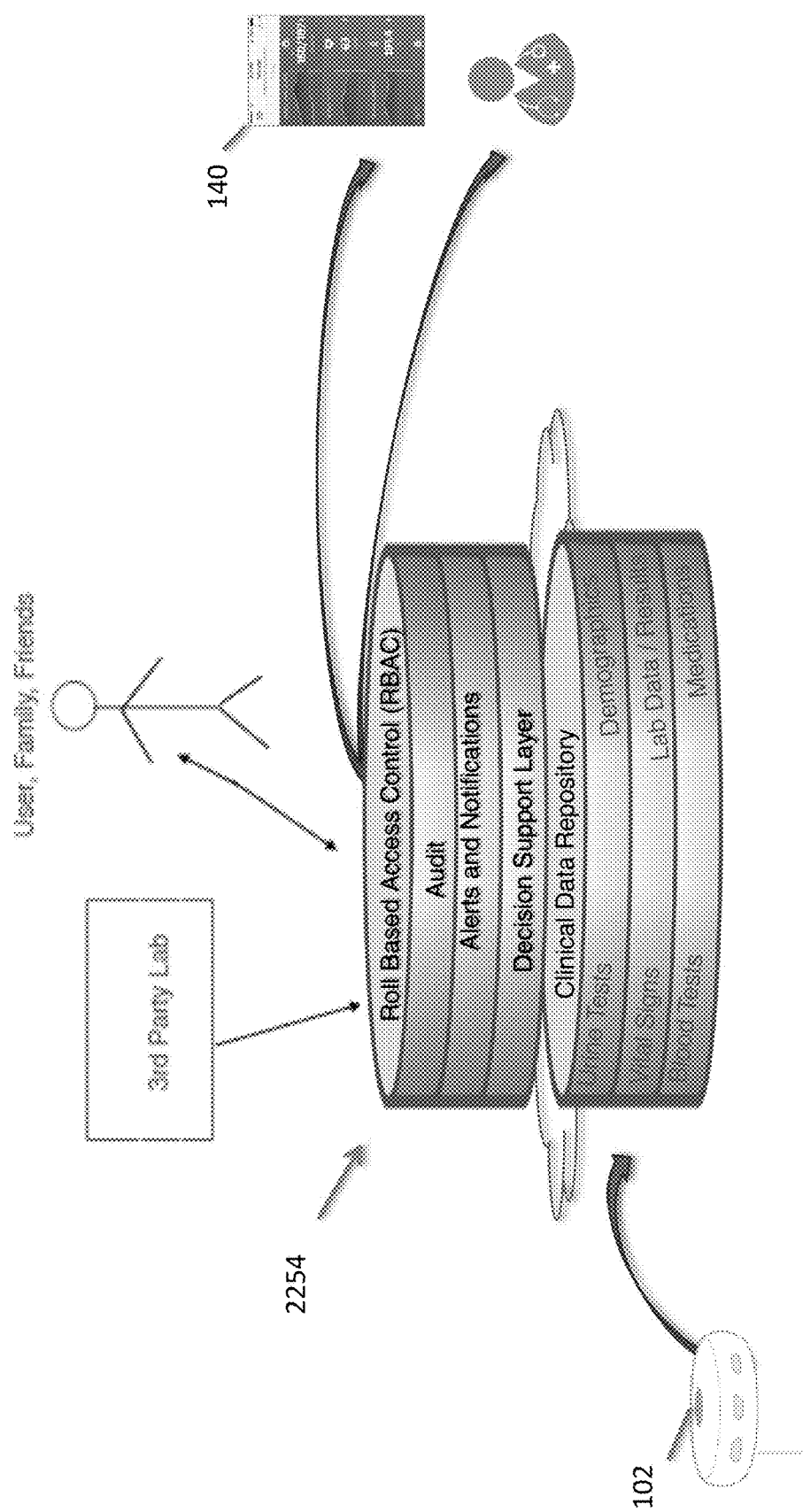
FIG. 27 illustrates a block diagram of the personal medical record database stored on a network storage device.

Referring now to FIG. 27, a block diagram of a personal medical record data base 2254 is shown. The personal medical record data base 2254 is available over the internet as it is stored on a network storage device, such as storage server. The personal medical record data base 2254 includes a clinical data repository to store the data and information associated with the personal medical records of users. The personal medical record data base 2254 includes a role based access control mechanism to control access to the clinical data repository to authorized users, authorized family, authorized laboratories, authorized hospitals, authorized pharmacies, and authorized physicians or other authorized caregivers. The role based access control mechanism includes an audit mechanism, an alert and notification mechanism, and a decision support mechanism.

The clinical data repository of the personal medical record data base 2254 includes urine tests, blood tests, vital signs, other lab data and test results, medications, demographics, and other information for the personal medical record. A vital signs scanner 102, discussed herein, is used to scan a users vital signs and have them automatically stored in the clinical data repository of the data base 2254. A blood test kit may be used to obtain the blood test results and have them automatically stored in the clinical data repository. A urine test kit may be used to obtain urine test results and have them automatically stored in the clinical data repository.

The results from the vital signs scanner, urine test kit, and blood test kit automatically stored in the clinical data repository are also automatically populated into a user's personal medical record. Results from authorized third party laboratories can be stored in the clinical data repository and may also be automatically populated into a user's personal medical record. Prescriptions that are written by an authorized doctor and filled by an authorized pharmacist may be stored in the clinical data repository and automatically populated into a user's personal medical record. Check in and records of procedures during a visit to an authorized hospital or medical clinic may be stored in the clinical data repository and automatically populated into a user's personal medical record. The system is advantageously transparent in that it eases the burden of data entry of the information into the data fields of the user's personal medical record.

Users can gain access to their personal medical records through a computer system or a portable electronic device, such as the screen 140 of a multifunction device 104, a smartphone or tablet computer. Physicians or other health service providers, that are authorized by a user, can also gain access to a users personal medical records. If multiple doctors are providing care for the user, they may know from viewing the prescriptions previously given by another doctor to avoid adverse drug interactions from a new drug prescription. From the personal medical record, another doctor may see what other type of care was ineffective with the user/patient and try a different type of treatment. Accordingly, the personal medical record can advantageously provide a means of interaction between doctors, pharmacists and other care givers treating the same user/patient.

Figure 26:
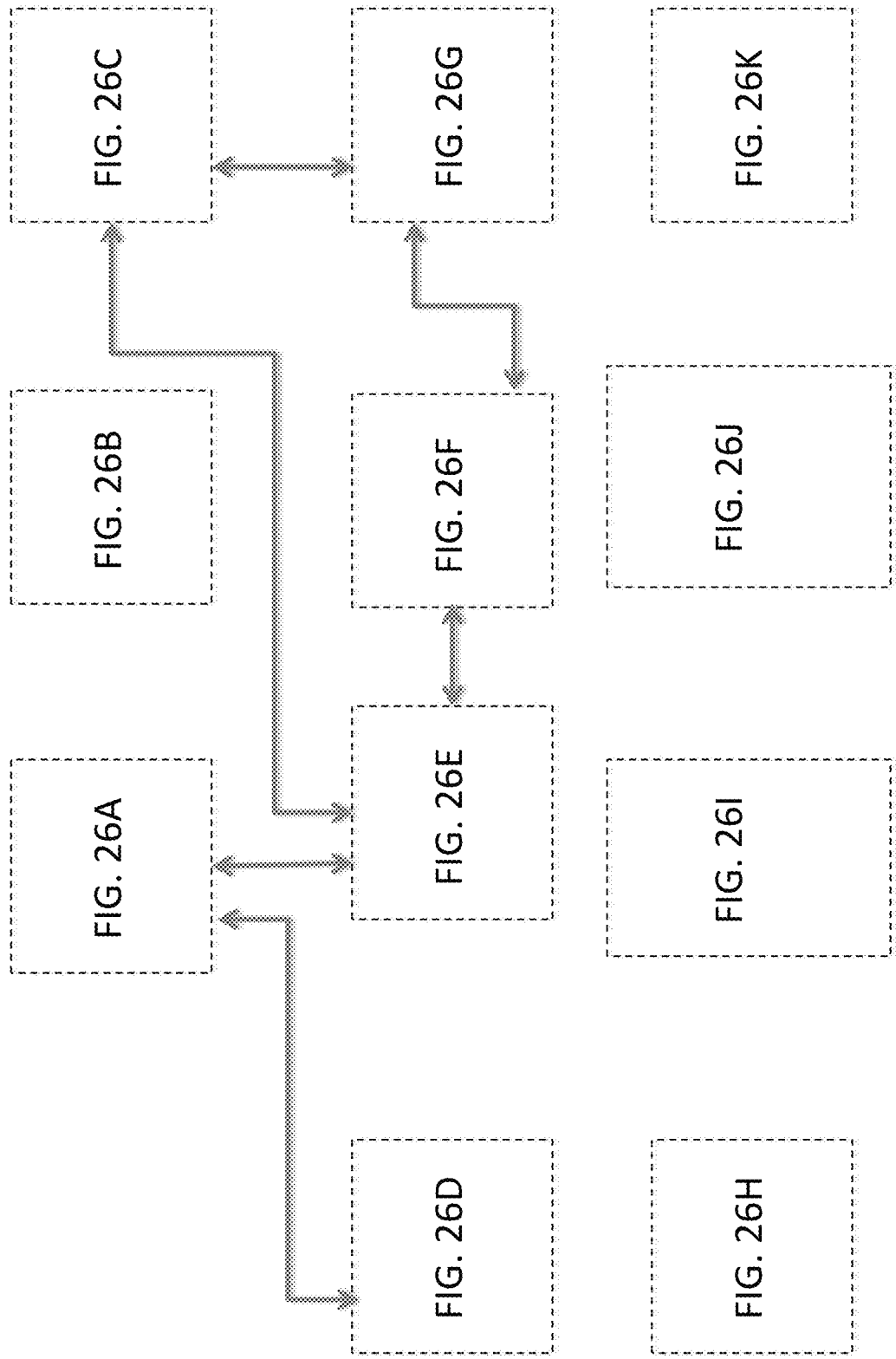
FIGS. 26 and 26A-26K illustrate interrelationships of one or more query screens to capture information and software application objects for generating and displaying a personal medical record.

FIG. 26 illustrates a map of the interrelationship of FIGS. 26A-26K of detailed software application processes for generating and displaying personal medical records. The personal medical record software application may be adaptable to the type of electronic device and display that is to receive inputs and display a personal medical record. For example, the electronic device may be a smart phone with a processor and a 4 to 6 inch diagonal touch screen display. As another example, the electronic device may be a smart tablet with a processor and a 10 to 13 inch diagonal touch screen display. As another example, the electronic device may be a laptop computer with a processor and an 11 to 17 inch diagonal display screen, or a desktop computer with a processor and a 15 to 36 inch or greater diagonal display screen. The personal medical record software application has the capability of adapting to various size display screens. With different size display screens, the personal medical record software application may display one or a plurality of windows to query a user for medical record information and to display medical record information of a personal medical record. The personal medical record software application may be client software executed by an electronic device or a combination of client-server software with client software executed by an electronic device and server software executed by a server.

Figure 26A:
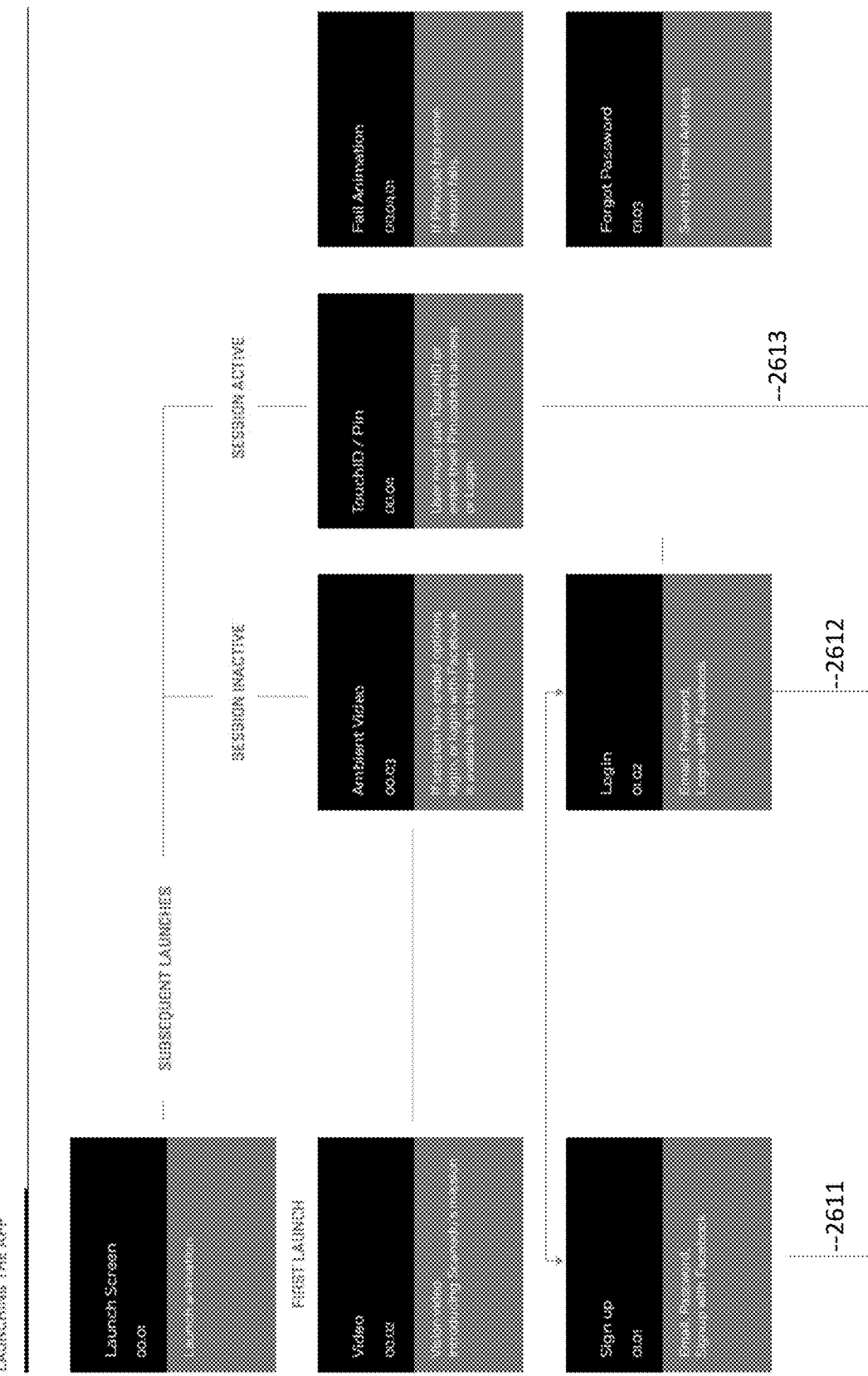

FIG. 26A illustrates processes for launching the personal medical record software application. The launching processes include processes with interconnections 2611, 2612, and 2613 to other processes of the personal medical record software application.

Figure 26B:
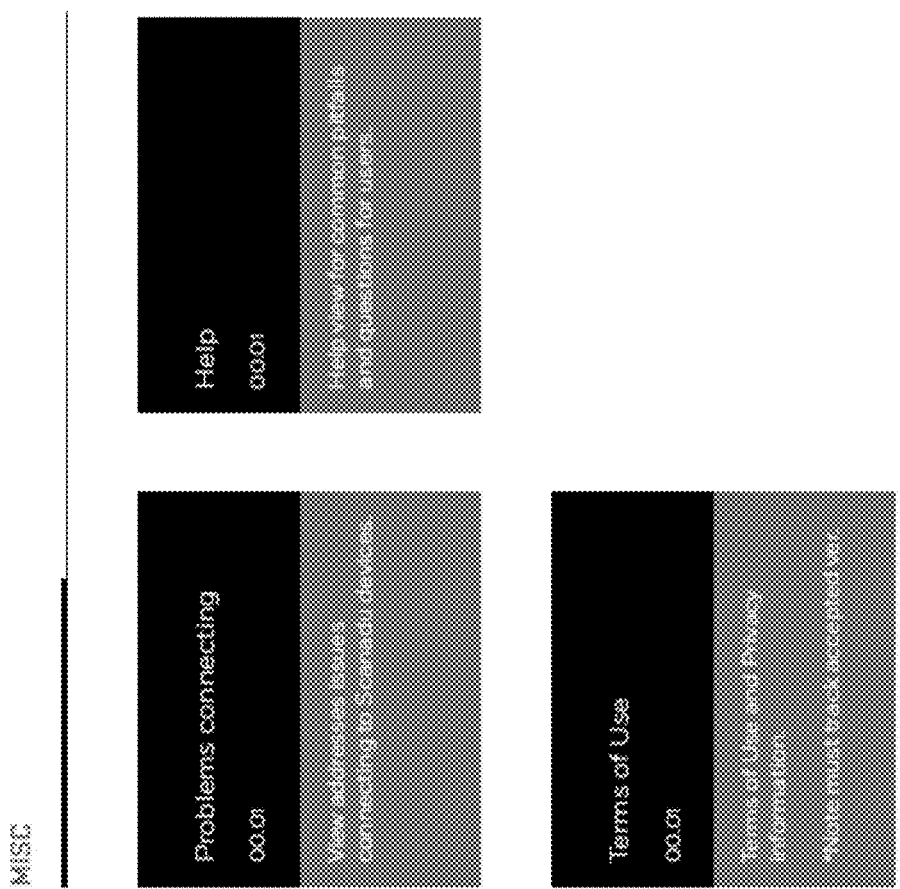

FIG. 26B illustrates miscellaneous processes for support of the personal medical record software application including a help screen, a trouble shooting screen, and a terms of use/privacy screen.

Figure 26C:
Figure 26C:
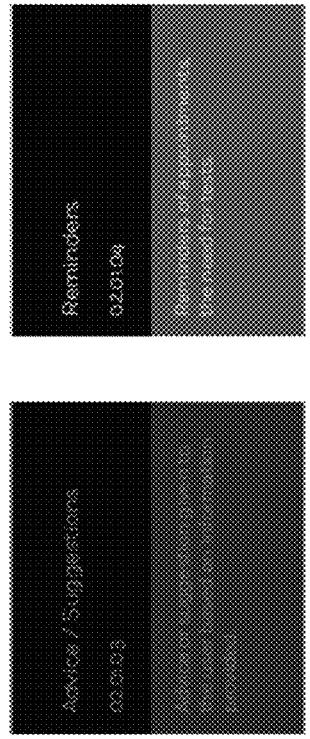
Figure 26C:
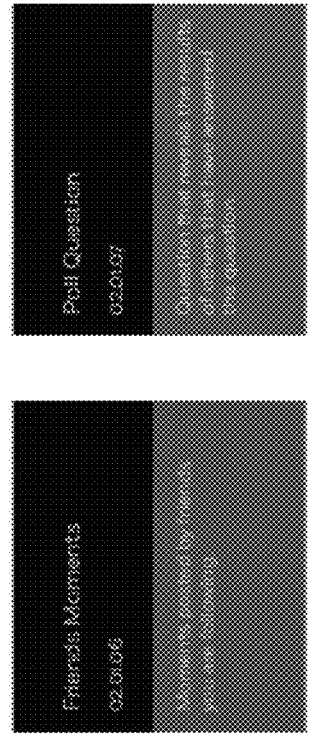

FIG. 26C illustrates home feed processes including passive profiling questions to populate detail of a users profile; reminders of doctor appointments and the need to have tests performed periodically; and messages from friends, doctors, or others that a user shares their profile and medical moments. The profiling question process includes an interconnection 2642 to other processes of the personal medical record software application.

Figure 26D:
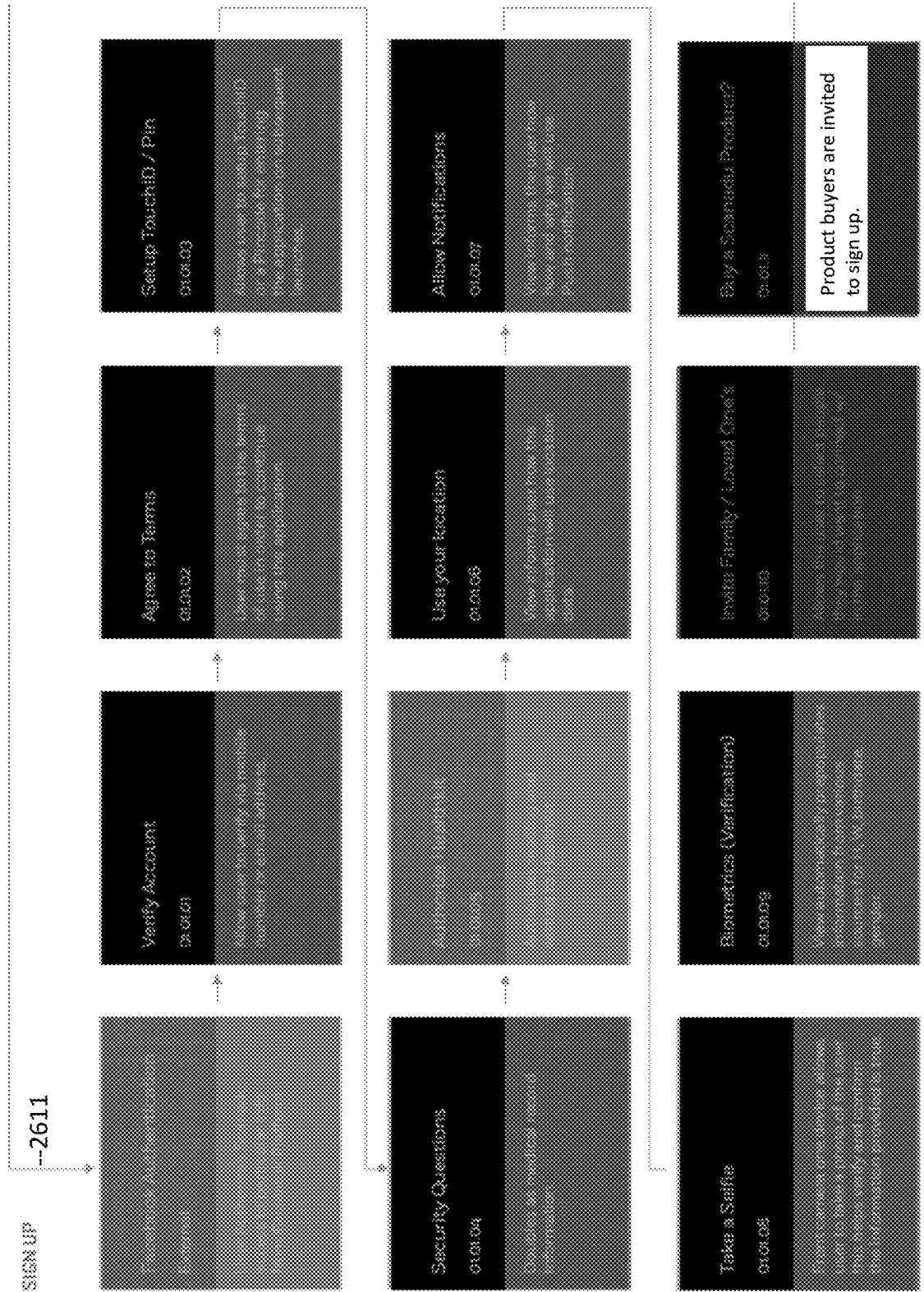

FIG. 26D illustrates processes of signing up a user and the personal medical record software application to a server and capture general information such as a user photo, and biometric information for verification purposes. A method of authentication by social media includes an interconnection 2611 to one or more of the launching processes (e.g., sign up process) of FIG. 26A.

Figure 26E:
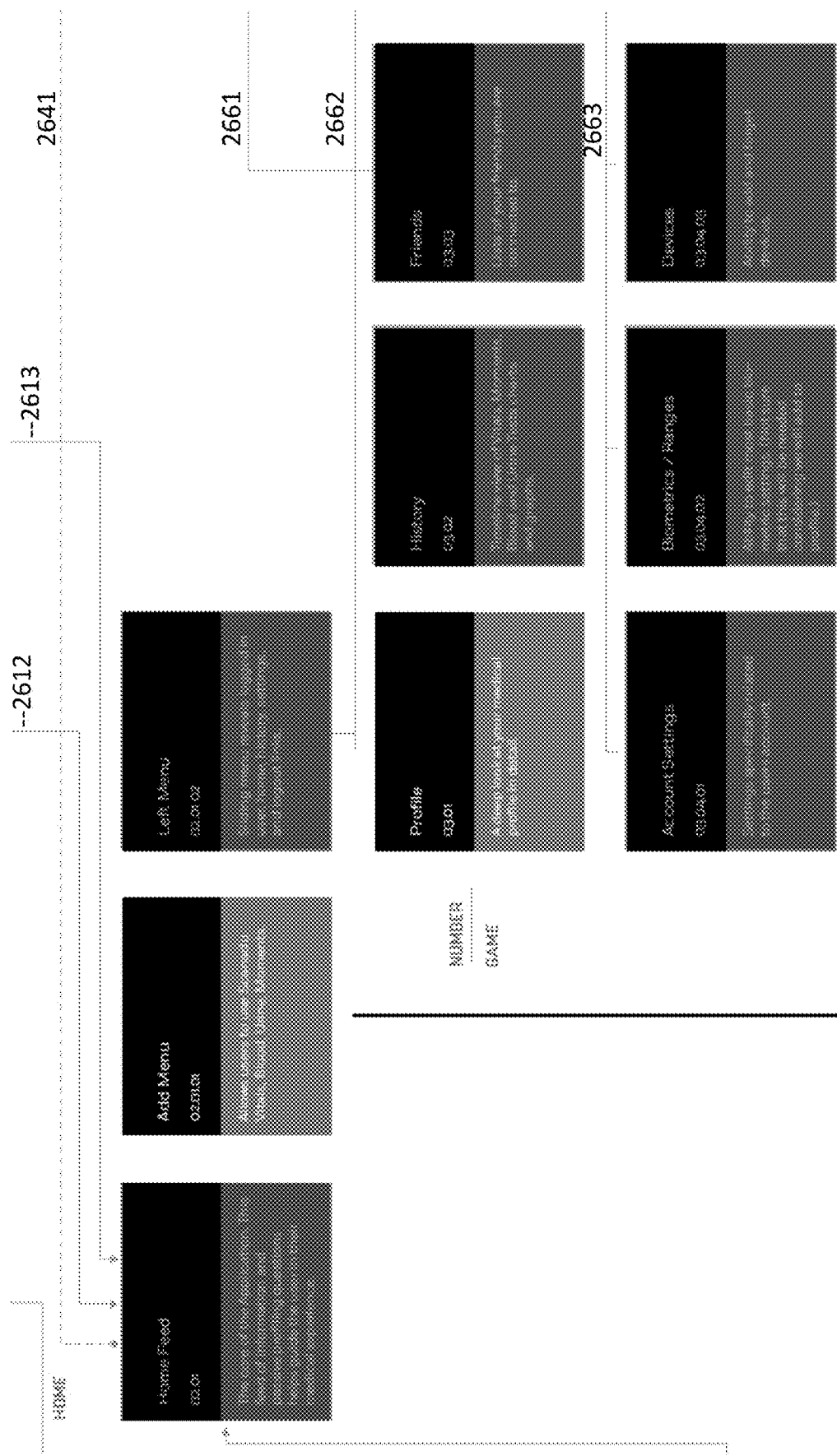
Figure 26F:
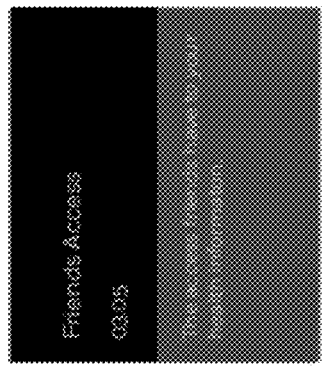
Figure 26F:
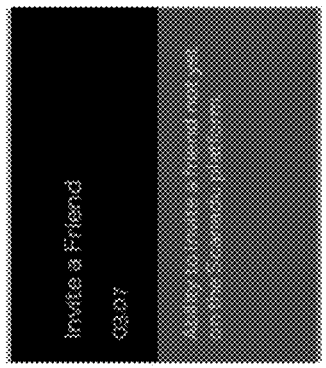
Figure 26F:
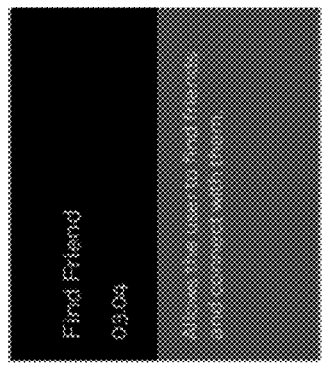
Figure 26F:
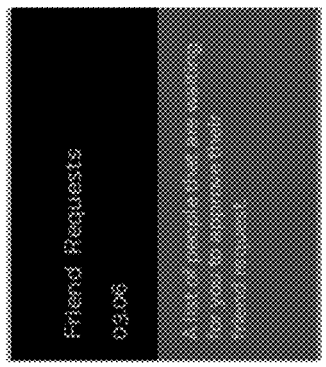
Figure 26F:
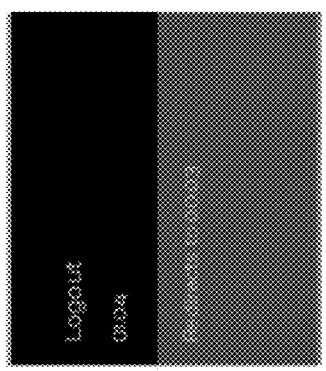
Figure 26F:
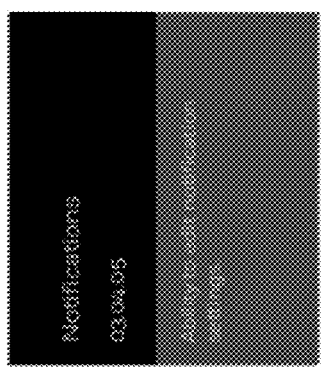
Figure 26F:
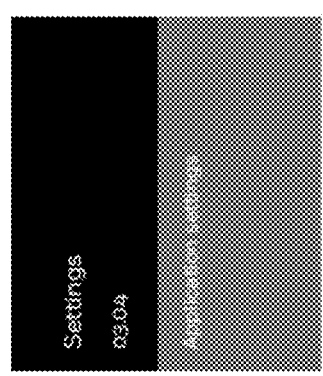
Figure 26F:

FIGS. 26E-26F illustrate core processes of the personal medical record software application that queries users, feeds information into the personal medical record of a given date and time, and creates a network of contacts around the personal medical record.

The core processes include interconnections 2612, and 2613 to the launching processes shown in FIG. 26A of the personal medical record software application. The core processes further include interconnection 2641 to the home feed processes shown in FIG. 26C of the personal medical record software application. Core processes of FIG. 26E have interconnections 2661,2662,2663 to the core processes shown in FIG. 26F.

Figure 26G:

FIG. 26G illustrates profile details that the personal medical record software application queries and gather together to form and display a personal medical record. The profile details generally includes biometrics/demographics 2202, genetics 2204 and microbiomics 2206, medical history 2207, social 2209, medical or health service providers 2212, and medical moments 2215. Further details of information displayed is provided below each category.

Biometrics information 2202 may include weight, blood type, height, birth date body mass index (BMI), anatomy, sex, and vital signs (blood pressure, oxygenation, respiration rate, temperature, hear rate, heart rate variability).

Genetics 2204 information may include genes (DNA and chromosomes), heredity, and genetic variation. Family medical conditions/diseases may be inherited such as heart disease, gastroesophageal reflux disease, cancer (melanoma), and Alzheimer for example. Drugs taken for inherited diseases may be included with genetics 2204 information.

Microbiomics 2206 information may include the commensal, symbiotic, and pathogenic microorganisms that are found in human bodies such as the digestive tract. Proteobacteria, actinobacteria (e.g., corynebacterineae, propionbacterineae, micrococcineae), bacteroidetes, cyanobacteria, fusobacteria, firmcutes (e.g., staphylococcaceae) are a few microbiomics.

Medical or health service providers 2212 may include names doctors (e.g., primary care doctor, ophthalmologist, obstetrician/gynecologist; cardiologist, urologist, dermatologist, gastroenterologist, endocrinologist), pharmacists, dentist, psychiatrist, dietitian, and insurance provider.

The medical history information 2207 may include hospitalizations, family history, chronic conditions, immunizations, surgical, growth development, obstetric (family), assistive devices, female reproductive health, eyesight, medications, hearing, allergies, advanced directives, genetics, and mental health. The social information 2209 may include sleep, friends, activities, smoking, sports, recreational drugs, friends, mind/body health, sexual activity, stress, commute to work, life/work balance, alcohol, and nutrition.

The profile detail processes includes an interconnection 2642 to the home feed processes shown in FIG. 26C and an interconnection 2671 to core processes shown in FIGS. 26E-26F of the personal medical record software application.

Figure 26H:
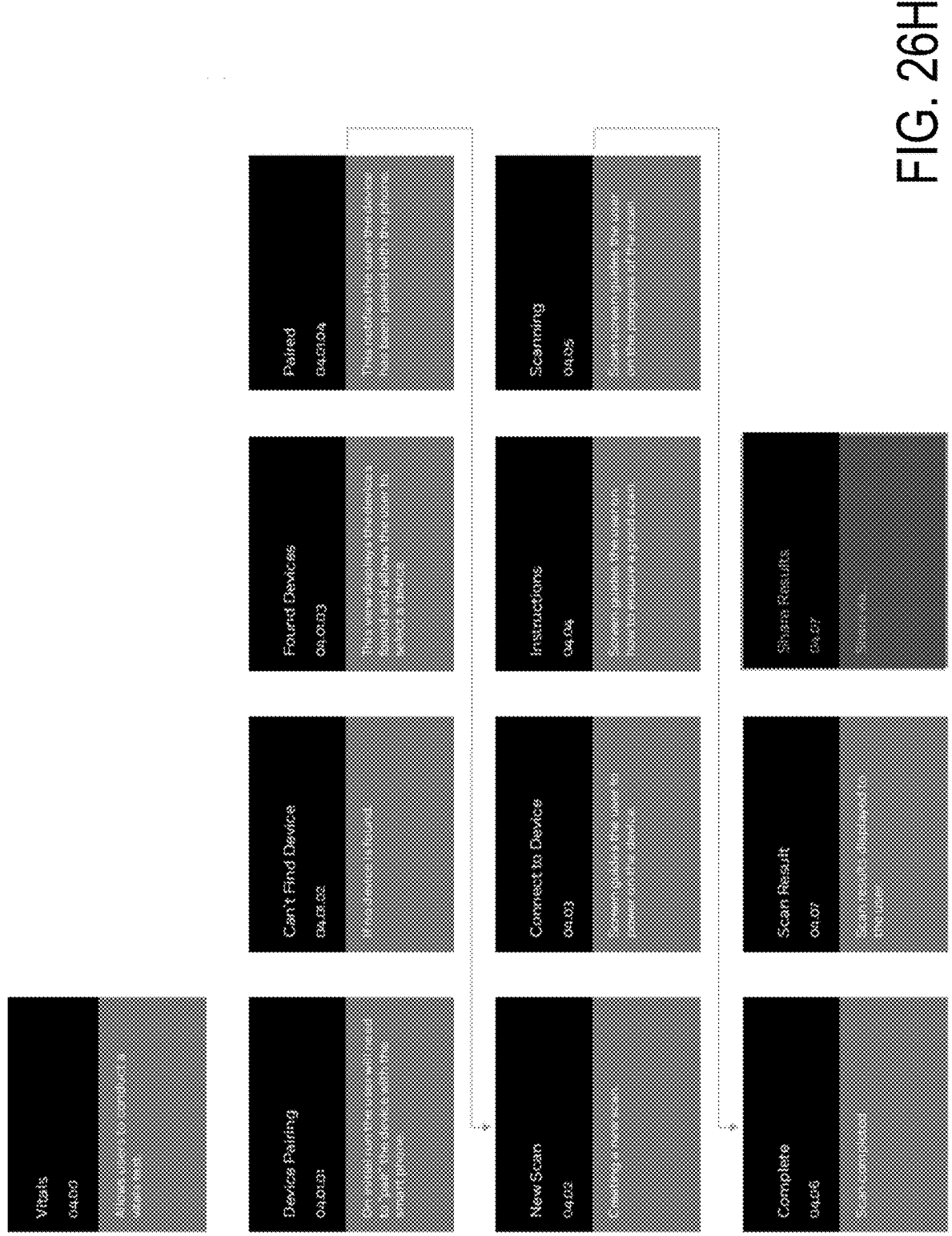
Figure 31:
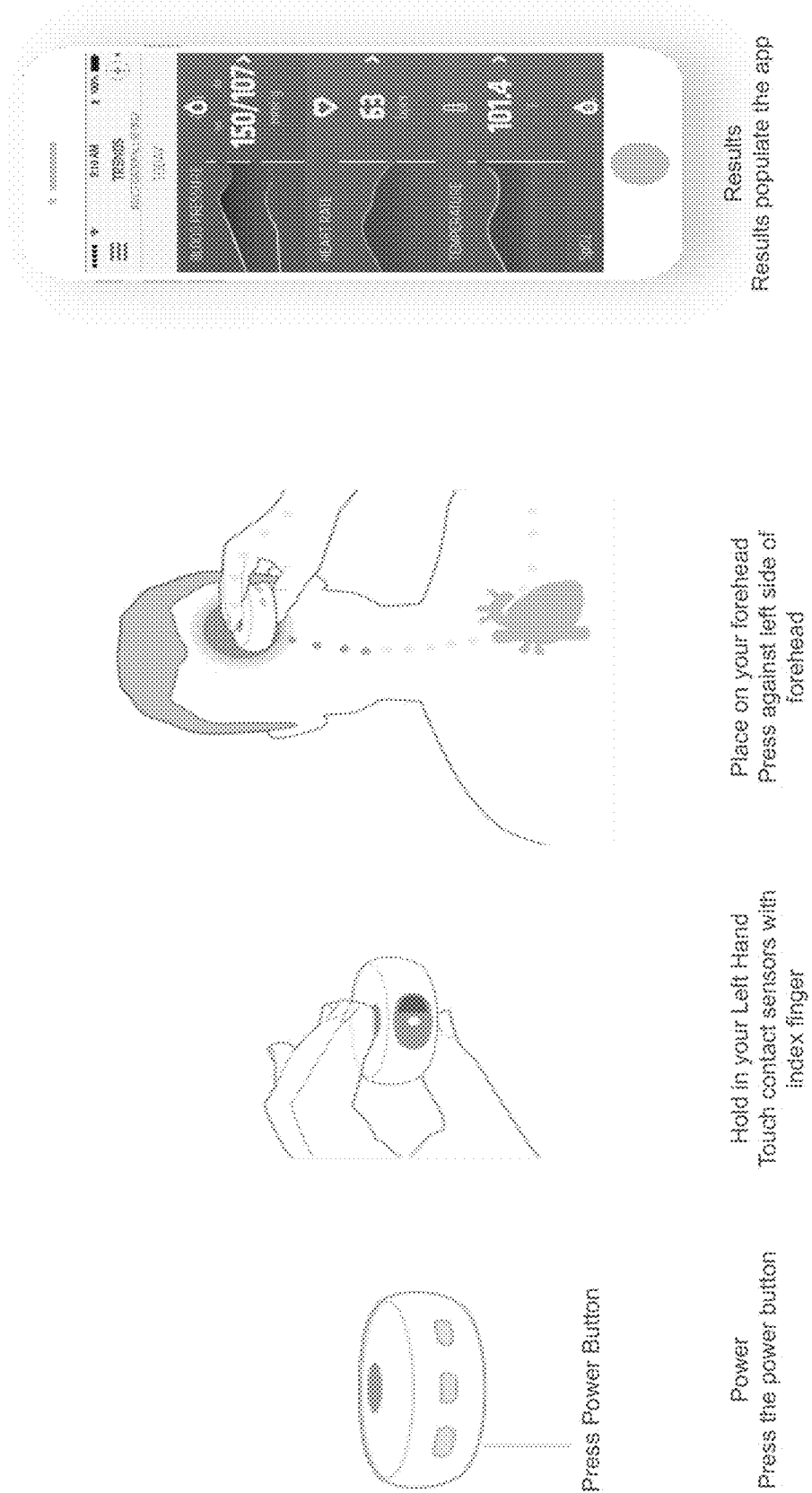
FIGS. 31-32 are diagrams illustrating use of a vital signs scanner and an application executed by a portable wireless multifunctional device to capture a plurality of vital signs of a user over a time history to be annotated into the personal medical records database to track the variation of vital signs (vital signs analysis history) as a user ages.
Figure 32:
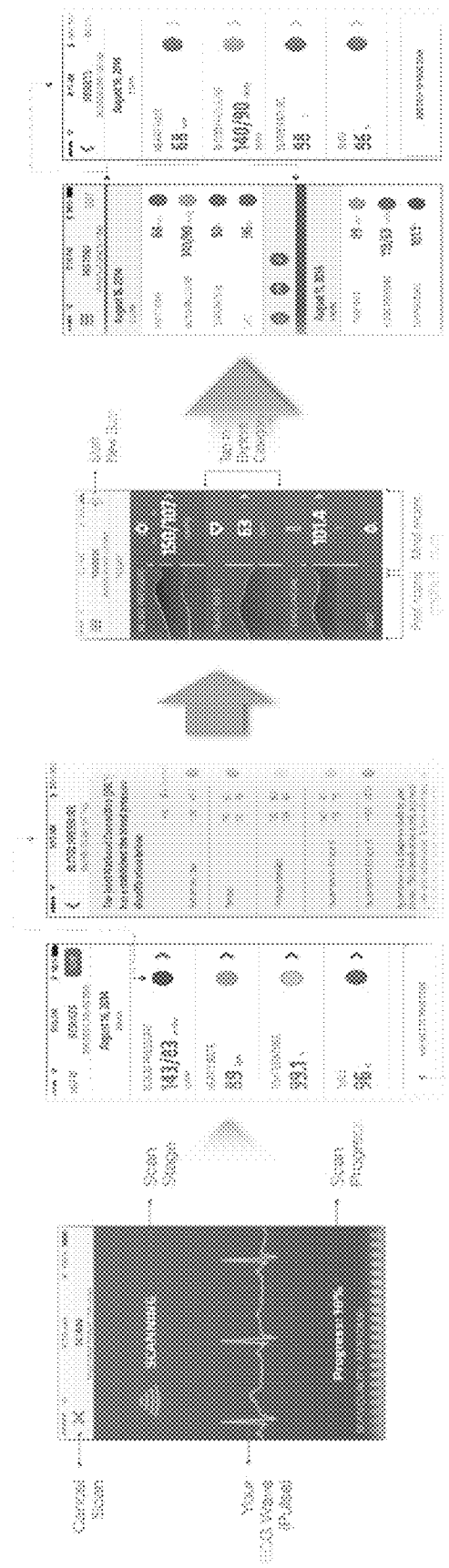
Figure 33:
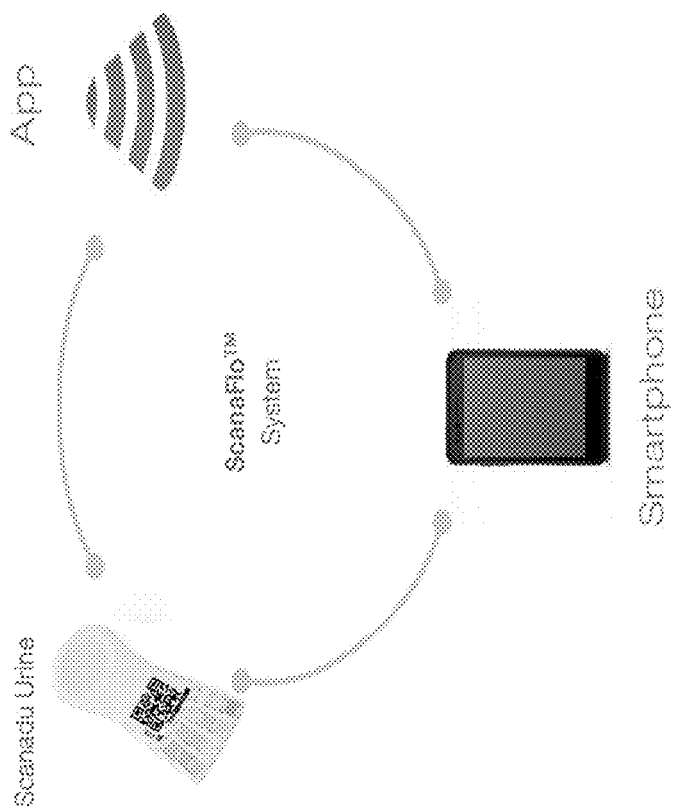
FIGS. 33-37 are diagrams illustrating use of a urine test device to test urine of the user and an application executed by a portable wireless multifunctional device to acquire one or more images of the urine test device and analyze the urine test device to determine urinalysis results that are annotated into the personal medical records database to track the variation of urinalysis (urinalysis history) as a user ages.
Figure 34:
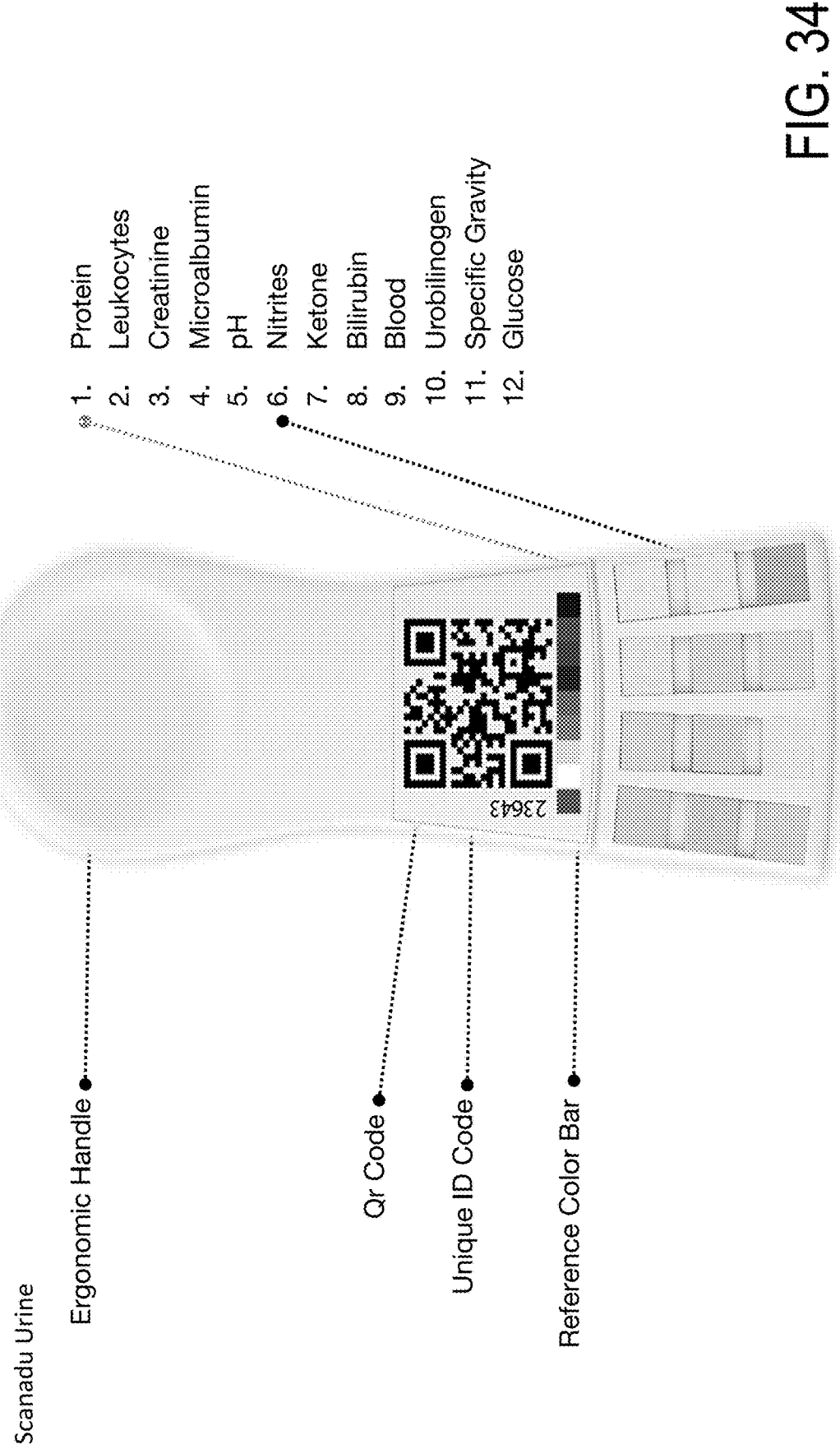
Figure 35:
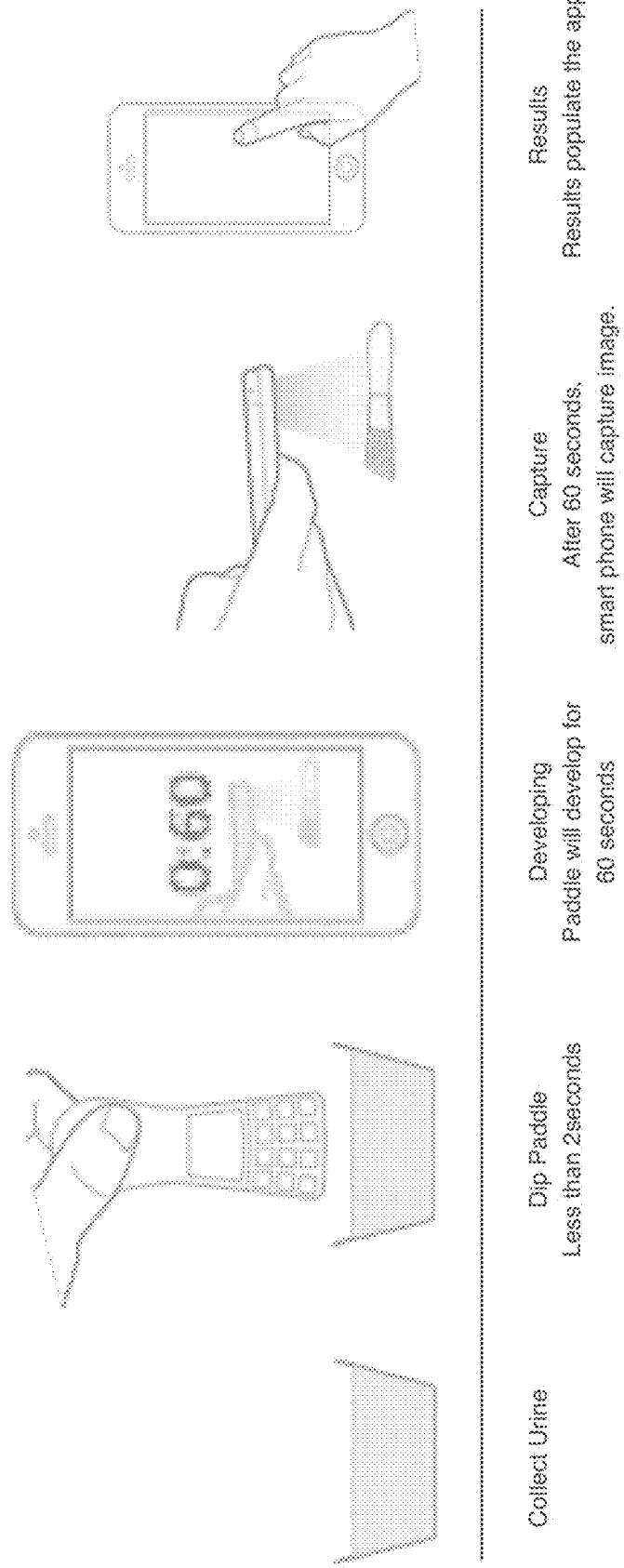
Figure 36:
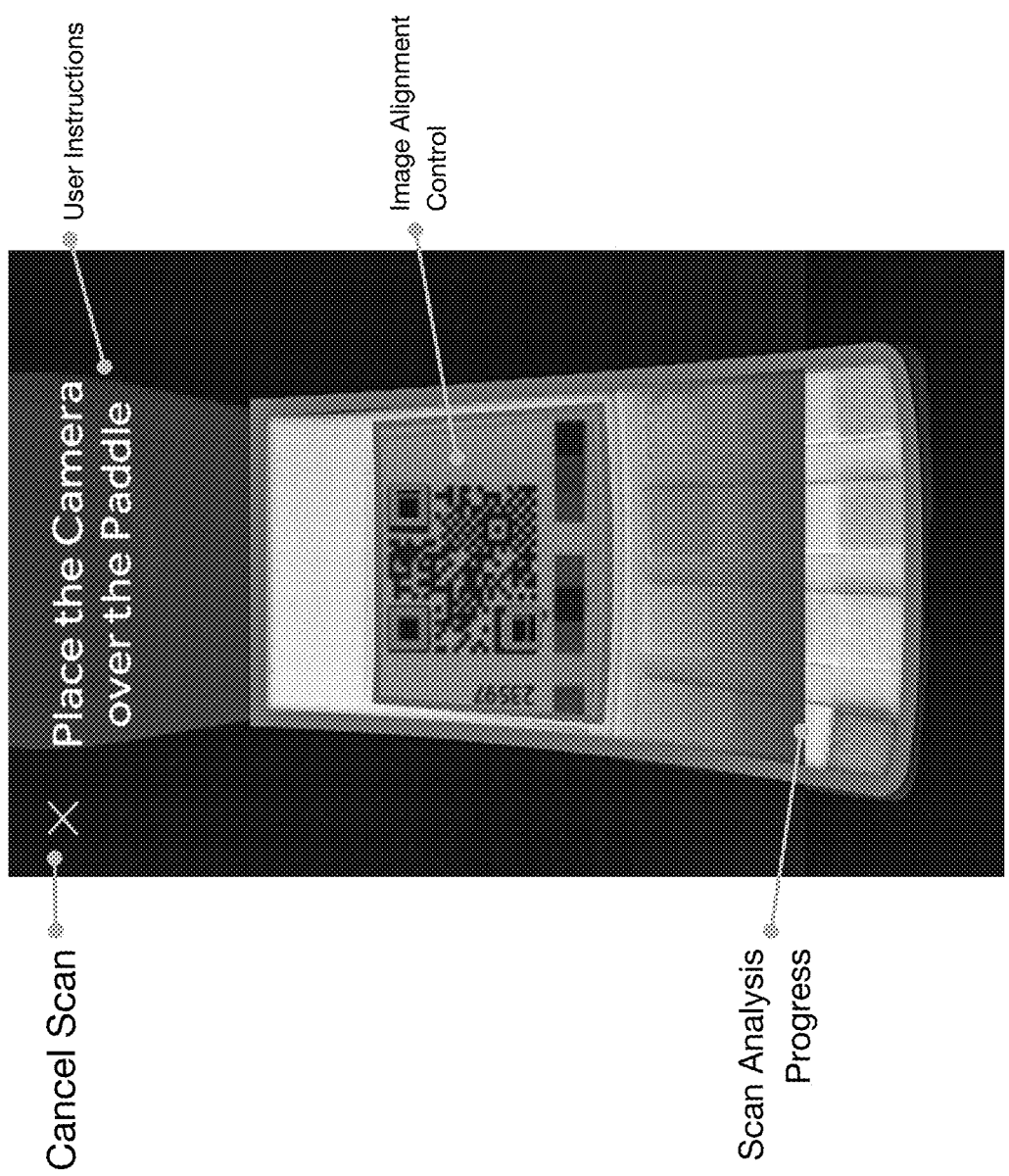
Figure 37:

FIG. 26H illustrates vital sign processes that a user performs with the personal medical record software application performs and a vital sign scanner described herein to add vita signs to a personal medical record. FIGS. 31-32 illustrate how the vital signs scanner is used to obtain vital signs information for the personal medical record database and software application.

Figure 26I:
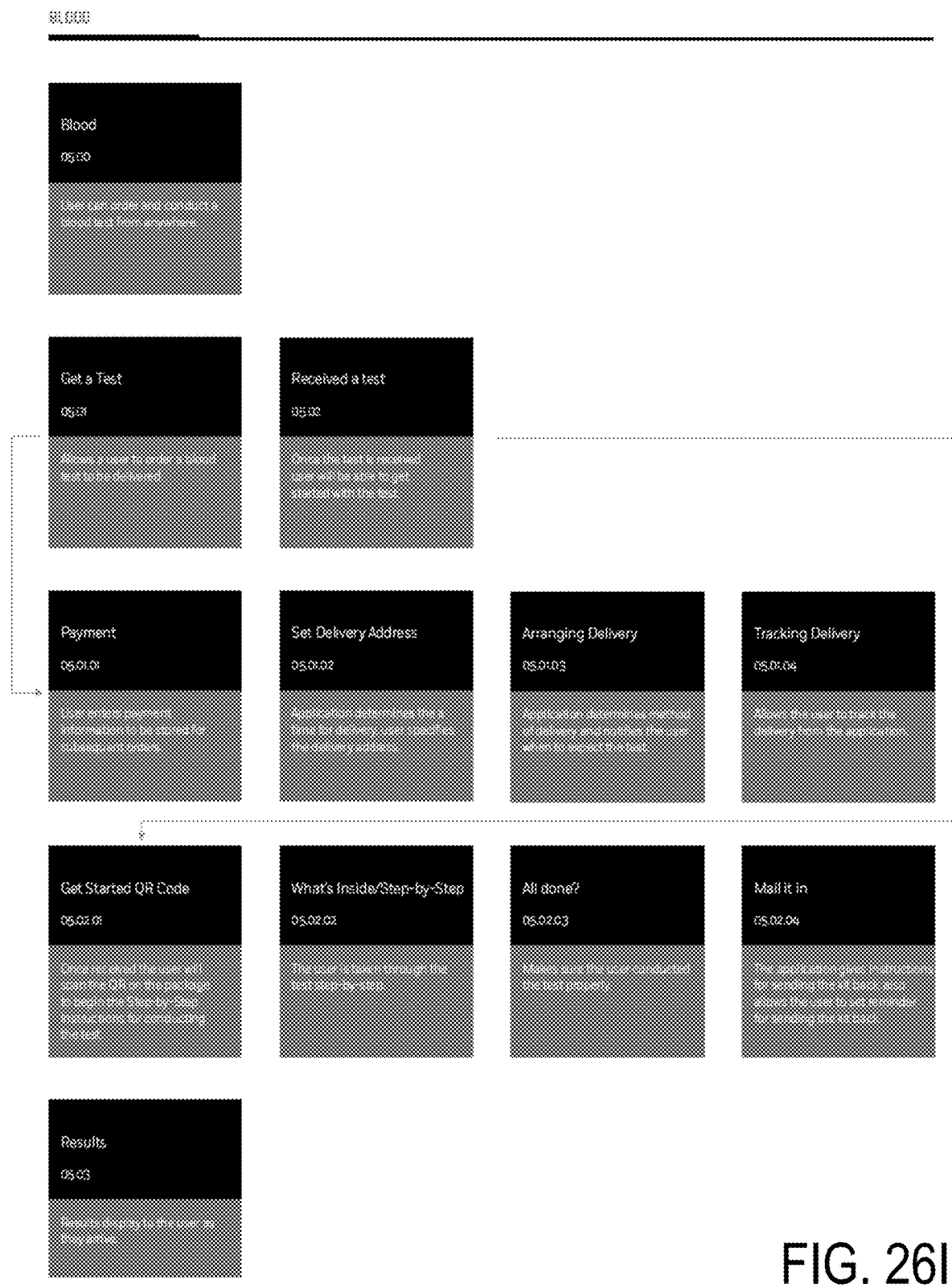
Figure 38:
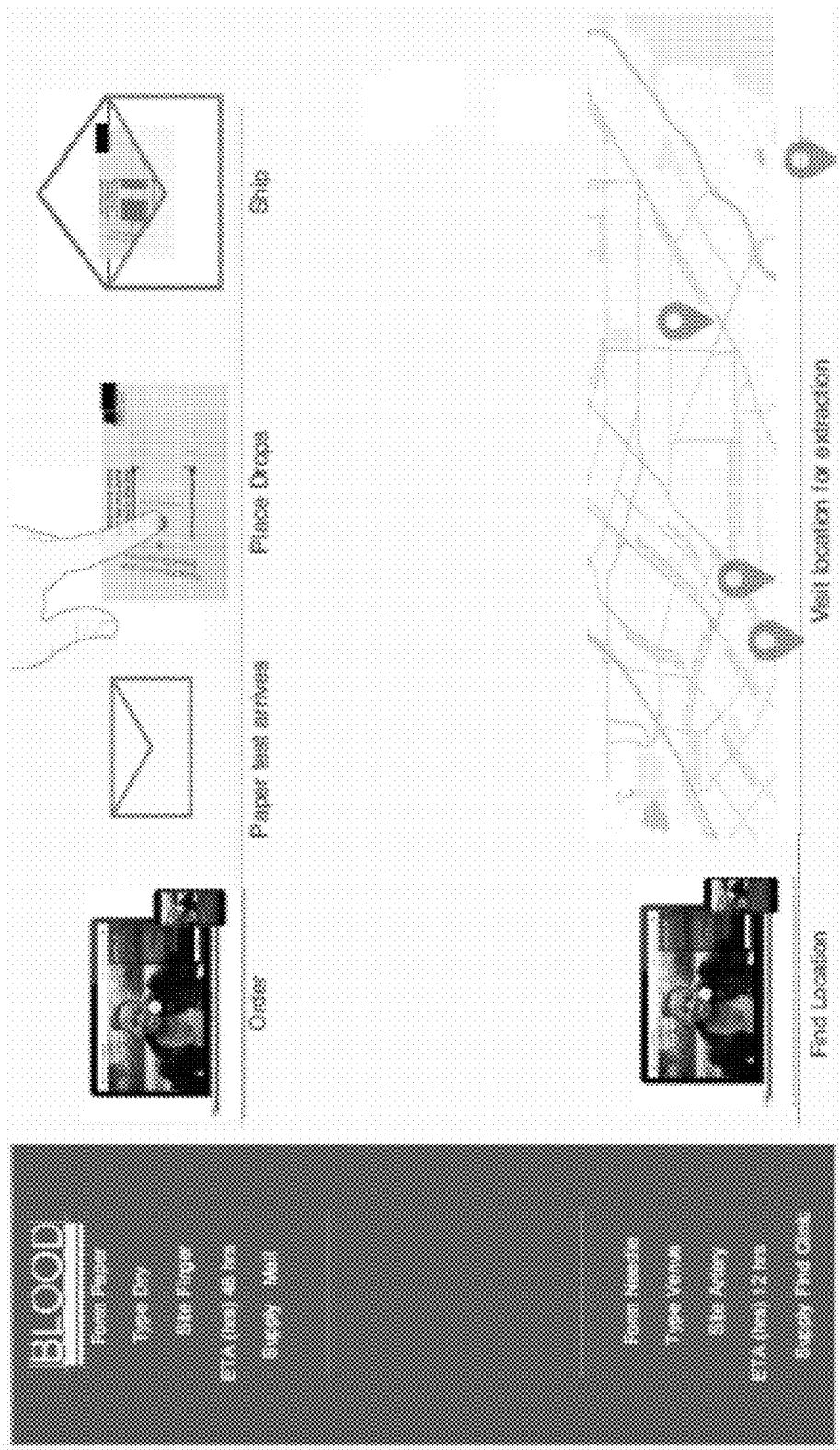
FIG. 38 illustrates use of a blood test kit or a blood test lab to obtain blood test information of the user that is to be annotated into the personal medical record database to track the variation of blood analysis (blood analysis history) as a user ages.

FIG. 26I illustrates blood test processes that a user may perform with the personal medical record software application. The blood testing lab can directly add the results to the data base of personal medical records of a user. The diagnostic test results can be displayed as part of the personal medical record 2200. FIGS. 38-39 illustrate how a blood test kit (or a blood test ordered through the medical record software application) may be used to obtain blood test information for the personal medical record database and software application.

Figure 26J:
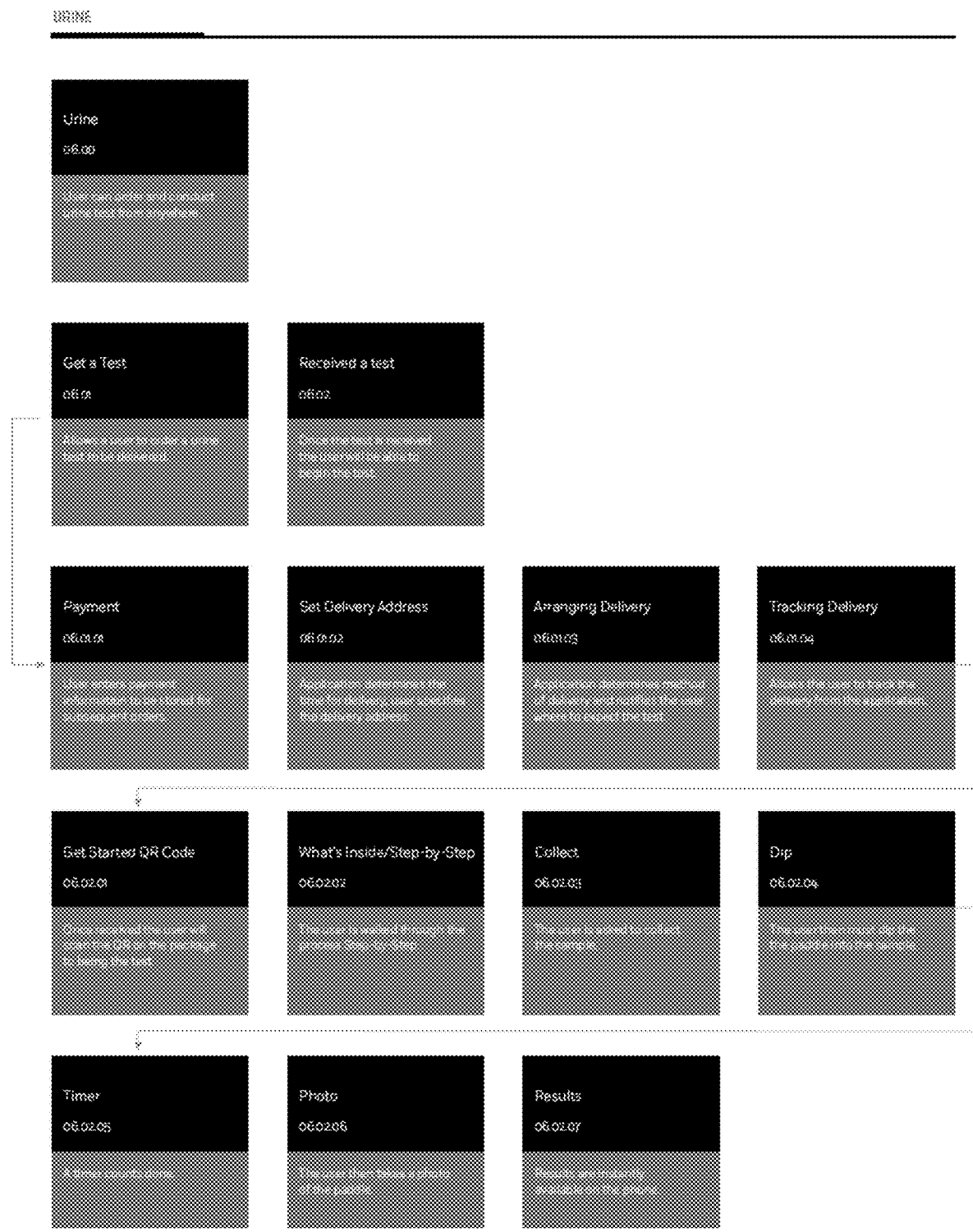

FIG. 26J illustrates urine test processes that a user performs with the personal medical record software application and a urine test kit including a urine test paddle. The results of the urine test paddle can be added to the data base of personal medical records of a user. Accordingly, the test results of the urine test paddle can be displayed as part of the personal medical record 2200. FIGS. 33-37 illustrate how a urine test kit is used to obtain urine test information for the personal medical record database and software application.

Figure 26K:
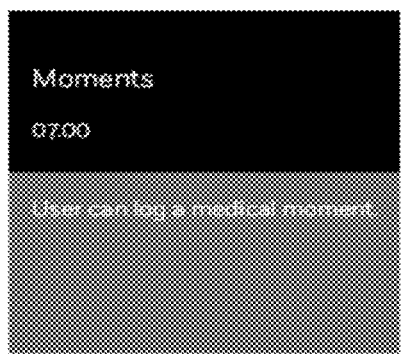
Figure 26K:
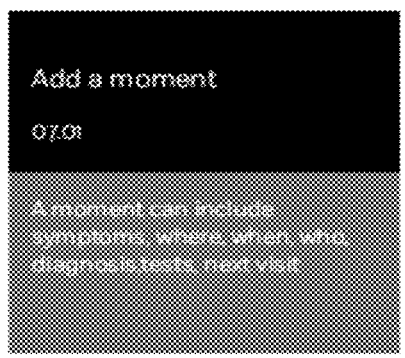
Figure 26K:
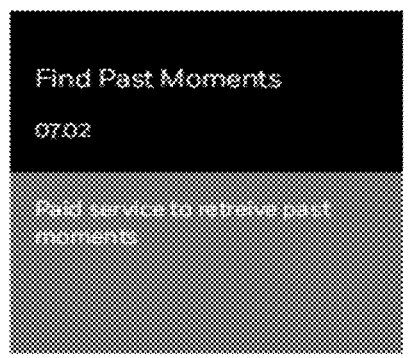
Figure 26K:
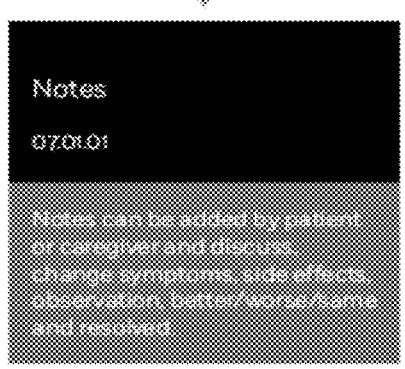
Figure 26K:

FIG. 26K illustrates processes executed by the personal medical record software application to log a medical moment to the personal medical record history of a user. A medical moment 2215 can include chief complaint, history of illness, symptoms, where, when, who, tests, physical examinations, diagnosis, assessment and plan, as well as the next scheduled doctor visit. Past medical moments can be stored in the medical records data base and retrieved for comparison and analysis. Notes can be added to the medical moment by the patient or caregiver. The notes can indicate discussion with the patient/doctor, change of symptoms, side effects, observations, whether symptoms have improved, become worse, remain the same, or are resolved. Supporting patient photos and photos of documents may be attached to the log of a medical moment.

Figure 23:
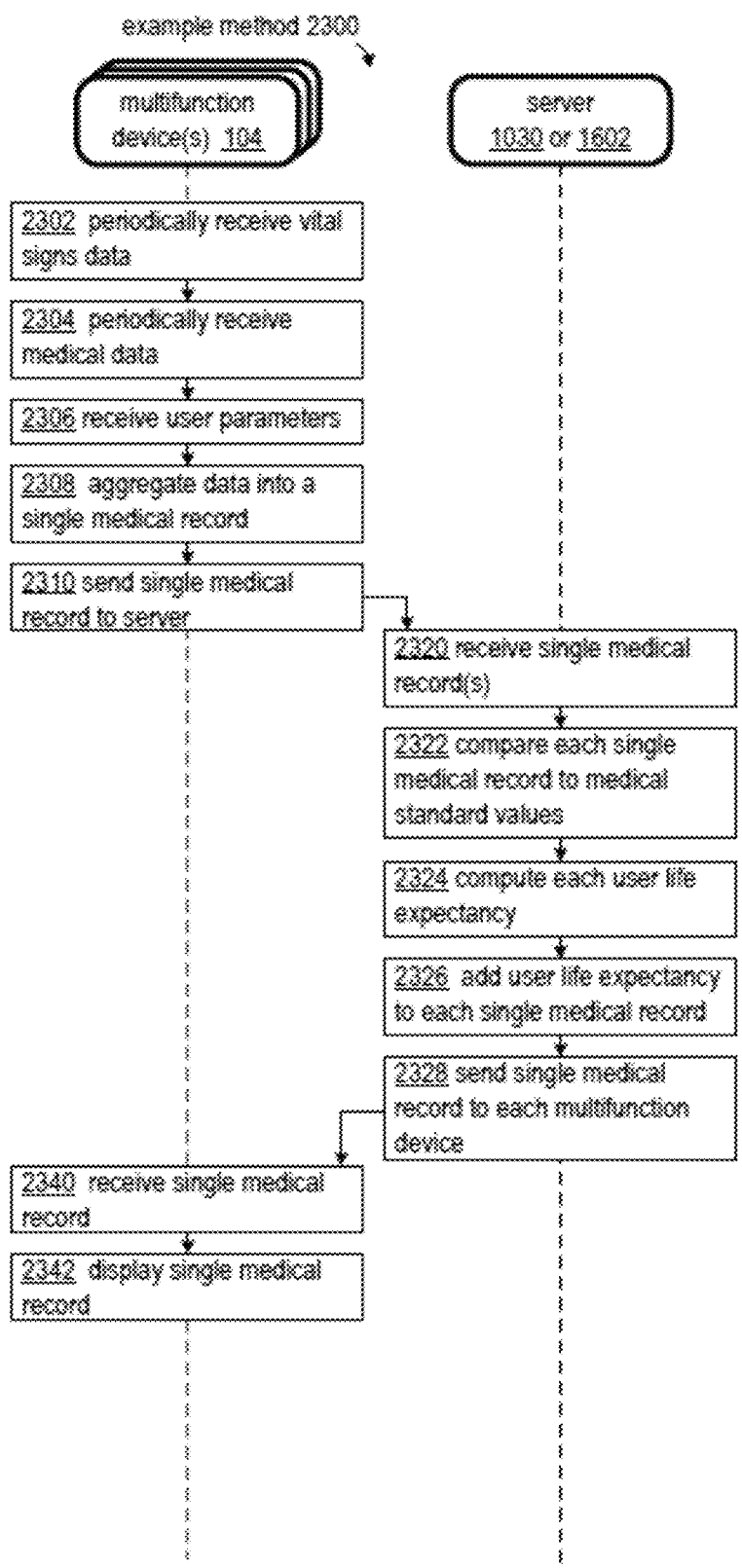
FIG. 23 illustrates an example method of formation and display of a personal medical record.

Referring now to FIG. 23, a flowchart of an example method 2300 for aggregating one or more medical records associated with one or more multifunction devices 104 and a server is shown. The method begins with operation 2302.

At an operation 2302, each multifunction device 104 periodically receives vital signs data. The process then goes to operation 2304.

At an operation 2304, each multifunction device 104 periodically receives medical data.

"Periodically" can mean number of different things in this context. For example, a user may use the vital signs scanner 102 to gather vital signs data multiple times per day (e.g., every hour), once per day (e.g., at noon), once per week (e.g., every Friday), once per month (e.g., the first of the month), or any other appropriate time period for periodically gathering data. The period of time "periodically receiving" is not necessarily uniform or consistent. For example, on some days a user may use the vital signs scanner 102 to gather data at noon and 3 pm, while gathering data at 6 am and 1 pm on another day, and so on. However, the usefulness of the vital signs data is likely to increase as the frequency and consistency of the time periods increases. For example, if a user gathers vital sign data every hour, on the hour, for many days in a row, then that vital signs data is likely to be more useful than vital signs data gathered once a day at inconsistent times on inconsistent days. The process goes to operation 2306.

At an operation 2306, each multifunction device 104 receives user parameters. The process then goes to operation 2308.

At an operation 2308, each multifunction device 104 aggregates the data into a single medical record, such as the single medical record 2200 shown for example with reference to FIG. 22. The process then goes to operation 2310.

At an operation 2310, each multifunction device 104 sends the user's single medical record to the server (e.g., server 1030 shown in FIG. 10, server 1435 shown in FIG. 14, or server 1602 shown in FIG. 16). The process then goes to operation 2320.

At an operation 2320, the server (e.g., server 1030 shown in FIG. 10, server 1435 shown in FIG. 14, or server 1602 shown in FIG. 16) receives each single medical record from each multifunction device 104. The process then goes to operation 2322.

At an operation 2322, the server compares each single personal medical record to medical standard values. The process then goes to operation 2324.

At an operation 2324, the server computes each user's life expectancy based on the comparisons. The process then goes to operation 2326.

At an operation 2326, the server adds user life expectancy information to each single personal medical record. The process then goes to operation 2328.

At an operation 2328, the server sends each single personal medical record to each corresponding multifunction device 104.

In one embodiment, the server (e.g., server 1030 shown in FIG. 10, server 1435 shown in FIG. 14, or server 1602 shown in FIG. 6) can generate one or more vital signs groups for each user. A vital signs group may include, for example, two or more users associated with the multifunction devices 104. The server can group users by at least one of the following: age sex, ethnicity, height weight, or any other category of information from the single medical records. In another embodiment, a user can build a custom vital signs group. For example, a user may decide to build a group that includes people in the user's family, people in the user's office, people on the users football team, or any other group that the user decides.

At an operation 2340, each multifunction device 104 receives the users updated single medical record from the server. At an operation, each multifunction device 104 displays the users updated single medical record. The multifunction device 104 can also display comparative information related to users from one or more of the vital signs groups.

Figure 24:
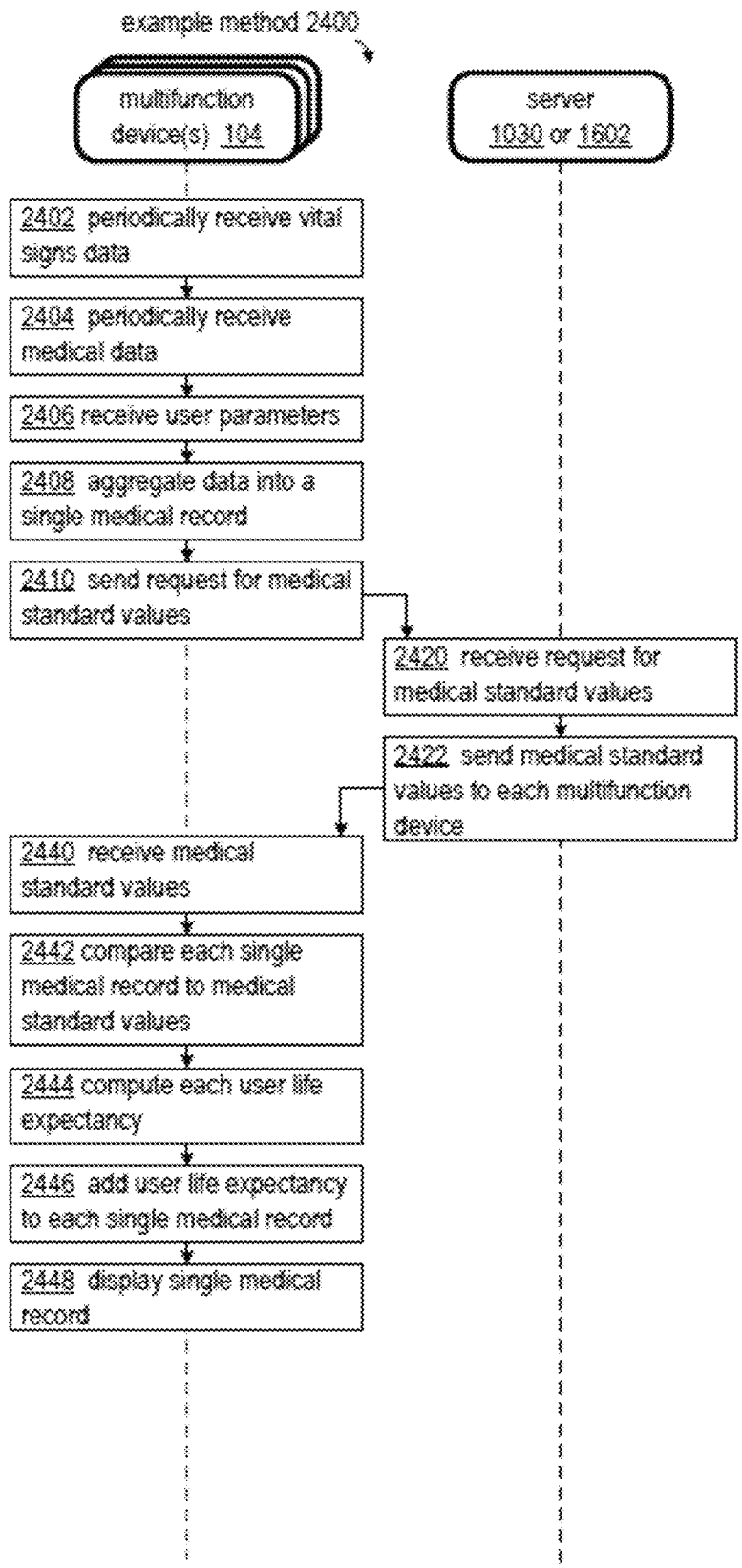
FIG. 24 illustrates another example method of formation and display of a personal medical record.

Referring now to FIG. 24, a flowchart of an example method 2400 for aggregating one or more medical records associated with one or more multifunction devices 104. Methods 2300 and 2400 differ in at least one important way. In the method 2300 of FIG. 23, life expectancy calculations are performed primarily by the server. In contrast, with method 2400 of FIG. 4, life expectancy calculations are primarily performed by at each multifunction device 104.

At an operation 2402, each multifunction device 104 periodically receives vital signs data.

At an operation 2404, each multifunction device 104 periodically receives medical data. The concept of "periodically receiving" is discussed above with reference to FIG. 23 and applies to FIG. 24 as well.

At an operation 2406, each multifunction device 104 receives user parameters.

At an operation 2408, each multifunction device 104 aggregates the data into a single medical record, such as the single medical record 2200 shown for example with reference to FIG. 22.

At an operation 2410, each multifunction device 104 sends a request for medical standard values to the server.

At an operation 2420, the server receives each request for medical standard values. As discussed with reference to FIG. 23, the server can generate one or more vital signs groups for each user. Alternatively, a user can build a custom vital signs group.

At an operation 2422, the server sends each medical standard values to each corresponding multifunction device 104.

At an operation 2440, each multifunction device receives the appropriate medical standard values for the user.

At an operation 2442, each multifunction device 104 compares each single medical record to the medical standard values.

At an operation 2444, each multifunction device 104 computes the user's life expectancy based on the comparison.

At an operation 2446, each multifunction device 104 adds the user's life expectancy information to the user's single medical record.

At an operation 2448, each multifunction device 104 displays the user's updated single medical record. The multifunction device 104 can also display comparative information related to users from one or more of the vital signs groups.

CONCLUSION

When implemented in software, the elements of the embodiments of the invention are essentially the code segments or instructions to perform the functional tasks described herein. The code segments or instructions are executable by a processor, such as processor 206,840,2255 and can be stored in a storage device or a processor readable storage medium, such as memory 208,841,2257 awaiting execution. The processor readable storage medium may include any non-transitory medium that can be read and written to store information. Examples of the processor readable storage medium include an electronic circuit, a semiconductor memory device, a read only memory (ROM), a flash memory, an erasable programmable read only memory (EPROM), a floppy diskette, a CD-ROM, an optical disk, a hard disk. The code segments or instructions may be downloaded via computer networks such as the Internet, Intranet, etc. into the processor readable storage medium.

While certain embodiments of the disclosure have been described, these embodiments have been presented by way of example only, and are not intended to limit the scope of the disclosure. Indeed, the novel methods, systems, and devices described herein may be embodied in a variety of other forms. Furthermore, various omissions, substitutions and changes in the form of the methods, systems, and devices described herein may be made without departing from the spirit of the disclosure. For example, certain features that are described in this specification in the context of separate implementations may also be implemented in combination in a single implementation. Conversely, various features that are described in the context of a single implementation may also be implemented in multiple implementations, separately or in sub-combination. Moreover, although features may be described above as acting in certain combinations and even initially claimed as such, one or more features from a claimed combination may in some cases be excised from the combination, and the claimed combination may be directed to a sub-combination or variations of a sub-combination. Accordingly, the claimed invention is to be limited only by patented claims that follow below.

What is claimed is:

1. A method for forming an integrated medical historic record of a user, the method comprising:
    periodically receiving, at a portable electronic device, vital signs data in a digital signal format, the vital signs data being measured by the user using a portable vital signs scanner, wherein:
        the vital signs data includes data captured when the portable vital signs scanner is gripped between fingers of the user and data captured when the portable vital signs scanner is pressed against the forehead of the user;
        the portable vital signs scanner comprises a temperature sensor and a motion sensor; and
        the portable vital signs scanner converts the vital signs data from an analog signal format to the digital signal format:
    indicating to the user, while the vital signs data is measured, a quality of the vital signs data and a current progress of a vital sign scan;
    receiving, at the portable electronic device, user parameters associated with the user;
    determining that a portion of the vital signs data meets a signal quality criterion, the signal quality criterion being based on a temperature measurement measured by the temperature sensor and a motion measurement measured by the motion sensor;
    aggregating, at the personal electronic device, the received user parameters with the determined portion of the vital signs data into a single personal medical record;
    associating the single personal medical record with the user;
    transmitting the single personal medical record to a computer server;
    updating, at the computer server, the single personal medical record by adding medical information related to the vital signs data in the personal medical record;
    sending the updated single personal medical record from the computer server to the personal electronic device; and
    displaying to the user, the updated single personal medical record.

2. The method of claim 1, further comprising:
    periodically receiving medical data in response to a medical examination performed by a health care practitioner; and
    further aggregating the medical data into the single personal medical record.

3. The method of claim 1, wherein the aggregating of data into the single personal medical record includes automatically populating values into parameter fields of the single personal medical record in response to receiving the vital signs data.

4. The method of claim 1, wherein the aggregating of data into the single personal medical record includes automatically populating values into parameter fields of the single personal medical record in response to receiving the vital signs data.

5. The method of claim 1, wherein updating the single personal medical record includes adding a user life expectancy to the single personal medical record.

6. The method of claim 1, wherein the displaying includes displaying the updated single personal medical record on a display device of the portable electronic device.

7. The method of claim 1, further comprising:
    generating a vital signs group of users having similar traits; and
    assigning at least a first user to the vital signs group.

8. The method of claim 7, wherein the similar traits include at least one of: age; gender; height; weight; or infirmity.

9. The method of claim 7, further comprising:
    receiving a single personal medical record for the first user; and
    comparing the single personal medical record of the first user to other single medical records of the vital signs group.

10. The method of claim 1, wherein the portable electronic device is a multi-function device.

11. A system for aggregating one or more medical records, the system comprising:
    a computer server storing a database of personal medical records associated with one or more users;
    a plurality of portable electronic devices operatively coupled to the computer server via a communication network, wherein each portable electronic device of the plurality of portable electronic devices is associated with a different user, and wherein a first portable electronic device of the plurality of portable electronic devices is configured to:
        periodically receive vital signs data in a digital signal format, the vital signs data being measured by a first user using a portable vital signs scanner, wherein:
            the vital signs data includes data captured when the portable vital signs scanner is gripped between fingers of the user and data captured when the portable vital signs scanner is pressed against the forehead of the user;
            the portable vital signs scanner comprises a temperature sensor and a motion sensor; and
            the portable vital signs scanner converts the vital signs data from an analog signal format to the digital signal format;
        indicate to the user, while the vital signs data is measured, a quality of the vital signs data and a current progress of a vital sign scan;
        receive user parameters;
        determining that a portion of the vital signs data meets a signal quality criterion, the signal quality criterion being based on a temperature measurement measured by the temperature sensor and a motion measurement measured by the motion sensor;
        aggregate the determined portion of the vital signs data and the received user parameters into a single personal medical record;
        associate the single personal medical record with the first user;

transmit the single personal medical record to the computer server;
receive an updated single personal medical record from the computer server; and
display the updated single personal medical record to the first user;
wherein the computer server is configured to:
receive the single personal medical record transmitted by the first portable electronic device;
update the single personal medical record by adding medical information related to the vital signs data in the personal medical record; and
transmit the updated single personal medical record to the first personal electronic device.

12. The system of claim 11, wherein at least one portable electronic device of the plurality of portable electronic devices is a multi-function device.

13. The system of claim 12, wherein the multi-function device is one of a smartphone, a tablet PC, or a smart watch.

14. The system of claim 11, wherein the computer server is further configured to compute the first user's life expectancy based at least partly on the aggregated data in the single personal medical record, and add the computed life expectancy to the single personal medical record associated with the first user.

15. The method of claim 13, wherein the multi-function device is one of a smartphone, a tablet PC, or a smart watch.

16. The system of claim 11, wherein the plurality of portable electronic devices includes a second portable electronic device configured to:
periodically receive additional vital signs data measured by a second user using an additional portable vital signs scanner;
receive user parameters associated with second user;
aggregate the received additional vital signs data and the user parameters of the second user into a personal medical record;
associate the personal medical record with the second user;
transmit the second user's personal medical record to the computer server;
receive an updated second user's personal medical record from the computer server; and
display the updated second user's personal medical record to the second user;
wherein the computer server is configured to:
receive the second user's personal medical record transmitted by the second portable electronic device;
update the second user's personal medical record by adding medical information related to the additional vital signs data in the second user's personal medical record; and
transmit the updated second user's personal medical record to the second personal electronic device.

17. The system of claim 16, wherein the second personal portable electronic device is one of a smartphone, a tablet PC, or a smart watch.

18. The system of claim 16, wherein the computer server is further configured to compute the second user's life expectancy based at least partly on the aggregated data in the second user's personal medical record, and add the computed life expectancy to the second user's personal medical record.

* * * * *